(12) United States Patent  
Takashima

(10) Patent No.: US 8,125,539 B2
(45) Date of Patent: Feb. 28, 2012

(54) INFORMATION-PROCESSING APPARATUS AND METHOD DETECTING LIVING-BODY INFORMATION

(75) Inventor: Kouichiro Takashima, Tokyo (JP)

(73) Assignee: Sony Corporation, Tokyo (JP)

( * ) Notice: Subject to any disclaimer, the term of this patent is extended or adjusted under 35 U.S.C. 154(b) by 547 days.

(21) Appl. No.: 12/252,902

(22) Filed: Oct. 16, 2008

(65) Prior Publication Data

US 2009/0122147 A1    May 14, 2009

(30) Foreign Application Priority Data

Nov. 9, 2007    (JP) .................................. 2007-292296

(51) Int. Cl.
*H04N 5/76*    (2006.01)
(52) U.S. Cl. .................... 348/231.6; 348/231.4; 348/239
(58) Field of Classification Search .................... 348/77, 348/231.3, 231.6, 239, 231.4
See application file for complete search history.

(56) References Cited

U.S. PATENT DOCUMENTS

| | | | |
|---|---|---|---|
| 2006/0088297 A1* | 4/2006 | Iguchi et al. .................. | 358/906 |
| 2007/0263978 A1* | 11/2007 | Yang et al. ....................... | 386/52 |
| 2008/0129839 A1* | 6/2008 | Asukai et al. ............ | 348/231.99 |

FOREIGN PATENT DOCUMENTS

| | | |
|---|---|---|
| JP | 11-205733 | 7/1999 |
| JP | 2002-204419 | 7/2002 |
| JP | 2002-330390 | 11/2002 |
| JP | 3514236 | 1/2004 |
| JP | 2005-128884 | 5/2005 |
| JP | 2006-026211 | 2/2006 |
| JP | 2006080644 A * | 3/2006 |
| JP | 2007-049592 | 2/2007 |

OTHER PUBLICATIONS

Japanese Office Action issued on Dec. 15, 2009 for corresponding Japanese Patent Application 2007-292296.
Japanese Office Action issued on Oct. 8, 2009, for corresponding Japanese Patent Application JP 2007-292296.

* cited by examiner

*Primary Examiner* — Jason Whipkey
(74) *Attorney, Agent, or Firm* — K&L Gates LLP

(57) ABSTRACT

An information-processing apparatus processes information obtained by shooting an image of a subject and by collecting ambient sound of the subject. The apparatus contains an image-and-sound-recording unit that shoots the image of the subject to output image information on the image and collects the ambient sound of the subject to output sound information on the ambient sound and an information output unit that detects living-body information showing emotion of living-body of an operator who operates the image-and-sound-recording unit to output the living-body information. The apparatus also contains an information-processing unit that establishes correspondence between the living-body information outputted from the information output unit and at least one of the image information of the subject and the sound information of the ambient sound of the subject, the image information and the sound information being outputted from the image-and-sound-recording unit.

14 Claims, 30 Drawing Sheets

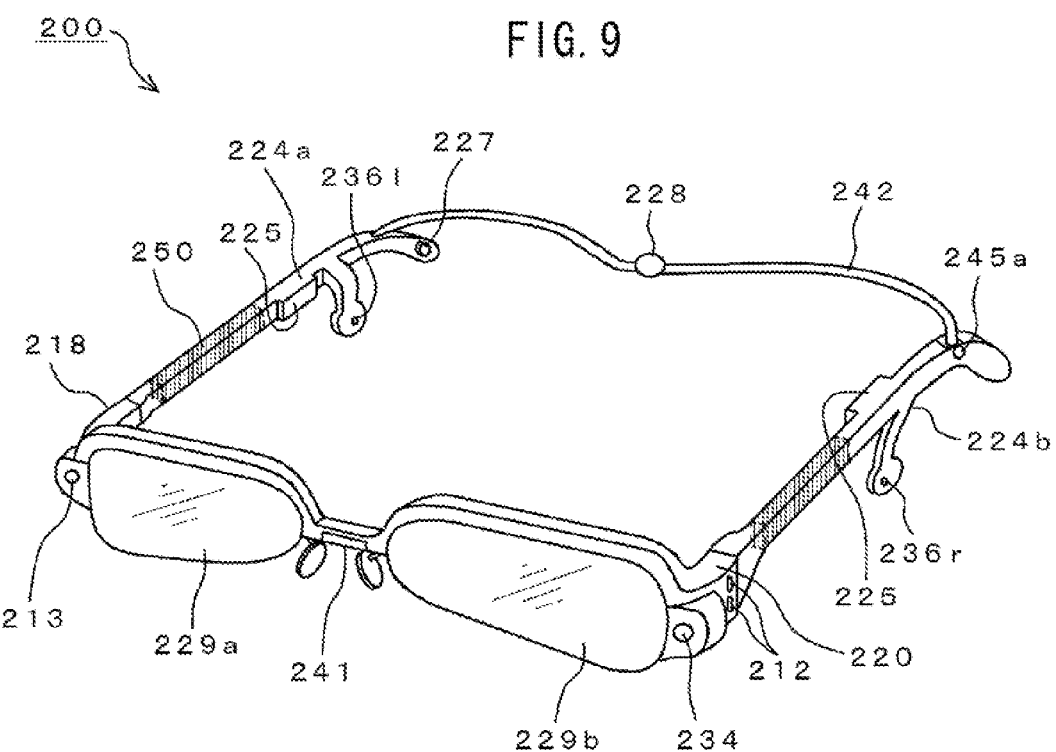

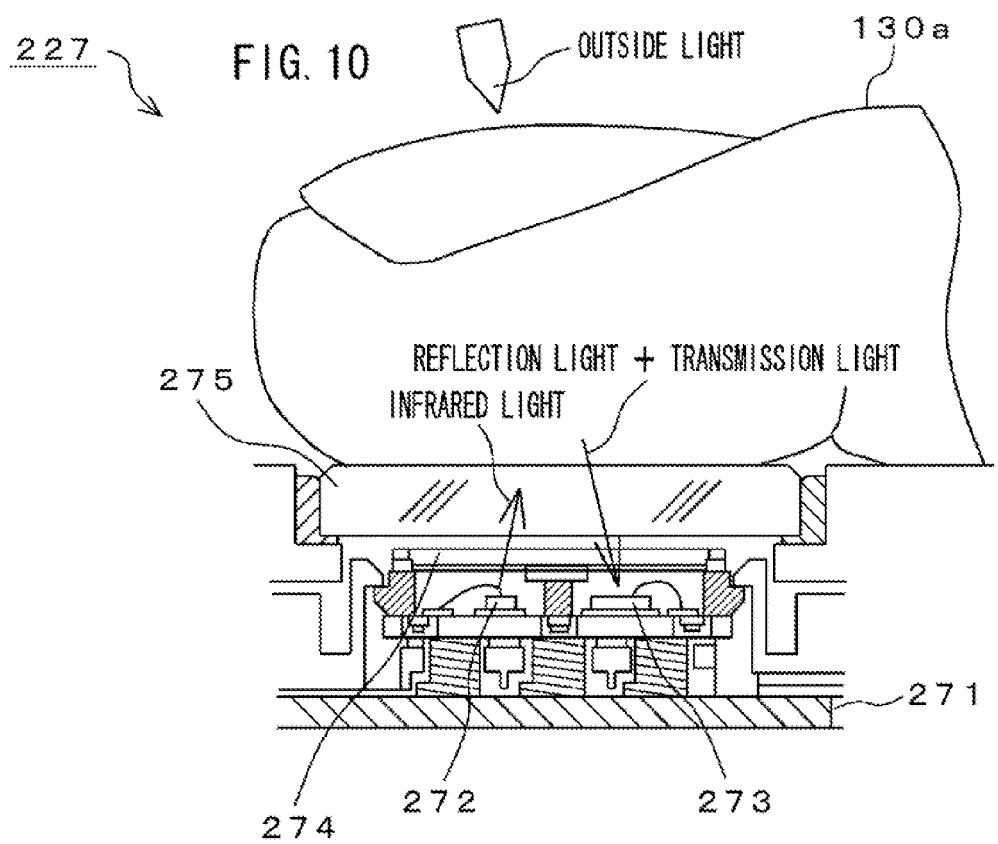
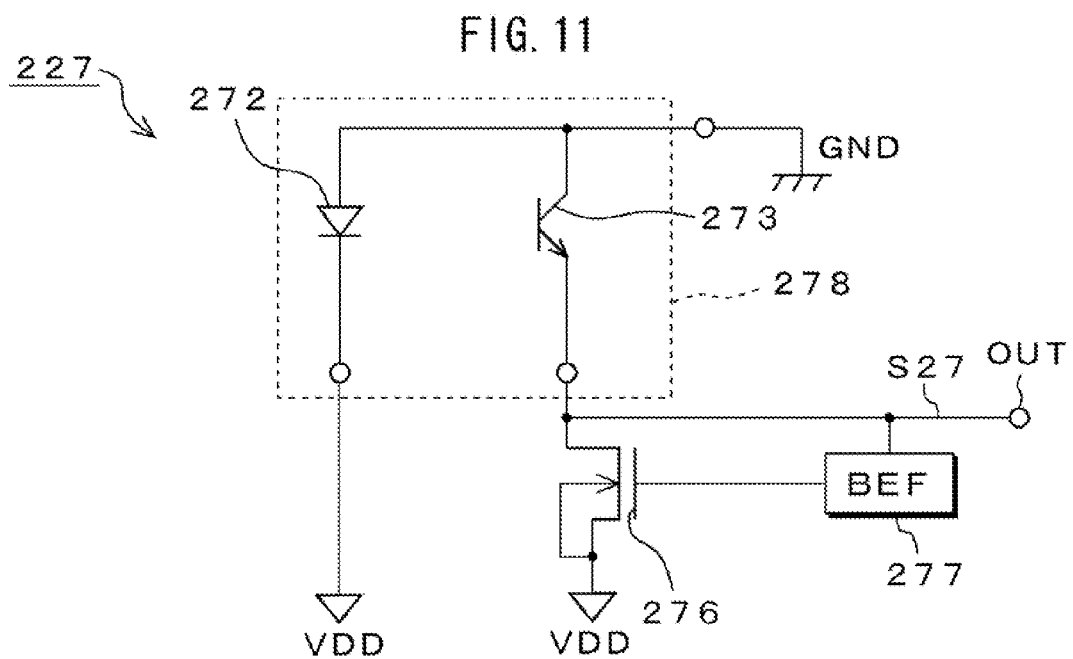

BLOOD PRESSURE

PULSE

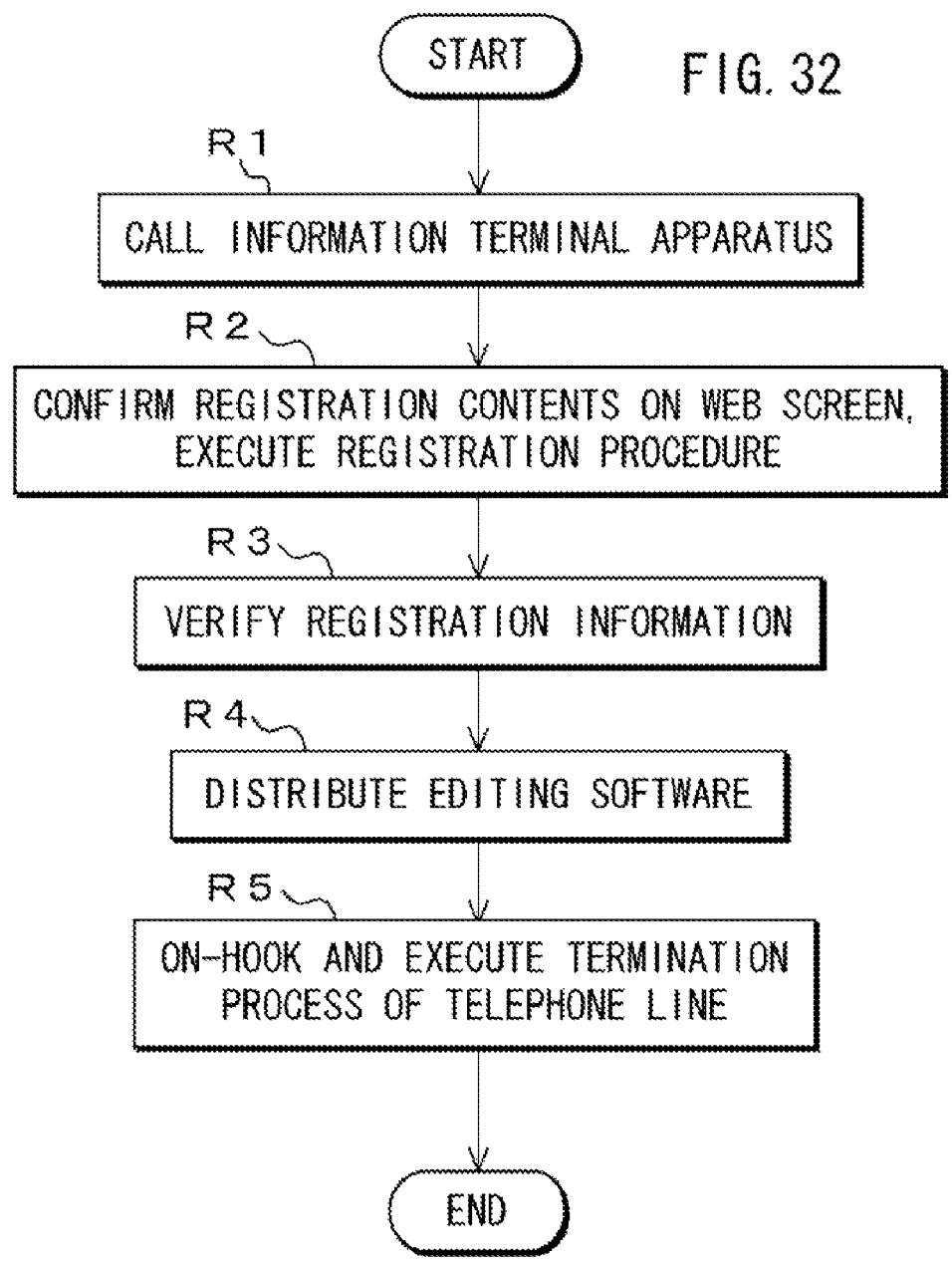

INFORMATION-PROCESSING APPARATUS AND METHOD DETECTING LIVING-BODY INFORMATION

CROSS REFERENCES TO RELATED APPLICATIONS

The present application claims priority to Japanese Patent Application JP 2007-292296 filed in the Japanese Patent Office on Nov. 9, 2007, the entire contents of which is being incorporated herein by reference.

BACKGROUND

The present application relates to an information-processing apparatus, an information-processing method, a program, a recording medium and an information-processing system, which are applicable to a video camera taking a moving picture, a digital camera taking a still picture, a mobile phone with camera, a mobile terminal apparatus with camera, an information-reproducing apparatus that reproduces image and sound information obtained from those apparatuses, a system provided with a recording-editing-reproducing apparatus saving data or the like.

In recent years, it has been attempted to increase recording medium capacity, to miniaturize an apparatus, and intensify mutual communication between the apparatuses, so that high-capacity personal images and high-capacity still-picture can be shot and viewed. For example, a user (operator) has often recorded images of subjects, views-landscapes and the like and ambient sounds of the subjects by using a video camera in order to shoot memorial images in an event of an athletic meet, an excursion or the like.

The video camera contains an imaging unit, a sound collection unit, a recording unit, an operation unit, and a control unit. The imaging unit shoots images of subjects, views-landscapes and the like based on the operation of the operation unit, the sound collection unit records ambient sound of the subjects, and the recording unit receives a memory control of the control unit and records moving picture of subjects or the like shot by the imaging unit and ambient sound of the subjects collected by the sound collection unit.

Also, the digital camera or the mobile phone with camera shoots the subject to record a still picture thereof on a recording unit. For the recording units of the video camera, the digital camera and the mobile phone with camera mentioned above, detachable recording media such as memory sticks have been often used. Along with the increasing of recording medium capacity, it becomes possible to save enormous quantity of personal contents (still pictures, moving picture). These recording media are loaded on a recording-editing-reproducing apparatus in which the contents therein are shifted to an editing process to edit and save memorial image and sound information. The editing is an operation in order to make a state worthy for an individual person to view these contents at a later date. There are many cases in which the image and sound information after the edition serves for an affair being viewed at a later date.

Meanwhile, Japanese Patent No. 3514236 discloses an image and sound automatic editing apparatus, a method thereof, and a recording medium thereof with reference to this kind of recording-editing-reproducing apparatus (see Page 4, FIG. 2). This image and sound automatic editing apparatus measures a brain wave of a user, simultaneously image and sound of subject are recorded, in synchronization with the recording, and analyzes the brain wave of the user after the information is obtained to automatically discriminate the images and sound when the user's arousal level is high. The discriminated images and sound when the user's arousal level is high are edited for summarization.

Also, Japanese Patent Application Publication No. 2005-128884 discloses an editing apparatus of information contents and an editing method thereof (see Page 3, FIG. 6). This editing apparatus produces emotion parameter showing degrees of emotion by using information based on living-body information, produces a command for summary production in response to the emotion level obtained by digitizing this emotion parameter, and produces a summary of the information content data using this command.

SUMMARY

Meanwhile, the above-mentioned video camera, digital camera, mobile phone with camera, and information-processing system which deals with the recording-reproducing-editing apparatus have issues as follows:

(1) According to the video camera, the digital camera, the mobile phone with camera and the like, increasing of recording medium capacity, miniaturization of an apparatus and intensification of mutual communication between the apparatuses have been attempted and it becomes possible to shoot high-capacity personal images, to shoot high-capacity still picture and to view these images and still picture. However, while the information of the image and the ambient sounds of the subjects becomes easy to be shot and recorded, the content data forming the image and sound information including still picture and the moving-picture of subjects, views-landscapes or the like becomes enormous quantity too much, and the editing operation thereof has spent for a lot of hours under present circumstances.

Mostly, human beings takes initiative in the editing operations, so that it takes enormous editing time and the value of the contents themselves may be lost by leaving the content data which are finally obtained in an unedited condition.

(2) According to the recording-editing-reproducing apparatus as seen in Japanese Patent No. 3514236, the brain wave of the user is measured, simultaneously image and sound of subject are recorded, in synchronization with the recording, and the brain wave of the user is analyzed after the information is obtained to automatically discriminate the images and sound when the user's arousal level is high. Consequently, even if the discriminated images and sound when the user's arousal level is high can be edited for summarization, it is difficult to extract the image information and the sound information automatically at a period of time when the emotion of the living-body is heightened to sweat in a hand, in an event of an athletic meet, an excursion or the like.

(3) According to the editing apparatus as seen in Japanese Patent Application Publication No. 2005-128884, a command for summary production is produced in response to the emotion level obtained by digitizing the emotion parameter showing degrees of emotion produced by using information based on living-body information, and a summary of the information content data is produced using this command. Consequently, even if images and sound of a scene expressed with interest and a surprising scene could be edited for summarization, it is difficult to extract the image information and the sound information automatically at a period of time when the emotion of the living-body is heightened to sweat in a hand while shooting the image of the subject and recording the sound, in an event of an athletic meet, an excursion or the like.

It is desirable to provide an information-processing apparatus, an information-processing method, a program, a recording medium, and an information-processing system in which editing work can be much improved as compared with a case in which the editing is executed by a manual operation on the way of shooting the subject image.

According to an embodiment, there is provided an information-processing apparatus that processes information obtained by shooting an image of a subject and by collecting ambient sound of the subject. The apparatus contains an image-and-sound-recording unit that shoots the image of the subject to output image information on the image and collects the ambient sound of the subject to output sound information on the ambient sound, an information output unit that detects living-body information showing emotion of living-body of an operator who operates the image-and-sound-recording unit to output the living-body information, and an information-processing unit that establishes correspondence between the living-body information outputted from the information output unit and at least one of the image information of the subject and the sound information of the ambient sound of the subject, the image information and the sound information being outputted from the image-and-sound-recording unit.

In an embodiment of the information-processing apparatus, in case of processing the information obtained by shooting the image of the subject and by collecting the ambient sound of the subject, the image-and-sound-recording unit shoots the image of the subject to output image information on the image and collects the ambient sound of the subject to output sound information on the ambient sound. The information output unit detects the living-body information showing emotion of living-body of an operator who operates the image-and-sound-recording unit to output the living-body information. On the premise of this, the information-processing unit establishes correspondence between the living-body information outputted from the information output unit and at least one of the image information of the subject and the sound information of the ambient sound of the subject, which are outputted from the image-and-sound-recording unit.

Consequently, it is possible to automatically extract the image information and the sound information at period of time when emotion of the living-body of the operator is heightened to sweat in a hand during the operator is shooting the image of the subject, thereby enabling the operator's specific image and sound information files to be easily and simply produced, which are obtained by editing the image information and the sound information extracted automatically here. Accordingly, it becomes possible to improve editing work dramatically as compared with a case in which an editing start point, an editing end point or the like is appointed and inputted by a manual operation on the way of shooting the image of the subject.

According to another embodiment, there is provided an information-processing apparatus that processes information obtained by shooting an image of a subject and by collecting ambient sound of the subject, the information including editing start point information and editing end point information with living-body information that shows emotion of living-body of an operator corresponding to at least one of image information of the subject and sound information of ambient sound of the subject, the image information and the sound information being shot and collected. The apparatus contains an input unit that inputs the image information of the subject and the sound information when recording the ambient sound of the subject, any one of the image information and the sound information including the editing start point information or the editing end point information. The apparatus also contains a judgment unit that judges whether or not automatic editing of the image information of the subject and the sound information when recording the ambient sound of the subject is performed based on instruction from outside, the image information and the sound information being inputted by the input unit. The apparatus further contains an image-and-sound-processing unit that extracts the image information of the subject and the sound information when recording the ambient sound of the subject in a period of time from a point of time when the editing start point information is added to a point of time when the editing end point information is added from the image information of the subject and the sound information when recording the ambient sound of the subject, the image information and the sound information being judged by the judgment unit so as to execute the edition, and splices the extracted image information and the extracted sound information.

In an embodiment, it is possible to automatically extract the image information and the sound information at a period of time when the emotion of the living-body is heightened to sweat in a hand during the operator is shooting the image of the subject, thereby enabling the operator's specific image and sound information files to be easily and simply produced, which are obtained by editing the image information and the sound information extracted automatically here. Accordingly, it becomes possible to improve editing work dramatically as compared with a case in which an editing start point, an editing end point or the like is appointed and inputted by a manual operation on the way of shooting the image of the subject.

According to a further embodiment, there is provided an information-processing method of processing information obtained by shooting an image of a subject and by collecting ambient sound of the subject. The method includes the steps of obtaining image information by shooting the image of the subject and also obtaining sound information by collecting the ambient sound of the subject, detecting and producing living-body information showing emotion of living-body of an operator who operates an image-and-sound-recording unit, and performing processing to establish correspondence between the produced living-body information and at least one of the image information of the subject and the sound information of the ambient sound of the subject, the image information and the sound information being shot and collected.

In an embodiment, when processing the information obtained by shooting the image of the subject and by collecting the ambient sound of the subject, it becomes possible to execute an editing process or the like by establishing correspondence between the detected and produced living-body information showing the emotion of the living-body of the operator and at least one of the image information of the subject and the sound information of the ambient sound of the subject, the image information and the sound information being shot and collected. Accordingly, it becomes possible to improve editing work dramatically as compared with a method in which an editing start point, an editing end point or the like is appointed and inputted by a manual operation on the way of shooting the image of the subject.

According to an embodiment, there is provided a program product that processes information obtained by shooting an image of a subject and by collecting ambient sound of the subject. The program product is described with a step of obtaining image information by shooting the image of the subject and also obtaining sound information by collecting the ambient sound of the subject, a step of detecting and producing living-body information showing emotion of living-body of an operator who operates the image-and-sound-recording unit, and a step of performing processing to establish correspondence between the produced living-body information and at least one of the image information of the subject and the sound information of the ambient sound of the subject, the image information and the sound information being shot and collected.

In an embodiment of the program product, when processing the information obtained by shooting the image of the subject and by collecting the ambient sound of the subject, it becomes possible to execute an editing process or the like with excellent reproducibility by establishing correspondence between the detected and produced living-body information showing the emotion of the living-body of the operator and at least one of the image information of the subject and the sound information of the ambient sound of the subject, the image information and the sound information being shot and collected.

According to still another embodiment, there is provided a computer readable recording medium that records a program product which processes information obtained by shooting an image of a subject and by collecting ambient sound of the subject. The program product being described with a step of obtaining image information by shooting the image of the subject and also obtaining sound information by collecting the ambient sound of the subject, a step of detecting and producing living-body information showing emotion of living-body of an operator who operates the image-and-sound-recording unit, and a step of performing processing to establish correspondence between the produced living-body information and at least one of the image information of the subject and the sound information of the ambient sound of the subject, the image information and the sound information being shot and collected.

In an embodiment of the recording medium, when processing the information obtained by shooting the image of the subject and by collecting the ambient sound of the subject, it becomes possible to execute an editing process or the like with excellent reproducibility by establishing correspondence between the detected and produced living-body information showing the emotion of the living-body of the operator and at least one of the image information of the subject and the sound information of the ambient sound of the subject, the image information and the sound information being shot and collected.

According to still further embodiment, there is provided an information-processing system that processes information obtained by shooting an image of a subject and by collecting ambient sound of the subject. The system contains an information-processing apparatus that processes information obtained by shooting the image of the subject and by collecting the ambient sound of the subject, and an information-reproducing apparatus that reproduces image information of the subject and sound information of the ambient sound of the subject, the image information and the sound information being obtained from the information-processing apparatus. The information-processing apparatus includes an image-and-sound-recording unit that shoots the image of the subject to output the image information on the image and collects the ambient sound of the subject to output the sound information on the ambient sound, an information output unit that detects living-body information showing emotion of living-body of an operator who operates the image-and-sound-recording unit to output the living-body information, and an information-processing unit that establishes correspondence between the living-body information outputted from the information output unit and at least one of the image information of the subject and the sound information of the ambient sound of the subject, the image information and the sound information being outputted from the image-and-sound-recording unit.

In an embodiment, any one of the embodiments of the information-processing apparatus according to the present application is applied thereto, so that when processing the information obtained by shooting the image of the subject and by collecting the ambient sound of the subject, it becomes possible to execute an editing process or the like by establishing correspondence between the detected and produced living-body information showing the emotion of the living-body of the operator and at least one of the image information of the subject and the sound information of the ambient sound of the subject, the image information and the sound information being shot and collected.

Thus, it becomes possible to establish the operator's specific video and sound information file producing system in which the image information and the sound information at a period of time when the emotion of living-body is heightened to sweat in a hand during the operator is shooting the image of the subject are assembled in a file, a viewing system of the operator's specific image and sound information files, a download system of the operator's specific image and sound information files, and a distribution system of the operator's specific video and sound information files which are recorded on a predetermined recording medium of CD, MD or the like.

The concluding portion of this specification particularly points out and directly claims the subject matter of the present application. However those skills in the art will best understand both the organization and method of operation, together with further advantages and objects thereof, by reading the remaining portions of the specification in view of the accompanying drawing(s) wherein like reference characters refer to like elements.

Additional features and advantages are described herein, and will be apparent from the following Detailed Description and the figures.

BRIEF DESCRIPTION OF THE FIGURES

FIG. 9 is a perspective view of a video camera 200 of a head mounting type as a second embodiment for showing a configuration thereof;

FIG. 10 is a cross-sectional view of a pulse sensor 27 showing a configuration thereof;

FIG. 11 is a block diagram of the pulse sensor 27 showing an internal configuration thereof;

FIG. 32 is a flowchart showing an information processing example in the editing-software-presenting system 700.

DETAILED DESCRIPTION

Embodiments of an information-processing apparatus, an information-processing method, a program, a recording medium and an information-processing system are described as follows with reference to the drawings.

Embodiment 1

Figure 1:
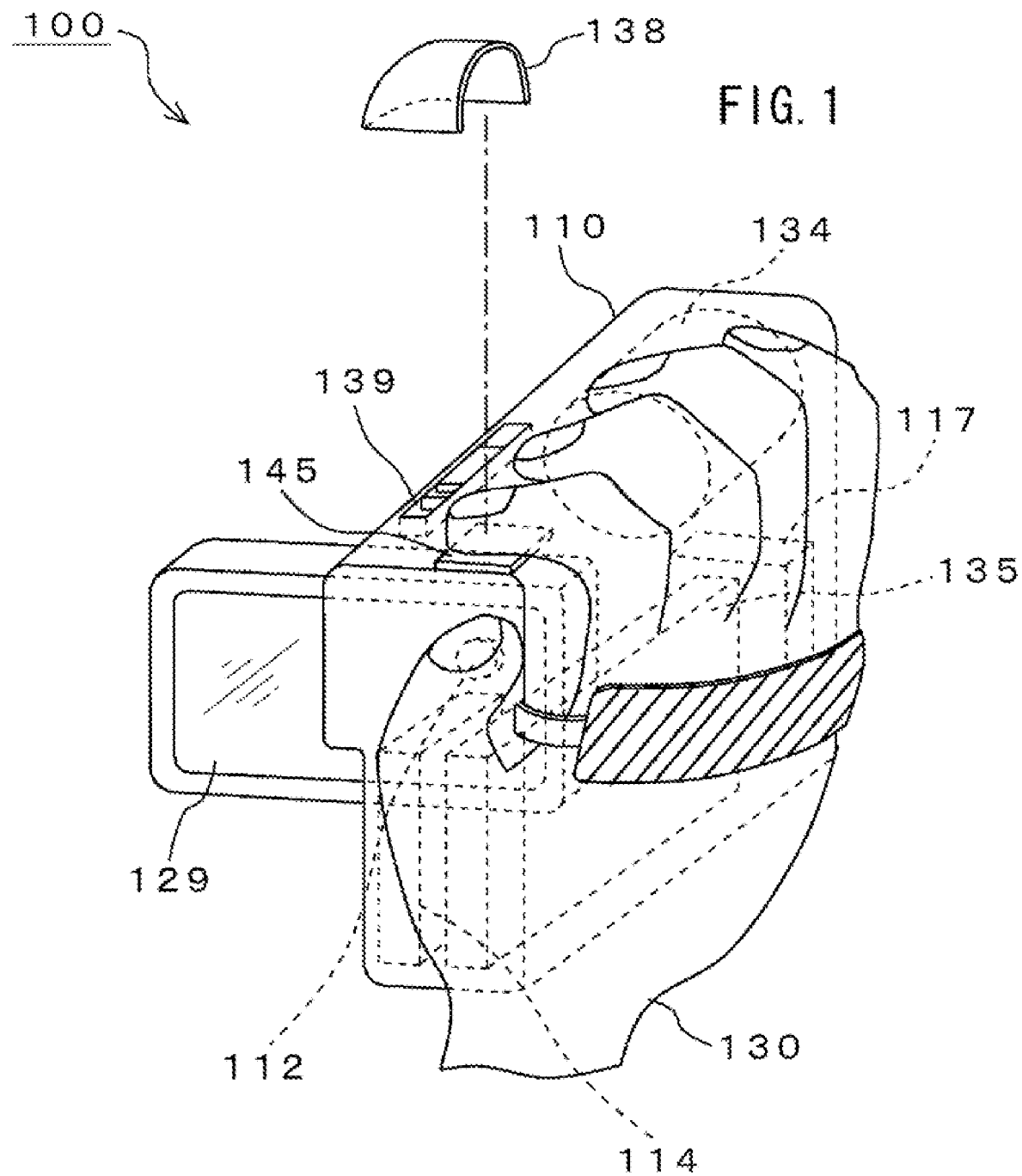
FIG. 1 is a perspective view of a video camera 100 as a first embodiment for showing a configuration thereof.

FIG. 1 shows a configuration of a video camera 100 as a first embodiment. The video camera 100 shown in FIG. 1 constitutes the information-processing apparatus. The video camera 100 shoots an image of a subject to process moving picture information and collects ambient sound of the subject to process sound information.

The video camera 100 includes a main body case 110 constituting an exterior package and an imaging unit 134 is installed at an upper portion of the main body case 110 on the front side thereof. The imaging unit 134 contains an imaging lens, a lens drive mechanism, an image pickup device, which are not shown, and the like. The image pickup device is provided at the rear end of the imaging lens and operates so as to shoot the image of the subject which is introduced by an imaging optical system such as the imaging lens and the lens drive mechanism.

Various kinds of push-button switches 112 such as a power supply switch, a mode switch, a zoom switch, and a shooting start/stop switch are provided on the rear surface, the upper surface and the side surfaces of the main body case 110. The power supply switch is a switch for turning on or off the power supply of the video camera 100. The mode switch is operated when selecting either one of the normal mode and the special recording mode on an occasion of shooting. Here, the special recording mode relates to a mode in which recording is performed with establishing the correspondence between detected and produced living-body information showing emotion of living-body of an operator and image (moving picture) information of the subject and/or sound information of ambient sound of the subject, which are shot and collected. The normal mode relates to a mode other than the special recording mode. In the normal mode, the image information of the subject and the sound information of the ambient sound of the subject which are shot and collected are directly recorded independently of the emotion of living-body of the operator.

Figure 2:
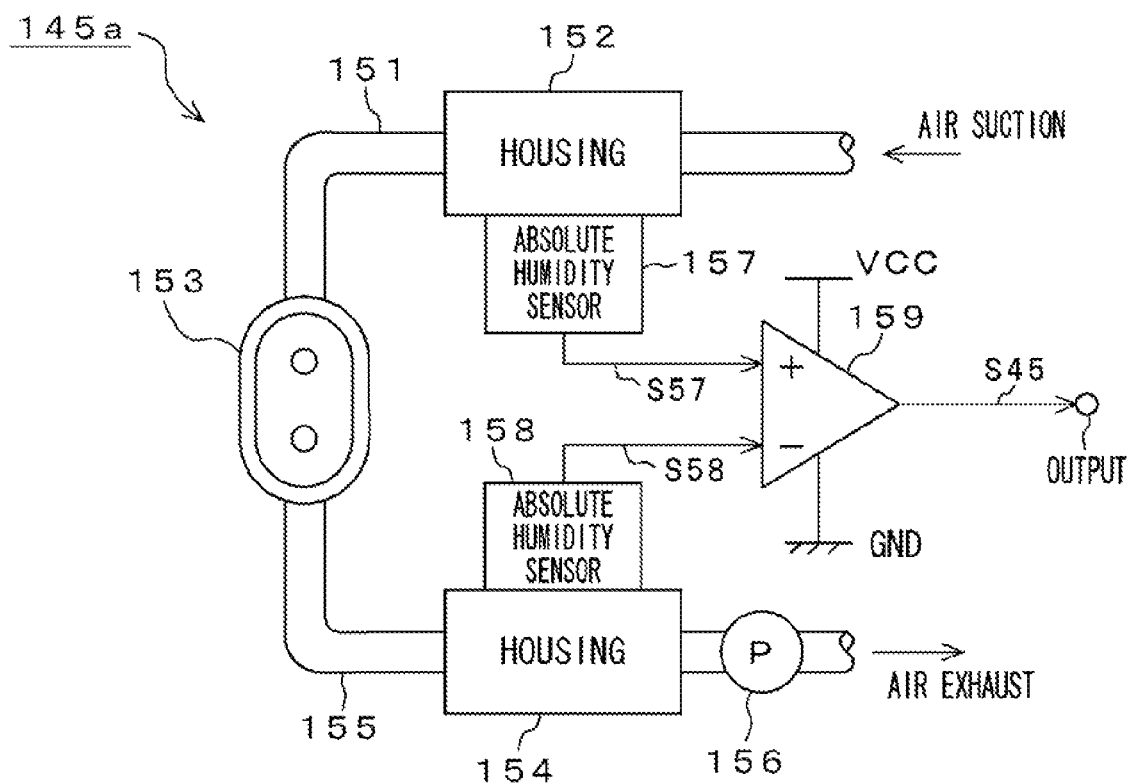
FIG. 2 is a block diagram showing a configuration of a perspiration sensor 145a that is applicable to a living-body sensor unit 145.

In an embodiment, as the mode switch that selects the special recording mode, a living-body sensor unit 145 constituting the information output unit is provided and detects living-body information showing emotion of living-body of an operator who operates the video camera 100 to output the living-body information. For the living-body sensor unit 145, for example, a perspiration (hidrosis) sensor as shown in FIG. 2 is used. The perspiration sensor detects an amount of perspiration of the operator touching the mode switch to output the living-body information showing a perspiration level to the information-processing unit. Of course, it is also allowed to separately provide the living-body sensor unit 145 independently with respect to the mode switch without providing the living-body sensor unit 145 at the position compatibly used for the mode switch such that the operator can touch it during the shooting and sound-collecting operation. In addition, it is also allowed for the living-body sensor unit 145 to use a pulse sensor, a blood pressure sensor or the like other than the perspiration sensor. A sensor cover 138 is provided on the upside of the living-body sensor unit 145 and prevents sweat occurring at a fingertip of the operator 130 from being evaporated. It is also allowed to omit the sensor cover 138.

The zoom switch, which is not shown, is operated when a zoom-up display of the image of the subject or a zoom-down display thereof is executed. The shooting start/stop switch is operated when instructing recording start/stop of the image of the subject shot by the imaging unit 134 in a standby state to the information-processing unit. A microphone for recording sounds, which constitutes a sound collection unit 113, is mounted below the front edge of the imaging lens on the front face of the main body case 110. In case of stereo-reproducing the sound, right and left two microphones are mounted.

Further, a display unit 129 is coupled on the left side surface of the main body case 110 rotatably for open and close through a hinge portion, which is not shown, and displays the image of the subject shot by the imaging unit 134. For example, the display unit 129 displays images during being shooting them and images when reproducing them. For the display unit 129, for example, a color liquid crystal display device of around 3 to 4 inches is used.

A circuit board 117 is provided on the inside of the main body case 110. A memory device 135 such as a recording medium and a media slot is mounted or attachable with respect to the circuit board 117, and records (stores) the image information of the subject and the sound information of the ambient sound of the subject, which are obtained by the normal mode or the special recording mode. On the circuit board 117, there are mounted the information-processing unit other than the memory device 135.

On the inside of main body case 110, a battery 114 is mounted other than the circuit board 117 and supplies DC power to the circuit board 117, the display unit 129, the imaging unit 134, the memory device 135 and the living-body sensor unit 145. Image and sound output terminals 139 or the like are provided on the external side of the main body case 110 and can be connected to connectors for image and sound, a communication cable or the like from an external apparatus. The image and sound output terminals 139 are used when executing image and sound output to the external apparatus and a terminal for the communication cable is used when communicating with the external apparatus.

The following will describe the living-body sensor unit 145. FIG. 2 shows a configuration of a perspiration sensor 145a that is applicable to the living-body sensor unit 145. The perspiration sensor 145a shown in FIG. 2 contains an air suction pipe 151, a housing 152 on the air suction side, a touch unit 153, a housing 154 on the air exhaust side, an air exhaust pipe 155, a compressor (blower) 156, absolute humidity sensors 157, 158 and a differential amplifier 159.

The air suction pipe 151 is connected to the air suction side of the touch unit 153 through the housing 152 and sucks the outside air (air) into the touch unit 153. The absolute humidity sensor 157 is provided at the housing 152 and detects the absolute humidity of the outside air sucked into the housing 152 to output the humidity detection signal S57 on the air suction side to the differential amplifier 159.

The touch unit 153 has a skin slide-touch surface and the skin slide-touch surface has two small holes. In the touch unit 153, the humidity uprises by the sweat of the operator 130 who touches the skin slide-touch surface. The touch unit 153 constitutes a capsule. The air exhaust pipe 155 is connected to the air exhaust side of the touch unit 153 through the housing 154 and exhausts the air taken-in to the touch unit 153 to the outside. The compressor 156 is connected at the end terminal portion of the air exhaust pipe 155 that sucks the outside air from the air suction pipe 151 and exhausts it to the outside.

The absolute humidity sensor 158 is provided at the housing 154 and detects the absolute humidity of the air passing through the housing 154 to output the humidity detection signal S58 on the air exhaust side to the differential amplifier 159. The differential amplifier 159 amplifies the difference between the humidity detection signal S57 on the air suction side and the humidity detection signal S58 on the air exhaust side and outputs a detection signal S45 of the amount of perspiration. Data obtained by analog/digital converting the detection signal S45 of the amount of perspiration is living-body information (hereinafter, referred to as emotion data D45). The living-body sensor unit 145 may contain such an analog/digital conversion function or the information-processing unit may contain such an analog/digital conversion function. When providing the living-body sensor unit 145 having such a configuration at a position used compatibly for the mode switch, it becomes possible to detect the amount of perspiration (hereinafter, referred to as "perspiration level Hx") of the operator 130 who touches the mode switch and output the emotion data D45 to the information-processing unit.

Figure 3:
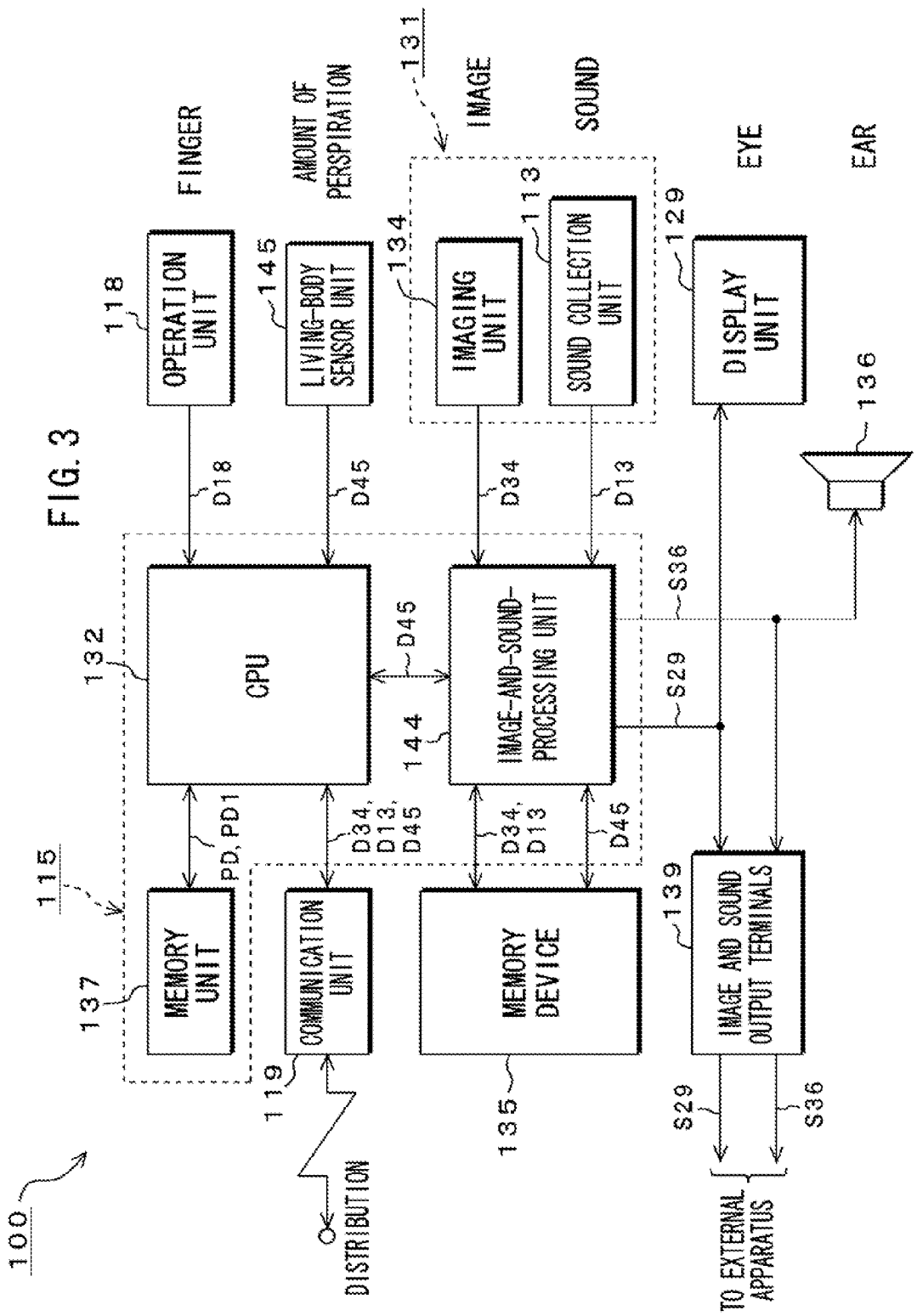
FIG. 3 is a block diagram showing a configuration of a control system of the video camera 100.

FIG. 3 shows a configuration of a control system of the video camera 100. The video camera 100 shown in FIG. 3 is constituted by being mounted with respective function blocks on the circuit board 117 in the main body case 110 shown in FIG. 1. It should be noted that in FIG. 3, portions corresponding to respective portions shown in FIGS. 1 and 2 are denoted as the same reference numerals.

The video camera 100 contains an information-processing unit 115, an operation unit 118, a communication unit 119, the display unit 129, an image-and-sound-recording unit 131, a memory device 135, the image and sound output terminals 139, and the living-body sensor unit 145.

The information-processing unit 115 contains a CPU 132, a memory unit 137 and an image-and-sound-processing unit 144. The CPU 132 controls the whole of video camera based on a system program. The memory unit 137 includes an ROM, an RAM, an EEPROM and the like which are not shown. In the ROM or the EEPROM of the memory unit 137, data PD forming the system program for controlling the whole of video camera is stored. The RAM, which is not shown, is used as a work memory. The CPU 132 reads the data PD forming the system program out of the ROM or the EEPROM concurrently with the power supply ON to expand it in the RAM and starts up the system to control the whole of the video camera.

In the ROM or the EEPROM of the memory unit 137, a program for executing the special recording mode other than the system program is described. The program for this special recording mode is a computer readable program which is used for moving-picture recording the information obtained by shooting the image of the subject and by collecting the ambient sound of the subject based on the emotion of the living-body of the operator 130. With respect the contents thereof, there are described a step of obtaining image information by shooting the image of the subject and also obtaining sound information by collecting the ambient sound of the subject; a step of detecting and producing living-body information showing emotion of living-body of an operator 130 who operates the image-and-sound-recording unit 131; and a step of performing processing to establish correspondence between the produced living-body information and the image information of the subject and/or the sound information of the ambient sound of the subject, which are shot and collected.

When data PD1 forming such a program is read out of the ROM or the EEPROM and is executed, the CPU 132 can execute the editing process or the like in which the correspondence between the produced emotion data D45 showing the emotion of the living-body of the operator 130 and the image information of the subject and/or the sound information of the ambient sound of the subject, which are shot and collected, is established if processing the information obtained by shooting the image of the subject and by collecting the ambient sound of the subject.

For example, the CPU 132 executes a process so as to establish the correspondence between the emotion data D45 outputted from the living-body sensor unit 145 and the image data D34 of the subject and/or the sound data D13 when recording the ambient sound of the subject, which are outputted from the image-and-sound-recording unit 131. In an embodiment, the CPU 132 compares the emotion data D45 outputted from the living-body sensor unit 145 with a threshold Hth for discriminating the amount of perspiration, which becomes a discrimination criterion of the emotion data D45. The threshold Hth for discriminating the amount of perspiration constitutes the discrimination criterion information.

Based on this comparison result, the CPU 132 controls the image-and-sound-processing unit 144 to execute the point setting control so that when, for example, the living-body sensor unit 145 detects the emotion data D45 of the perspiration level Hx exceeding the threshold Hth for discriminating the amount of perspiration, the image-and-sound-processing unit 144 adds editing start point information to the image data D34 of the subject and/or the sound data D13 when recording the ambient sound of the subject. Thereafter, when the living-body sensor unit 145 detects the emotion data D45 of the perspiration level Hx that is the threshold Hth for discriminating the amount of perspiration or less, the image-and-sound-processing unit 144 adds editing end point information to the image data D34 of the subject and/or the sound data D13 when recording the ambient sound of the subject.

The image-and-sound-processing unit 144 compresses the image data D34 in compliant with, for example, the MPEG-1 standard and records it on the memory device 135. According to the compression-process in compliant with the MPEG-1 standard, data of only moving portions in the image is detected and compressed so as to be saved. The compression-process is not limited to MPEG-1 and it is also allowed to employ each of the standards from MPEG-2 to MPEG-4 with high-definition television correspondence or the MPEG-7 standard which is presently in process of standardization.

In an embodiment, the memory unit 137 stores the threshold Hth for discriminating the amount of perspiration. For example, the threshold Hth for discriminating the amount of perspiration is stored as a trigger parameter beforehand in a ROM or the like provided in the memory unit 137. The RAM of the memory unit 137 receives the emotion data D45 under the memory control of the CPU 132, compares the preset threshold Hth for discriminating the amount of perspiration with the perspiration level H obtained from the emotion data D45, and executes a discrimination process of Hth>H and a discrimination process of Hth<H or the like. It is needless to say that the threshold of discriminating the amount of perspiration is not limited to an unambiguous constant and it is also allowed to employ a variable which changes in a second order function (see FIG. 5).

By doing in this manner, it becomes possible to extract specific image and sound corresponding to the amount of perspiration of the finger of the operator 130. The editing start point information and the editing end point information are, for example, set (described) as time codes with respect to the recording time information. By setting these time codes, it becomes possible to automatically extract the image data D34 and the sound data D13 at a period of time when emotion of the living-body is heightened to sweat in a hand during the operator 130 is shooting the image of the subject.

In an embodiment, the CPU 132 controls the image-and-sound-processing unit 144 to execute an editing process by extracting the image data D34 and the sound data D13 in a period of time from a point of time when the editing start point information is added to a point of time when the editing end point information is added from the image data D34 of the subject and the sound data D13 when recording the ambient sound of the subject based on the editing start point information and the editing end point information and splicing the extracted items of the data. When executing such an editing process, it is possible to extract the image data D34 and the sound data D13 at a period of time when emotion of the living-body is heightened to sweat in a hand during the time when the operator 130 is shooting the image of the subject from the image data D34 obtained by shooting the image of the subject with the operator 130 and the sound data D13 obtained by collecting the ambient sound of the subject, thereby enabling the operator's specific image and sound data files to be produced.

Further, it is also allowed, by making the CPU 132 possess a reproduction control function, to reproduce the image data D34 of the subject and the sound data D13 when recording the ambient sound of the subject, which are extracted and spliced based on the editing process. When executing such a reproducing process, it is possible to reproduce the image data D34 and the sound data D13 at a period of time when emotion of the living-body is heightened to sweat in a hand during the time when the operator 130 is shooting the image of the subject and it becomes possible to view a memorial file in which the operator's specific image data D34 and sound data D13 are recorded. The display unit 129 receives the operator's specific image data D34 to display the operator's specific image, and the speaker 36 receives the operator's specific sound data D13 to output the operator's specific sound therefrom.

Further, it is also allowed, by making the CPU 132 possess a record control function, to record the image data D34 of the subject and the sound data D13 when recording the ambient sound of the subject, which are extracted and spliced based on the editing process, onto a predetermined recording medium. When executing such a moving picture recording process, it is possible to record the image data D34 and the sound data D13 at a period of time when emotion of the living-body is heightened to sweat in a hand during the time when the operator 130 is shooting the image of the subject onto a recording medium of a CD-ROM, a MD or the like, thereby enabling a memorial file in which the operator's specific image data D34 and sound data D13 are recorded to be distributed.

The operation unit 118 is connected to the CPU 132 and outputs operation data D18 generated by pushing down the push-button switches 112 such as the power supply switch, the mode switch, the zoom switch or the shooting start/stop switch shown in FIG. 1 to the CPU 132.

The image-and-sound-recording unit 131 contains the sound collection unit 113 and the imaging unit 134. The sound collection unit 113 is connected to the image-and-sound-processing unit 144 and outputs the sound data D13 obtained by collecting the ambient sound of the subject. For the sound collection unit 113, a condenser type microphone or a moving coil type microphone is used. The imaging unit 134 is connected to the image-and-sound-processing unit 144 and outputs the image data D34 obtained by shooting the image of the subject. The imaging unit 134 is constituted by an imaging lens, an image pickup device and a lens drive mechanism.

The living-body sensor unit 145 constitutes the information output unit and detects the living-body information showing emotion of the living-body of the operator 130 who operates the image-and-sound-recording unit 131 to output the emotion data D45. For example, for the living-body sensor unit 145, the perspiration sensor 145a shown in FIG. 2 is used and detects the amount of perspiration of the operator 130 who operates the image-and-sound-recording unit 131 on time series to output the emotion data D45 to the CPU 132.

The memory device 135 constituting a recording medium, a media slot or the like is connected to the above-mentioned CPU 132 and on an occasion of a special recording mode, stores record information which establishes the correspondence between the emotion data D45 produced by detecting the living-body information showing emotion of the living-body of the operator 130 and the image data D34 of the subject and/or the sound data D13 when recording the ambient sound of the subject, which are shot and collected. For the memory device 135, a hard disk device or a non volatile memory such as a memory card and the like is used.

The display unit 129 is connected to the above-mentioned image-and-sound-processing unit 144 and displays the images when being shooting them and images when reproducing them based on an image display signal S29. The speaker 136 is connected to the image-and-sound-processing unit 144 and outputs the ambient sound of the subject when being shooting the images and the sound when reproducing the images or the like based on a sound signal S36. The speaker 136 is provided at a predetermined position of the main body case 110. The image and sound output terminals 139 are connected to the image-and-sound-processing unit 144 and outputs the image and sound signals to an external apparatus.

The communication unit 119 is connected to the CPU 132 and communicates to the external apparatus. For example, the CPU 132 controls the communication unit 119 to distribute the image data D34 of the subject and the sound data D13 when recording the ambient sound of the subject, which are extracted and spliced based on the editing process. When executing such a distributing process, it is possible to distribute the image data D34 and the sound data D13 at a period of time when emotion of the living-body is heightened to sweat in a hand during the time when the operator 130 is shooting the image of the subject, thereby enabling a file (algorithm) recorded with the operator's specific image data D34 and sound data D13 to be downloaded to other users through the Internet or the like.

FIGS. 4A to 4D and FIGS. 5A to 5D show shooting format examples (No. 1, No. 2 thereof) in the video camera 100. The shooting format examples show insertion examples of the start point and the end point at the time of recording. In an embodiment, it is constituted such that specific image and sound can be extracted corresponding to the amount of perspiration of the finger of the operator 130 and at the same time, the editing start point information and the editing end point information are to be set (described) as time codes with respect to the recording time information.

Figure 4:
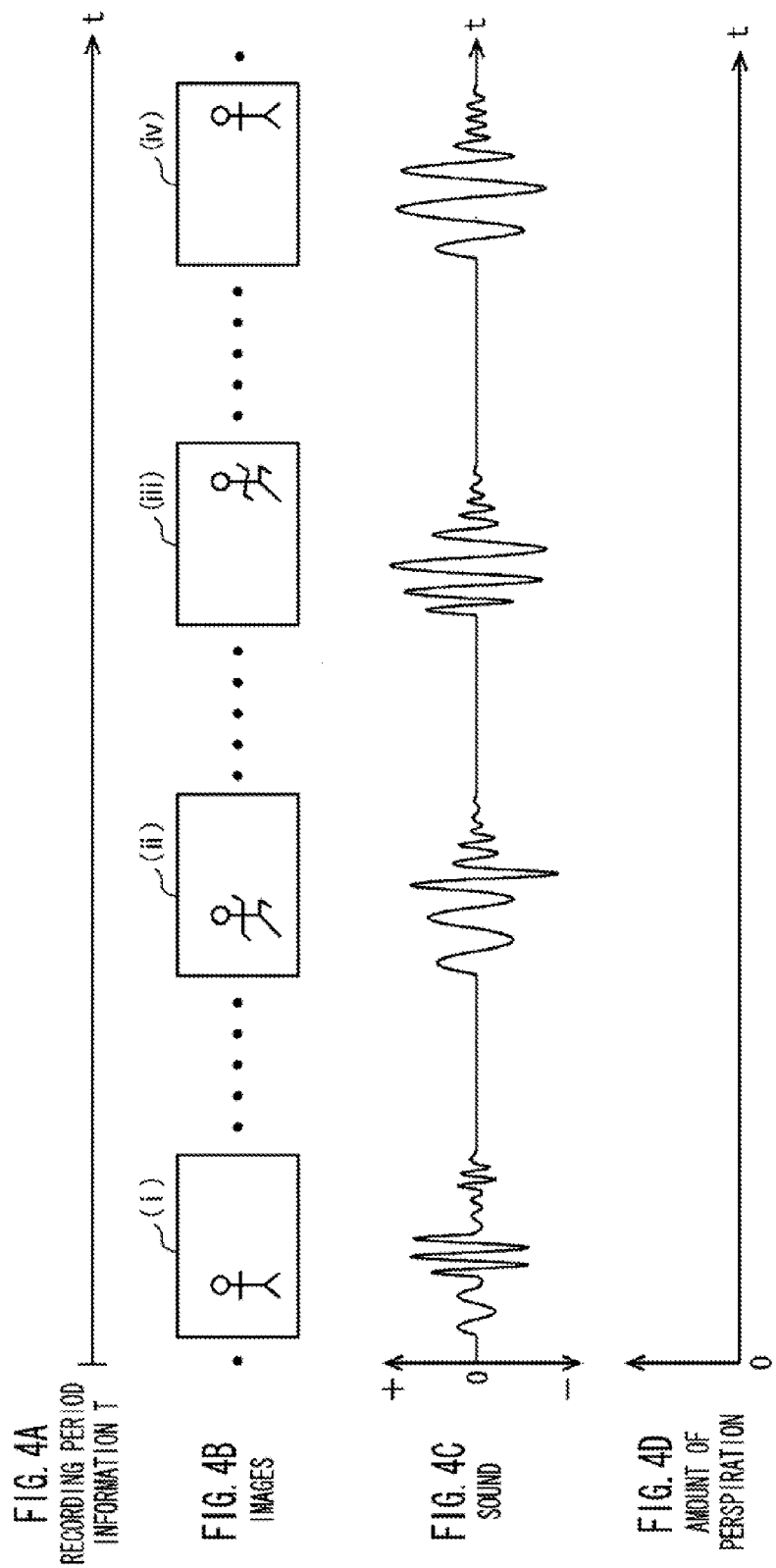
FIGS. 4A through 4D are time charts showing a shooting format example (No. 1 thereof) in the video camera 100.

FIG. 4A and FIG. 5A show the recording period information T. The recording period information T means a period of time when the start switch is pushed down and the image data D34 is taken in and recorded on the memory device 135. The moving picture scenes shown in FIG. 4B and FIG. 5B are eight scenes (i) to (viii) representing the subject movements. Sampling frequency of the moving picture scene is 1/30 sec. More specifically, the imaging unit 134 obtains images of 30 frames for every one second (according to NTSC system). In an embodiment, there is dealt with a case in which the operator 130 is shooting images of a subject who is attending the "foot race" in an athletic meet.

The scene (i) shown in FIG. 4B is an image when the subject is waiting for his race. The scenes (ii) and (iii) are images when his turn has come finally and the subject moves to the start line. The scene (iv) is an image when the subject stands at the start line. Further, the scene (v) shown in FIG. 5B is an image at the instant when a starter fires a signal gun. The scene (vi) is an image when the subject starts running. The scene (vii) is an image of a state in which the subject fall down caused by his excess energy. The scene (viii) is an image when the subject reaches the goal while crying.

The waveform shown in FIG. 4C denotes a sound signal when recording the ambient sound of the subject. The sound collection unit 113 records the ambient sound of the subject. In an embodiment, ambient sound of the subject who is attending the "foot race" of the athletic meet is recorded. For example, with respect to the sound information corresponding to the scenes (i) to (iv), a march and an ambient noise sounds which are specific to an athletic meet are recorded. Further, with respect to the sound information corresponding to the scene (v) shown in FIG. 5C, there are recorded the "blam" sound and the like at the instant when the starter fires the signal gun and at the same time, cheering sounds by cheering persons corresponding to the scene (vi) are recorded. For the sound information corresponding to the scene (vii), for example, such a cheer as "Now, get up and keep on!" with respect to the subject is recorded. For the sound information corresponding to the scene (viii), for example, a commotion of relief with respect to the activity that the subject finishes the race is recorded.

FIG. 4D denotes time-lapse change of the amount of perspiration of the operator who shoots the subject with holding the video camera 100. In an embodiment, it is shown that there is little amount of perspiration corresponding to the scenes (i) to (iv). However, in the scene (v) shown in FIG. 5D, immediately after the subject stands at the start line, the amount of perspiration of the operator begins to increase and at the instant when the starter fires a signal gun, for example, the peak thereof has come. In the scene (vi), from a point of time when the subject begins to run, the amount of perspiration of the operator also begins to decrease gradually. However, in the scene (vii), when the subject falls down caused by his excess energy, the amount of perspiration of the operator begins to increase again and at the instant when the subject stands up, for example, the peak thereof has come. Then, the amount of perspiration of the operator also begins to decrease gradually. In an embodiment, in the scene (viii), at the point of time when the subject finishes the race while crying, the amount of perspiration of the operator returned to the same state as that of the beginning.

It is known that the amount of his perspiration increases with respect to the emotion change of such an operator and the amount of perspiration thereof becomes less depending on the elapse of time. Such a perspiration phenomenon is called as an emotional perspiration. It is known that the emotional perspiration occurs at the skin of a palm, a foot bottom portion or the like when a person is impressed, is excited or gets nervous. The amount of perspiration thereof is less compared with thermal perspiration and the perspiration latent time thereof is also shorter. Sweat glands are eccrine glands. Also, it is also known with respect to the emotional perspiration that the amount of perspiration lowers in a quadratic-like function caused by repetition of impression or the like (posture reaction).

It should be noted that according to an academic document [The Society of Instrument and Control Engineers Tohoku-Chapter, 197th Research Meeting (Oct. 13, 2001) Document No. 197-11] which explains the relation between the perspiration and the emotion change, the perspiration reaction at the palm portion appears significantly in a group of trial subjects in an unstable psychology-mood state as compared with a group in a stable state. In case of applying repeated load on a trial subject, it is reported that the first perspiration reaction is significant in a stable psychology-mood state and the decrease in the amount of reaction caused by a familiarization effect is also significant. In addition, it is also reported that a personal psychology-mood characteristic easily affects on the posture reaction and the familiarization effect thereof and the influence of the posture reaction should be considered in the quantitative evaluation of the palm portion perspiration. The palm portion perspiration is promoted by an affect change or a memory recall accompanied by an emotional reaction. It is concluded that the palm portion perspiration can be an objective index of a human spirit-psychology process.

Consequently, when judging the small or large amount of perspiration with respect to the emotion change of the operator, a threshold Hth for discriminating the amount of perspiration may be set, which becomes a constant value with respect to the elapsed time, but in an embodiment as shown in FIG. 5D, a threshold curved line of discriminating the amount of perspiration is set, which changes in a quadratic-like function with respect to the elapse time. For the threshold curved line of discriminating the amount of perspiration, for example, A (1/log (n)) is used. A letter, "A" is a constant and is a threshold having a unit corresponding to the time change of the amount of perspiration. The following formula (1) is discriminated:

$$Hx > Hth = A(1/\log(n)) \quad (1)$$

where the amount of perspiration of the operator at a certain point of time is assumed to Hx, so that the large or small amount of perspiration with respect to the emotion change of the operator is discriminated.

In an embodiment, the threshold curved line of discriminating the amount of perspiration is a curved line in which a period of monitoring time is related to the threshold. The period of monitoring time is variable. For example, it is possible for the period of monitoring time to be set freely as five minutes, ten minutes, fifteen minutes and so on. With respect to the setting condition for the threshold curved line of discriminating the amount of perspiration, the change rate (emotion change rate) of the amount of perspiration of the operator, which is detected by the living-body sensor unit 145, is compared with a reference change rate which becomes a setting reference of the preset threshold curved line and when the change rate of the amount of perspiration of the operator exceeds the reference change rate, the threshold curved line of discriminating the amount of perspiration is set.

The change rate of the amount of perspiration of the operator is obtained by performing an arithmetical operation of a difference value between the amounts of perspiration detected at two points of sampling time on and after the point of time when the living-body sensor unit 145 detects some sort of amount of perspiration of the operator. In an embodiment, when the emotion change of the operator is large, inclination of the detection curve of the amount of perspiration becomes large and when the emotion change thereof is small, inclination of the detection curve of the amount of perspiration becomes small. Consequently, the above-mentioned difference value is obtained and when the change rate of the amount of perspiration of the operator exceeds the reference change rate, the threshold curved line of discriminating the amount of perspiration is set. More specifically, the threshold curved line of discriminating the amount of perspiration is set at a point of time when the emotion change rate of the operator exceeds the reference change rate and has a characteristic of effectively working only for a predetermined period of monitoring time from the set point of time. The above-mentioned process repeats again when this monitoring period of time elapses. This is because a case is assumed where the amount of perspiration in which the emotion change rate of the operator again becomes large is detected.

In an embodiment, the threshold curved line of discriminating the amount of perspiration is set at a point of time t0, in the recording time information T, when the rising (change rate) of the amount of perspiration becomes large. In the scene (v) shown in FIG. 5D, the perspiration level Hx of the operator exceeds the threshold Hth1 of discriminating the amount of perspiration. The point of time ts when this perspiration level Hx exceeds the threshold Hth1 for discriminating the amount of perspiration forms a first time code and at the same time, is the editing start point information when editing the moving picture scenes.

Further, time elapses and in the scene (vi) shown in FIG. 5D, the perspiration level Hx of the operator becomes lower than the threshold Hth2 for discriminating the amount of perspiration. The point of time te when this perspiration level Hx becomes lower than the threshold Hth2 for discriminating the amount of perspiration forms the first time code and at the same time, is the editing end point information when editing the moving picture scene. The moving picture scene between the point of time ts and the point of time te relating to these first time codes becomes a first extraction (picking) scene Sv (image and sound information for edition) in the special recording mode.

In an embodiment, time elapses further and in the scene (vii) shown in FIG. 5D, the perspiration level Hx of the operator exceeds the threshold Hth3 for discriminating the amount of perspiration. The point of time ts when this perspiration level Hx exceeds the threshold Hth3 for discriminating the amount of perspiration forms a second time code and at the same time, is the editing start point information when editing the moving picture scenes. Further, time elapses and in the scene (vii) shown in FIG. 5D, the perspiration level Hx of the operator becomes lower than the threshold Hth4 for discriminating the amount of perspiration. The point of time te when this perspiration level Hx becomes lower than the threshold Hth4 for discriminating the amount of perspiration forms the second time code and at the same time, is the editing end point information when editing the moving picture scenes. The moving picture scene between the point of time ts and the point of time te relating to these second time codes becomes a second extraction (picking) scene SVii (image and sound information for edition) in the special recording mode.

Figure 6:
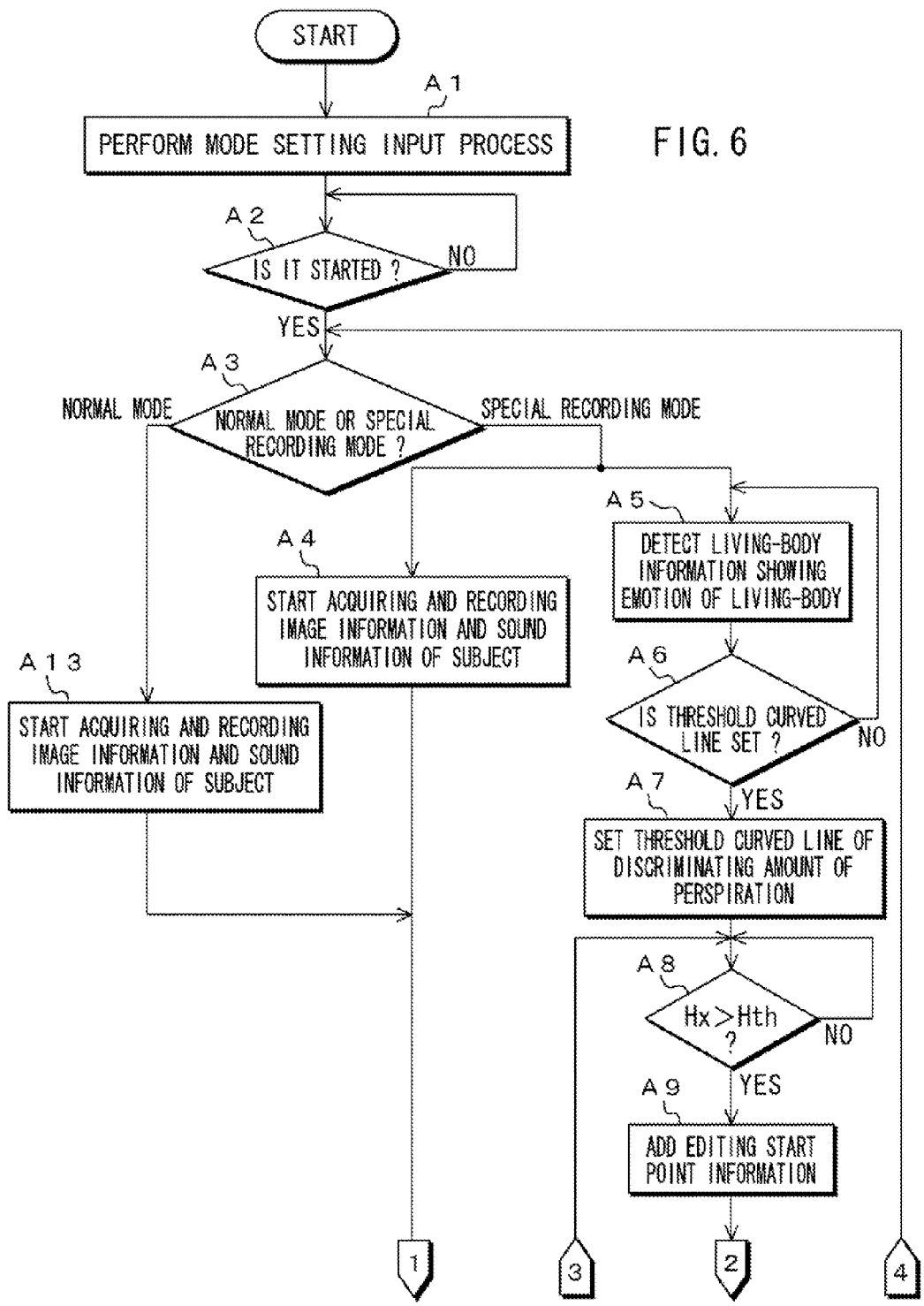
FIG. 6 is a flowchart showing a recording process example (No. 1 thereof) in the video camera 100.
Figure 7:
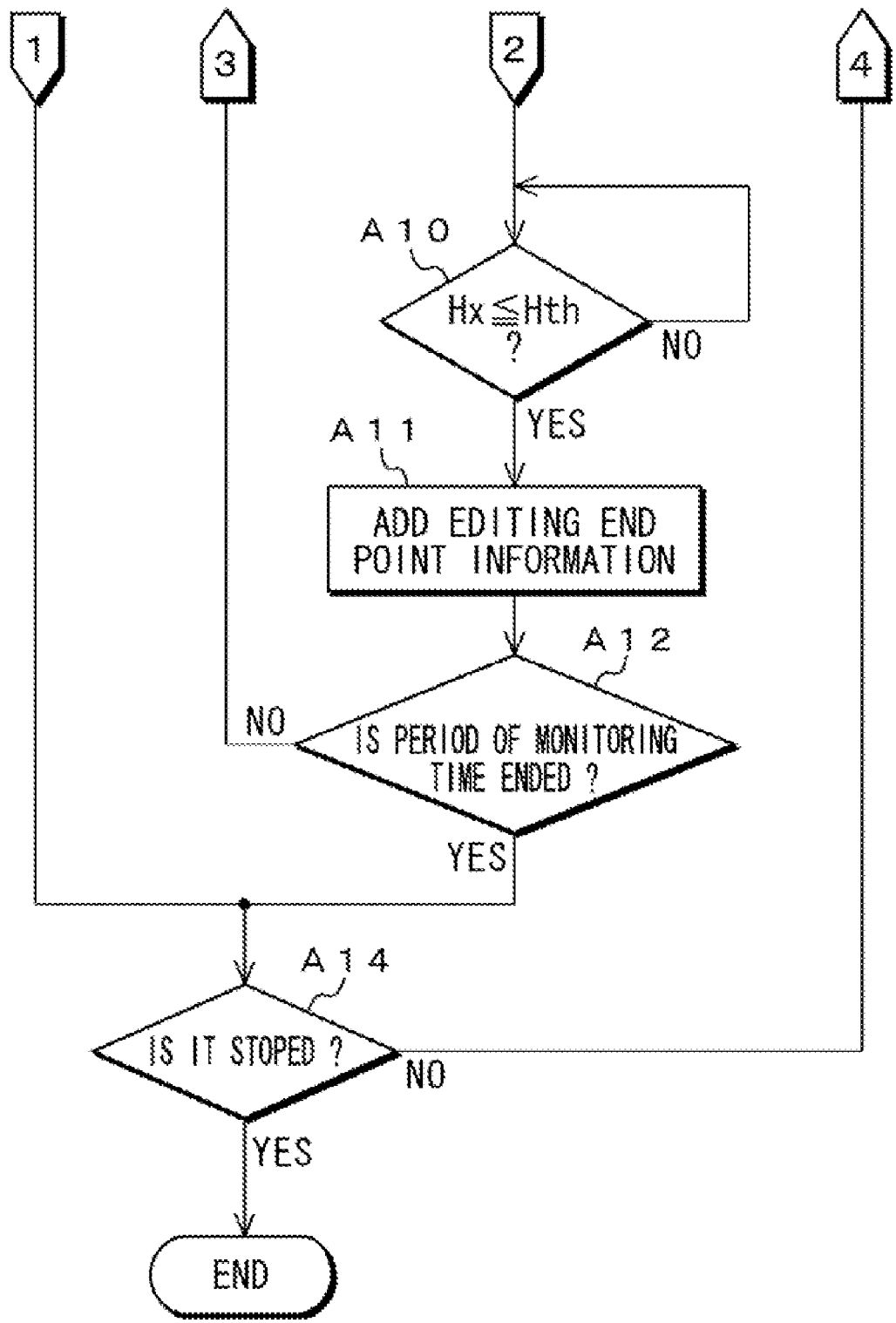
FIG. 7 is a flowchart showing a recording process example (No. 2 thereof) in the video camera 100.

The following will describe an embodiment of a first information-processing method. FIGS. 6 and 7 show information-recording examples (No. 1, No. 2 thereof) in the video camera 100.

In an embodiment, a case is assumed in which the information obtained by shooting the image of the subject and by collecting the ambient sound of the subject is processed. For the living-body sensor unit 145, the perspiration sensor 145a as shown in FIG. 2 is used. The CPU 132 executes a process so as to establish the correspondence between the emotion data D45 outputted from the living-body sensor unit 145 and the image data D34 of the subject and/or the sound data D13 when recording the ambient sound of the subject, which are outputted from the image-and-sound-recording unit 131.

On the premise of these, the CPU 132 executes a mode setting input process in step A1 of the flowchart shown in FIG. 6. For example, operation data D18 relating to the setting of the normal mode or the special recording mode is inputted. At that time, the user operates a push-button switch 112 constituting a mode switch to select either one of the normal mode and the special recording mode. For example, when he or she operates the push-button switch 112 to select the special recording mode, the operation unit 118 outputs the operation data D18 showing the special recording mode to the CPU 132.

Next, in step A2, the CPU 132 waits for the start. At that time, the user operates the push-button switch 112 constituting a shooting start switch to instruct a start of the moving picture recording process to the CPU 132. The operation unit 118 outputs the operation data D18 instructing the start of the moving picture recording process to the CPU 132.

When the operation unit 118 instructs the start of the moving picture recording process to the CPU 132, the process is branched by setting the normal mode or the special recording mode in step A3. If the special recording mode is set in the step A1, the CPU 132 controls the image-and-sound-recording unit 131, in step A4, so as to acquire information on the image of the subject and the ambient sound of the subject and the process is shifted to the recording start processing. At that time, the image-and-sound-recording unit 131 obtains the image data D34 by shooting the image of the subject and also, obtains the sound data D13 by collecting the ambient sound of the subject. The image-and-sound-processing unit 144 records on the memory device 135 the image data D34 in which only the moving portion in the image is detected and compressed, for example, in compliant with the MPEG-1 standard.

In parallel with this, in step A5, the CPU 132 controls the living-body sensor unit 145 to detect the living-body information showing emotion of the living-body of the operator 130 who operates the video camera 100 and produce the emotion data D45. The living-body sensor unit 145, under this control, detects the amount of perspiration of the operator touching the mode switch and outputs the emotion data D45 showing the perspiration level to the CPU 132.

Next, in step A6, the CPU 132 judges whether or not the threshold curved line of discriminating the amount of perspiration is set. With respect to the criterion of judgment in this case, it is executed by comparing the change rate (emotion change rate) of the amount of perspiration of the operator, which is detected by the living-body sensor unit 145, with a reference change rate which becomes a setting reference of the preset threshold curved line. The change rate of the amount of perspiration of the operator is a difference between the amounts of perspiration detected at two points of sampling time on and after the point of time when the living-body sensor unit 145 detects some sort of amount of perspiration of the operator. The reason for obtaining such a difference is because the inclination of the detection curve of the amount of perspiration becomes large when the emotion change of the operator is large and the inclination of the detection curve of the amount of perspiration becomes small when the emotion change thereof is small.

Figure 5:
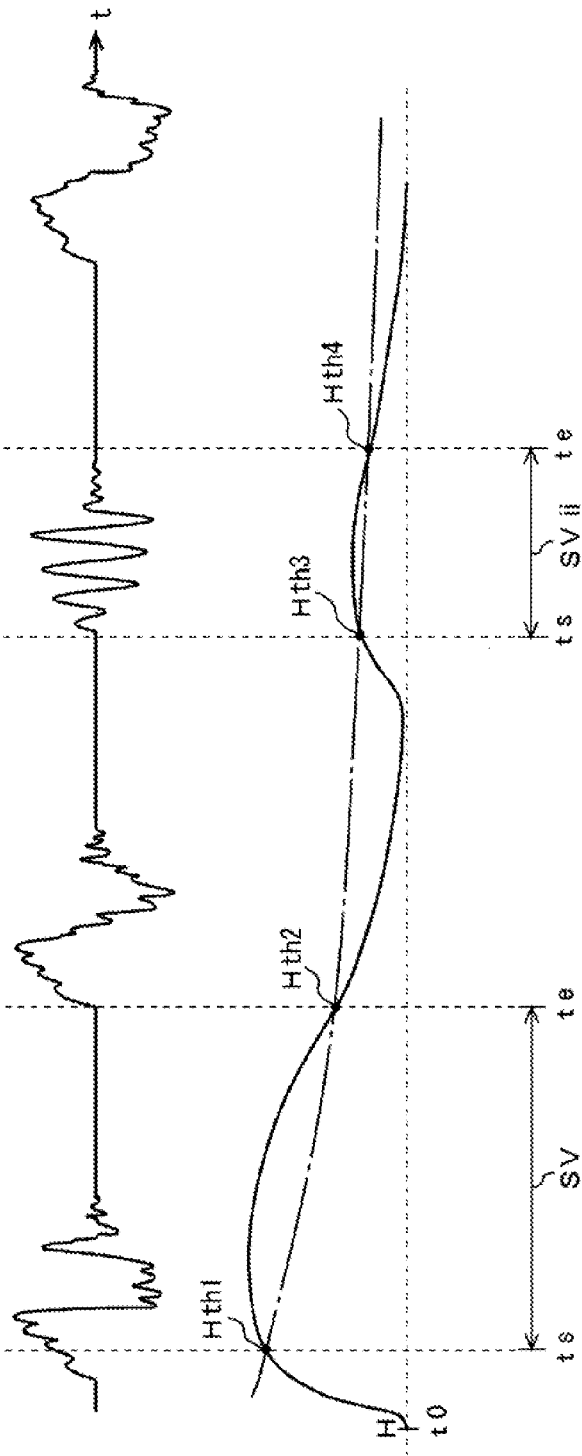
FIGS. 5A through 5D are time charts showing the shooting format example (No. 2 thereof) in the video camera 100.

In the step A6, when the change rate of the amount of perspiration of the operator exceeds the reference change rate, the CPU 132 set the threshold curved line of discriminating the amount of perspiration in step A7. At that time, the threshold curved line of discriminating the amount of perspiration as shown in the formula (1) is read out of the memory unit 137 and is expanded in the RAM. Concurrently with this, the CPU 132 activates a timer and starts the count of the period of monitoring time. Then, the process shifts to step A8 where the CPU 132 executes a discrimination process of Hx>Hth by comparing the emotion data D45 outputted from the living-body sensor unit 145 and the threshold Hth for discriminating the amount of perspiration which becomes the discrimination criterion of the emotion data D45. The memory unit 137, as shown in FIG. 5, receives the emotion data D45 under the memory control of the CPU 132 and the thresholds Hth1, Hth2, Hth3, Hth4 and so on of discriminating the amount of perspiration, which form preset threshold curved lines of discriminating the amount of perspiration, are compared with the perspiration level Hx obtained from the emotion data D45.

When the discrimination result such as Hx>Hth is obtained, the process shifts to step A9 where the CPU 132 adds editing start point information with respect to the image data D34 of the subject and the sound data D13 when recording the ambient sound of the subject, which are stored by simultaneous proceedings in the memory device 135 in the step A4. At that time, according to the example of the scene (v) shown in FIG. 5, the living-body sensor unit 145 detects the emotion data D45 of the perspiration level Hx exceeding the threshold Hth1 of discriminating the amount of perspiration, so that the CPU 132 adds the editing start point information to the image data D34 of the subject and to the sound data D13 when recording the ambient sound of the subject. In the image-and-sound-processing unit 144, by the editing start point information adding control (point-setting control) from the CPU 132, the point of time ts is marked (described) as a time code in the recording time information T.

Then, the process shifts to step A10 shown in FIG. 7 where the CPU 132 executes a discrimination process of Hx≦Hth. In case of discriminating Hx≦Hth, the process shifts to step A11 where the editing end point information is added with respect to the image data D34 of the subject and the sound data D13 when recording the ambient sound of the subject, which are stored by simultaneous proceedings in the memory device 135 in the step A4. At that time, according to the example of the scene (v) shown in FIG. 5, the living-body sensor unit 145 detects the emotion data D45 of the perspiration level Hx which becomes lower than the threshold Hth2 of discriminating the amount of perspiration, so that the CPU 132 controls the image-and-sound-processing unit 144 to execute the point setting control so as to add the editing end point information to the image data D34 of the subject and the sound data D13 when recording the ambient sound of the subject.

In the image-and-sound-processing unit 144, by the editing end point information adding control (point setting control) from the CPU 132, the point of time te is marked (described) as a time code in the recording time information T. The moving picture scene between the point of time ts and the point of time te relating to these time codes becomes a first extraction (picking) scene Sv (image and sound information for edition) in the special recording mode (see FIG. 5). In the image-and-sound-processing unit 144, the point of time ts and the point of time te are marked (described) as time codes in the recording time information T. The moving picture scene between the point of time ts and the point of time te for these time codes becomes a first extracted (picking) scene Sv (image and sound information for edition) in the special recording mode (see FIG. 5).

Thereafter, the process shifts to step A12 where it is judged whether or not the period of monitoring time in the threshold curved line of discriminating the amount of perspiration is ended. With respect to the judgment criterion in this case, it is ended by the counting-up of the timer. When the monitoring period of time is not ended, the process returns to the step A8 where the CPU 132 executes a discrimination process of Hx>Hth by comparing the emotion data D45 outputted from the living-body sensor unit 145 and the threshold Hth of discriminating the amount of perspiration which becomes the discrimination criterion of the emotion data D45.

According to the example shown in FIGS. 4A through 4D and FIGS. 5A through 5D, the time codes ts, te which can edit the first and second extracted scenes are added. Thus, it becomes possible to extract a specific image and sound corresponding to the amount of perspiration of the finger of the operator 130. The editing start point information and the editing end point information are, for example, set (described) as time codes with respect to the recording time information. By setting these time codes, it becomes possible to automatically extract the image data D34 and the sound data D13 at the period of time when emotion of the living-body is heightened to sweat in a hand during the time when the operator 130 is shooting the image of the subject. When the above-mentioned period of monitoring time is ended, the process shifts to step A14.

It should be noted that when the normal mode is set in the step A3, the process shifts to the step A13 where the normal mode is executed. In the normal mode, the editing end point information, the editing end point information or the like is not added and the image data D34 of the subject and the sound data D13 when recording the ambient sound of the subject are stored on the memory device 135. Thereafter, the process shifts to the step A14.

In the step A14, the CPU 132 executes ending judgment. For example, it is judged whether or not a push-button switch 12 constituting a shooting stop switch is operated. Alternatively, it is judged whether or not power-off information is detected. When the push-button switch 12 constituting the shooting stop switch is operated or when the power-off information is detected, the moving picture recording process is ended. When the push-button switch 12 constituting the shooting stop switch is not operated and when the power-off information is not detected, the process returns to the step A3 where the above-mentioned processes are repeated. Thus, it becomes possible to execute a moving picture recording process so as to store on the memory device 135 the emotion data D45 obtained from the living-body sensor unit 145, the image data D34 of the subject, and the sound data D13 when recording the ambient sound of the subject, which are shot and collected, with establishing correspondence between the emotion data D45 and the image data D34 and/or the sound data D13.

In this manner, according to the embodiments of the video camera and the first information-processing method, in case of processing information obtained by shooting the image of the subject and by collecting the ambient sound of the subject, the image-and-sound-recording unit 131 shoots the image of the subject to output the image data D34 and also, collects the ambient sound of the subject to output the sound data D13. The living-body sensor unit 145 detects the living-body information showing emotion of the operator 130 who operates the image-and-sound-recording unit 131 to output the emotion data D45. On the premise of this, the CPU 132 executes a process so as to establish the correspondence between the emotion data D45 outputted from the living-body sensor unit 145 and the image data D34 of the subject and/or the sound data D13 when recording the ambient sound of the subject, which are outputted from the image-and-sound-recording unit 131.

Consequently, it is possible to automatically extract the image data D34 and the sound data D13 at the period of time when emotion of the living-body is heightened to sweat in a hand during the time when the operator is shooting the image of the subject, thereby enabling the operator's specific image and sound data file, which is obtained by editing the image data D34 and the sound data D13 extracted automatically here, to be easily and simply produced. Thus, it becomes possible to improve editing work dramatically as compared with a case in which an editing start point, an editing end point or the like is appointed and inputted by a manual operation on the way of shooting the image of the subject.

Figure 8:
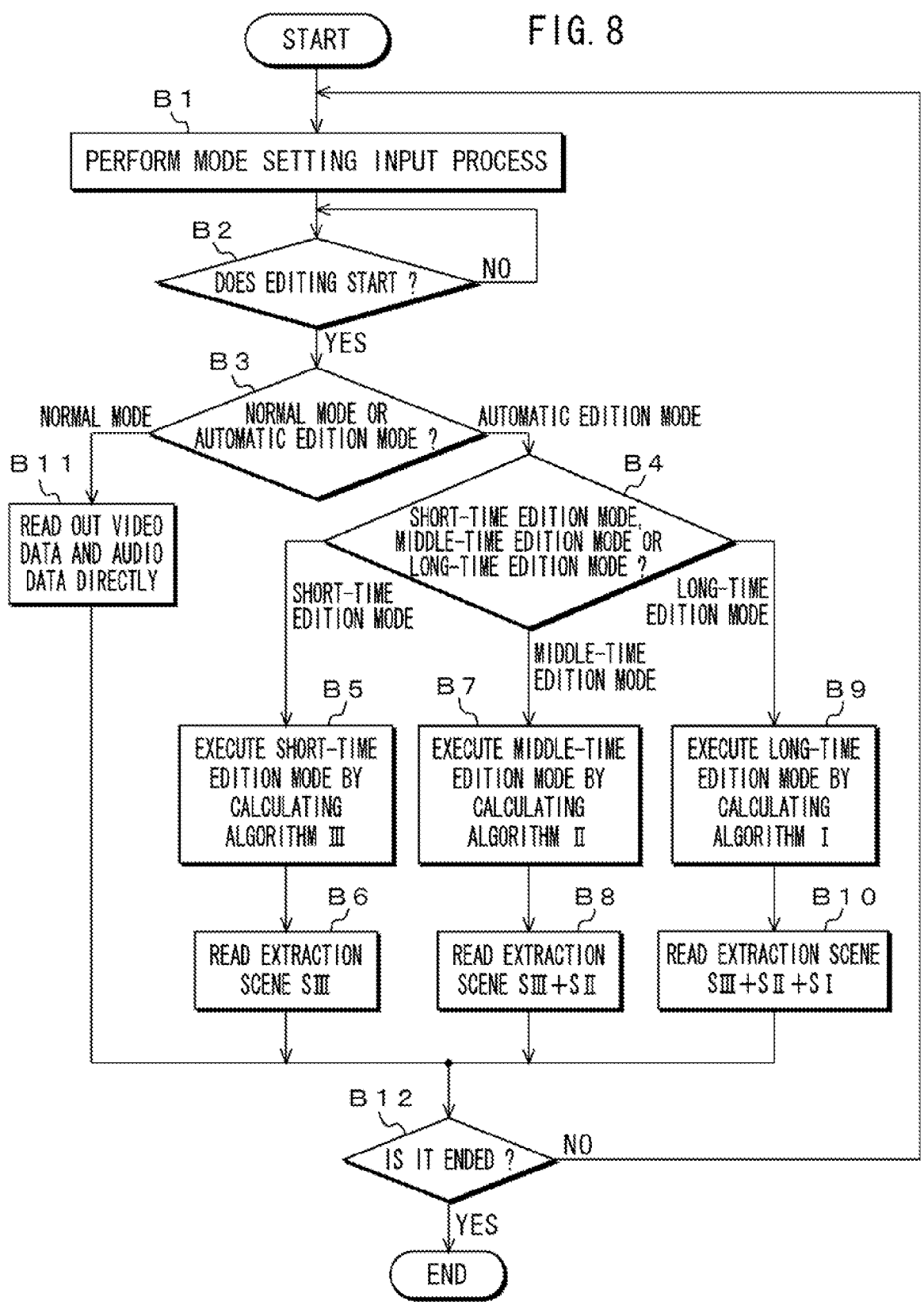
FIG. 8 is a flowchart showing an information edition example in the video camera 100.

The following will describe an information edition example in the video camera 100. FIG. 8 shows an information edition example in the video camera 100. In an embodiment, the information editing process is provided with a normal mode or an automatic edition mode. When the automatic edition mode is selected, the image data D34 and the sound data D13 in a period of time from a point of time when editing start point information is added to a point of time when editing end point information is added are extracted and spliced from the image data D34 of the subject and the sound data D13 when recording the ambient sound of the subject. With respect to the automatic edition mode, a case in which three kinds of modes such as a short-time edition mode, a middle-time edition mode and a long-time edition mode are prepared is cited.

By making these as the editing process condition, the CPU 132 executes a mode setting input process in step B1 of the flowchart shown in FIG. 8. For example, operation data D18 relating to the setting of the normal mode or the automatic edition mode is inputted. At that time, the user operates the push-button switch 112 constituting the mode switch to select either one of the normal mode and the automatic edition mode. For example, when he or she operates the push-button switch 112 to select the automatic edition mode, the operation unit 18 outputs the operation data D18 showing the automatic edition mode to the CPU 132. Further, when selecting the automatic edition mode, it is constituted such that there can be selected one mode among the short-time edition mode, the middle-time edition mode and the long-time edition mode.

Here, the short-time edition mode is referred to as a mode in which the image data D34 and the sound data D13 of the shortest one period of time from a point of time when the editing start point information is added to a point of time when the editing end point information is added are extracted from a plurality of periods of time from a point of time when the editing start point information is added to a point of time when the editing end point information is added. The middle-time edition mode is referred to as a mode in which the image data D34 and the sound data D13 of other periods of time than the period of time extracted by the short-time edition mode are spliced. The long-time edition mode is referred to as a mode in which the short-time edition mode and the middle-time edition mode are combined, for example, all of the image data D34 and the sound data D13 of the periods of time from a point of time when the editing start point information is added to a point of time when the editing end point information is added are spliced.

Next, in step B2, the CPU 132 waits for the editing start. At that time, the user operates the push-button switch 112 constituting an editing start switch to instruct a start of the editing process to the CPU 132. The operation unit 118 outputs the operation data D18 instructing the start of the editing process to the CPU 132.

When the operation unit 118 instructs the editing process start to the CPU 132, in step B3, the process is branched by setting the normal mode or the automatic edition mode. When the automatic edition mode is set in the above-mentioned step B1, the process shifts to step B4 where the CPU 132 further branches the control based on the setting of the short-time edition mode, the middle-time edition mode or the long-time edition mode.

When the short-time edition mode is set in the above-mentioned step B1, the process shifts from the step B4 to step B5 where the CPU 132 executes the short-time edition mode by calculating algorithm III. Here, the time codes ts, te are detected from the recording time information T, and the arithmetic calculation for extracting the image data D34 and the sound data D13 of the period of time when the time codes ts, te are added from the image data D34 and the sound data D13 is assumed to be "f" and the extracted scene edited by calculating the algorithm III is assumed to be "f (SIII)".

In step B6, the CPU 132 reads the image data D34 and the sound data D13 relating to the extracted scene f (SIII) out of the memory device 135. When reproducing the image data D34 and the sound data D13 relating to the extracted scene f(SIII) read out of the memory device 135, it is possible to reproduce the image data D34 and the sound data D13 at the period of time when emotion of the living-body is heightened to sweat in a hand during the time when the operator 130 is shooting the image of the subject, thereby enabling the memorial file in which the operator's specific image data D34 and sound data D13 are recorded to be viewed. Thereafter, the process shifts to step B12.

Also, when the middle-time edition mode is set in the above-mentioned step B1, the process shifts from the step B4 to step B7 where the CPU 132 executes the middle-time edition mode by calculating algorithm II. At that time, the extracted scene edited by calculating the algorithm II is assumed to be "f(SIII+SII)".

The CPU 132 reads the image data D34 and the sound data D13 relating to the extracted scene f(SIII+SII) out of the memory device 135 in step B8. When reproducing the image data D34 and the sound data D13 relating to the extracted scene f(SIII+SII) read out of the memory device 135, it is possible to reproduce the image data D34, the sound data D13 and the like at the period of time when emotion of the living-body is heightened to sweat in a hand during the time when the operator 130 is shooting the image of the subject and at the period of time when the emotion of the living-body is next heightened to sweat in a hand, thereby enabling the memorial file in which the operator's specific image data D34 and sound data D13 are recorded to be viewed. Thereafter, the process shifts to step B12.

Further, when the long-time edition mode is set in the above-mentioned step B1, the process shifts from the step B4 to step B9 where the CPU 132 executes the long-time edition mode by calculating algorithm I. At that time, the extracted scene edited by calculating the algorithm I is assumed to be "f(SIII+SII+SI)". Thereafter, the process shifts to the step B12.

The CPU 132 reads the image data D34 and the sound data D13 relating to the extracted scene f(SIII+SII+SI) out of the memory device 135 in step B10. When the image data D34 and the sound data D13 relating to the extracted scene f(SIII+SII+SI) read out of the memory device 135 are reproduced, it is possible to reproduce all of the extracted image data D34 and sound data D13 such as the image data D34 and the sound data D13 at the period of time when the emotion of the living-body is heightened to sweat in a hand during the time when the operator 130 is shooting the image of the subject, the image data D34 and the sound data D13 at the period of time when the emotion of the living-body is next heightened to sweat in the hand, the image data D34 and the sound data D13 at the period of time when the emotion of the living-body is further heightened to sweat in the hand, and the like. Thus, it becomes possible to view the memorial file in which the operator's specific image data D34 and sound data D13 are recorded. Thereafter, the process shifts to the step B12.

It should be noted, when the normal mode is set in the above-mentioned step B3, that the process shifts to step B11 where the CPU 132 executes the normal mode. In the normal mode, addition of the editing start point information, the editing end point information and the like are neglected and the image data D34 of the subject and the sound data D13 when recording the ambient sound of the subject are read sequentially out of the memory device 135. Thereafter, the process shifts to the step B12.

In the step B12, the CPU 132 judges the end. For example, it is judged whether or not the push-button switch 112 constituting an editing stop switch is operated. Alternatively, it is judged whether or not power-off information is detected. When the push-button switch 112 constituting the editing stop switch is operated or when the power-off information is detected, the editing process ends. When the push-button switch 12 constituting the editing stop switch is not operated and when the power-off information is not detected, the process returns to the step B1 where the above-mentioned processes are repeated.

When executing such an editing process, it is possible to splice the image data D34 and the sound data D13 at the periods of time when emotion of the living-body is heightened to sweat in a hand during the time when the operator 130 is shooting the image of the subject by point to point from the image data D34 obtained by shooting the image of the subject with the operator 130 and the sound data D13 obtained by collecting the ambient sound of the subject therewith, thereby enabling the operator's specific image and sound data file to be produced. Furthermore, based on the setting of the short-time edition mode, the middle-time edition mode or long-time edition mode, it becomes possible to execute such an editing process of extracting the image data D34 and the sound data D13 at the period of time when the editing start point information is added and the editing end point information is added from the image data D34 of the subject and the sound data D13 when recording the ambient sound of the subject and splicing them with classifying them into three modes.

In the above-mentioned embodiments, it is also allowed to extract each of the suitable scenes as much as the period (or frequency) desired by the user from the image data D34 and the sound data D13, which are extracted and obtained from the image data D34 of the subject and the sound data D13, and further, to combine the editing algorithm for extracting with the above-mentioned algorithms I, II and III. It becomes possible to produce an album file in which more unique and impressive scenes are edited.

Embodiment 2

FIG. 9 shows a configuration of a video camera 200 of head-mounting type as a second embodiment.

In an embodiment, the video camera 200 of head-mounting type is provided with a pulse sensor 227 and a blood pressure sensor 228 other than the perspiration sensor 245a. An information processing and communication unit 250 calculates pulse information obtained from the pulse sensor 227 and blood pressure information obtained from the blood pressure sensor 28 to obtain pulse-wave transfer time (WTT). Based on this pulse-wave transfer time, it is possible to extract the image data D34 and the sound data D13 at a period of time when emotion of the living-body is heightened so much as the impression thereof remains in the mind of the operator 130 during the time when the operator 130 is shooting the image of the subject from the image data D34 obtained by shooting the image of the subject with the operator 130 and the sound data D13 obtained by collecting the ambient sound of the subject therewith.

The video camera 200 of head-mounting type shown in FIG. 9 constitutes another embodiment of the information-processing apparatus and processes information obtained by shooting the image of the subject and by collecting the ambient sound of the subject. The video camera 200 includes a main body frame 220 forming a spectacle shape. A left spectacle frame-rim 224a is mounted on the left side of the main body frame 220 open-close-freely through a hinge, which is not shown, and a right spectacle frame-rim 224b is mounted on the right side thereof open-close-freely through a hinge, which is not shown. A rear portion of the left spectacle frame-rim 224a is curved so as to be attachable on the right ear of the operator 130. Similarly, a rear portion of the right spectacle frame-rim 224b is also curved so as to be attachable on the left ear of the operator 130.

A microphone 213 (sound collection unit) is mounted on the left side of the front face of the main body frame 220 and records the ambient sound of the subject. In case of stereo-reproducing the sound, two microphones are mounted on the right and left sides of the main body frame 220. In an embodiment, a camera 234 (imaging unit) is mounted on the right side of the front face of the main body frame 220. The camera 234 contains an imaging lens, a lens drive mechanism, and an image pickup device, which are not shown, and the like. The image pickup device is provided at the rear end of the imaging lens and operates so as to shoot an image of the subject introduced by an optical system of an imaging lens, a lens drive mechanism and the like.

Various kinds of push-button switches 212 such as a power supply switch, a mode switch, a zoom switch, a shooting start/stop switch and the like are provided on the upper surface, on the lower surface and on the side surface of the main body frame 220. The power supply switch is a switch for turning on or off the power supply of the video camera 200. The mode switch is operated when selecting either one of the normal mode and the special recording mode on an occasion of shooting. Here, the special recording mode and the normal mode are modes just as explained in the above-mentioned embodiment 1.

In an embodiment, the pulse sensor 227, the blood pressure sensor 228 and the perspiration sensor 245a which constitute the information output unit are provided, detect living-body information showing emotion of the living-body of an operator who operates the video camera 200 and output the living-body information. The pulse sensor 227 is provided, for example, at the rear end of the left spectacle frame-rim 224a and detects the pulse rate of the operator 130 attached with the video camera 200 of head-mounting type on the time series to generate the pulse information thereon.

In an embodiment, a wiring band 242 is bridged between the rear end of the left spectacle frame-rim 224a and the rear end of the right spectacle frame-rim 224b. The blood pressure sensor 228 is provided approximately in the center region of the wiring band 242 and detects the blood pressure of the operator 130 attached with the video camera 200 on the time series to generate the blood pressure information. The perspiration sensor 245a is similar to the perspiration sensor 145a, which has been explained in FIG. 2, so that the explanation thereof will be omitted. The perspiration sensor 245a detects the amount of perspiration of the operator 130 touching the perspiration sensor 245a to output the living-body information showing the perspiration level to the information processing and communication unit 250.

The information processing and communication unit 250 is provided at the left spectacle frame-rim 224a of the main body frame 220 and calculates the pulse information obtained from the pulse sensor 227 and the blood pressure information obtained from the blood pressure sensor 228 to obtain the pulse-wave transfer time. Here, the pulse-wave transfer time means a period of time from a point of time when the pulse change happens to a point of time when this pulse change is reflected on the blood pressure change.

Further, a left display unit 229a and a right display unit 229b are coupled rotatably for opening and closing through hinge portions, which are not shown, on the right and left sides of the front face of the main body frame 220, and display the image of the subject shot by the camera 234 thereon. For example, the left display unit 229a and the right display unit 229b display the image when being shooting the image or when reproducing it. For the left display unit 229a and the right display unit 229b, for example, color liquid crystal display devices of around 1.0 to 2.0 inches are respectively used.

A battery and memory device, which is not shown, is provided at the right spectacle frame-rim 224b of the main body frame 220. The battery and memory device contains a battery and a memory device. The battery applies a DC power supply to the pulse sensor 227, the blood pressure sensor 228, the left display unit 229a, the right display unit 229b, the camera 234, the memory device, the perspiration sensor 245a, the information processing and communication unit 250 and the like. The memory device records the image information of the subject and the sound information of the ambient sound of the subject, which are obtained under the normal mode or the special recording mode.

An external interface 241 is provided in the center region of the front face of the main body frame 220 and can be connected with a connector for image and sound, a communication cable and the like from an external apparatus. The external interface 241 is used when outputting the image and sound to the external apparatus and the terminal for the communication cable is used when communicating with the external apparatus.

Vibration actuators 225 are provided, other than the above-mentioned components, on the left spectacle frame-rim 224a and the right spectacle frame-rim 224b and present the sense of touch by driving the vibration actuators 225 when the input is determined. Further, a pair of earphones 236l, 236r is provided, other than the vibration actuators 225, on the left spectacle frame-rim 224a and the right spectacle frame-rim 224b and function as right and left speakers. For example, the earphone 236l on the left side is arranged so as to hang down from the curved region at the rear portion of the left spectacle frame-rim 224a and to face the right ear hole of the operator 130. Similarly, the earphone 236r on the right side is arranged so as to hang down from the curved region at the rear portion of the right spectacle frame-rim 224b and to face the left ear hole of the operator 130.

The following will describe the pulse sensor 227. FIG. 10 shows a configuration of the pulse sensor 227, and FIG. 11 shows an internal configuration thereof. The optical type pulse sensor 227 shown in FIG. 10 is a sensor installable in a clock and contains a board 271, a photodiode 272, a phototransistor 273, a light selection filter 274 and a glass 275. The optical type pulse sensor 227 measures a pulse rate by utilizing blood-concentration change by pulse beats in a capillary vessel of a fingertip or the like.

The photodiode 272 and the phototransistor 273 are arranged on the board 271. The light selection filter 274 is arranged on the upper side of the photodiode 272 and the phototransistor 273. For the light selection filter 274, a red filter through which infrared light can pass is used. The glass 275 is arranged on the upper side of the light selection filter 274. It is also allowed for that member to use a transparent acrylic resin instead of the glass 275. The operator's finger 130a can touch the top of the glass 275, but in an embodiment there is employed a structure in which the temple or the like on the ear side of the operator 130 touches it.

In the pulse sensor 227, the light outputted from the photodiode 272 passes through the light selection filter 274. The infrared light passing through the light selection filter 274 reflects at the temple or the like of the operator's ear side. The reflection light reflected at the capillary vessel (vein) of the temple or the like passes through the light selection filter 274 together with the outside light and is received by the phototransistor 273. At that time, when the outside light passes through the capillary vessel of the fingertip, the temple or the like, the passing light thereof changes depending on the pulse beats of the blood. For example, the blood concentration will become dense or will become thin. This amount of concentration change is detected by being converted to an electric signal. When the detection level is set automatically in response to the amount of this outside light (amount of outside light), it becomes possible to measure the operator's pulse corresponding to the widely-ranged amount of outside light.

The internal circuit of the pulse sensor 227 shown in FIG. 11 contains an MOS-Tr 276, a band-eliminate-filter (Band Eliminate Filter: hereinafter, referred to as BEF circuit 277), and a pulse sensor block 278. The pulse sensor block 278 contains the photodiode 272 and the phototransistor 273. An anode of the photodiode 272 and a collector of the phototransistor 273 are grounded (connected to GND).

The cathode of the photodiode 272 is connected the power supply line VDD. The emitter of the phototransistor 273 is connected to a source of the MOS-Tr 276 and the BEF circuit 277, and a drain of the MOS-Tr 276 is connected to the power supply line VDD. For the MOS-Tr 276, an n-type field effect transistor is used. A gate of the MOS-Tr 276 is connected with the BEF circuit 277 constituting a negative feedback circuit. Thus, it becomes possible to measure the operator's pulse stably by negatively feeding-back the output level of the pulse detection signal S27 forming the amount of blood-concentration change in response to this amount of outside light automatically to the gate. Hereinafter, the analog to digital converted information of the pulse detection signal S27 is referred to as a pulse detection data S27. It is allowed for the analog to digital conversion function to be provided in the inside of the pulse sensor 227 or to be provided in the inside of the CPU.

Figure 12:
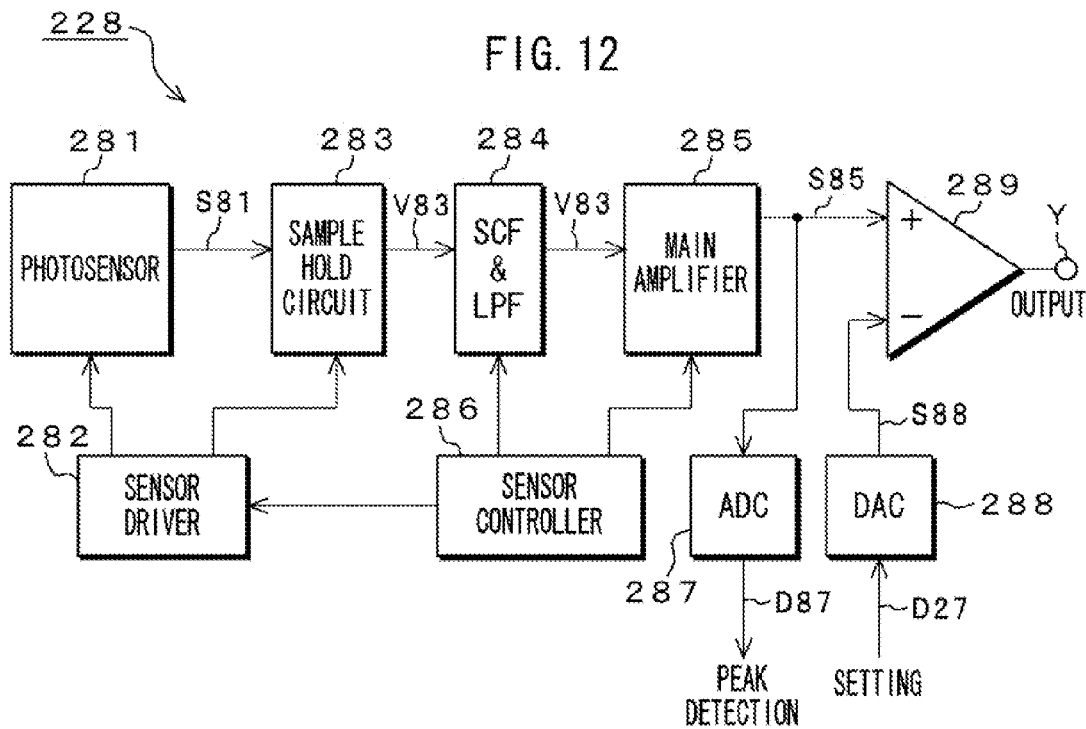
FIG. 12 is a block diagram of a blood pressure sensor 28 showing a configuration thereof.

The following will describe the blood pressure sensor 228. FIG. 12 shows a configuration of the blood pressure sensor 228. The optical type blood pressure sensor 228 shown in FIG. 12 is installable in a clock and constitutes a finger-tip pulse wave detection block. In an embodiment, it is not required for the blood pressure sensor 228 to be a grade of such a home-use blood-pressure meter (osillometric type) in which the maximum blood pressure and the minimum blood pressure are to be measured by using a cuff, so that it is possible to use the blood pressure sensor 228 having approximately the same structure as that of the pulse sensor 227, and in order to measure the pulse-wave transfer time, it is preferable for the pulse sensor 227 and the blood pressure sensor 228 to be arranged at the positions apart from each other.

The blood pressure sensor 228 applicable to the video camera 200 contains a photo sensor 281, a sensor driver 282, a sample hold circuit 283, a switched-capacitor-filter and low pass filter circuit (referred to as SCF & LPF circuit 284), a main amplifier 285, a sensor controller 286, a 4-bit AD converter (hereinafter, referred to as ADC circuit 287), a 4-bit DA converter (hereinafter, referred to as DAC circuit 288) and a comparator 289. The blood pressure sensor 228 measures a blood-pressure uprise point to obtain pulse wave arriving time.

The photo sensor 281 has approximately an equal configuration as that of the pulse sensor block 278 shown in FIG. 11, so that the explanation thereof will be omitted.

The photo sensor 281 is connected with the sensor driver 282 and the sample hold circuit 283. The sensor driver 282 drives the photo sensor 281 by applying a predetermined voltage thereto. The photo sensor 281 detects the blood pressure pulsation of the operator and outputs a blood pressure pulsation signal S81. The photo sensor 281 is connected with the sample hold circuit 283 in which the blood pressure pulsation signal S81 is sampled and a blood pressure detection voltage V83 is held and outputted.

The sample hold circuit 283 is connected with the SCF & LPF circuit 284 in which high frequency noises included in the blood pressure detection voltage V83 are eliminated. The SCF & LPF circuit 284 is connected with the main amplifier 285 in which the blood pressure detection voltage V83 after the noise elimination is amplified and a signal showing a blood-pressure uprise point (hereinafter, referred to as blood pressure signal S85) is outputted. The sensor driver 282, the SCF & LPF circuit 284 and the main amplifier 285 are connected with the sensor controller 286 by which the inputs and outputs of these of the sensor driver 282, the SCF & LPF circuit 284 and the main amplifier 285 are controlled.

The main amplifier 285 is connected with the ADC circuit 287 and the comparator 289. The comparator 289 is connected with the DAC circuit 288. The DAC circuit 288 receives 4-bit pulse detection data D27a which determines a cut out level. The DAC circuit 288 converts the pulse detection data D27a from a digital to an analog to output an analog pulse detection signal S88 to the comparator 289. The ADC circuit 287 monitors the signal amplitude of the blood pressure signal S85 outputted from the main amplifier 285. The ADC circuit 287 converts the blood pressure signal S85 from an analog to a digital and outputs digital blood pressure detection data D87. In the blood pressure detection data D87, there are included the maximum value of the operator's blood pressure and the like.

The comparator 289 compares the blood pressure signal S85 outputted from the main amplifier 285 with the pulse detection signal S88 outputted from the DAC circuit 288 and outputs a difference signal Y showing the pulse-wave transfer time (WTT). With respect to this difference signal Y, data after being analog to digital converted is denoted by Y. Thus, it becomes possible to output the data Y showing the pulse-wave transfer time (WTT) while executing discrimination of the blood pressure signal S85 from the external ambient noise.

Figure 13A:
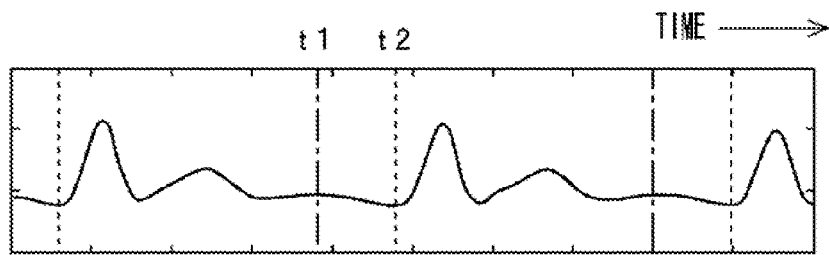
FIGS. 13A and 13B are graph diagrams showing a blood pressure detection example, a pulse detection example, and a calculation example of pulse-wave transfer time.
Figure 13B:
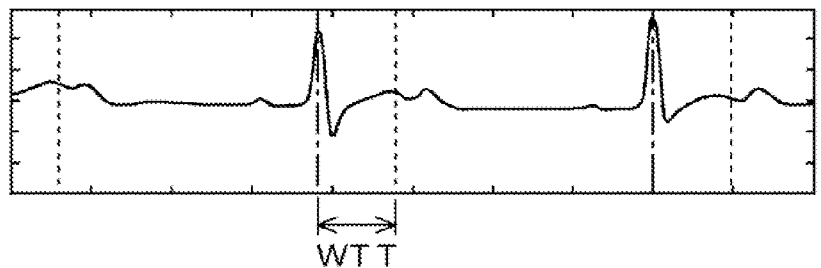

FIGS. 13A and 13B show a blood pressure detection example, a pulse detection example, and a calculation example of pulse-wave transfer time.

In the blood pressure detection example shown in FIG. 13A, the horizontal axis denotes time and the vertical axis denotes blood pressure. The blood pressure means the pressure applied to the blood-vessel wall when the blood is pumped out to the whole body by the pumping action of the heart. According to the blood pressure detection example shown in FIG. 13A, the maximum blood pressure and the minimum blood pressure repeat alternately along with the elapse time. The maximum blood pressure means the blood pressure when the heart is contracted in order to pump out the blood (blood pressure in contraction period). The minimum blood pressure means the blood pressure when the heart is expanded in order to stock the blood (blood pressure in expansion period).

In a pulse detection example shown in FIG. 13B, the horizontal axis denotes time and the vertical axis denotes pulse strength. The pulse means a beat which occurs at the artery when the heart pumps out the blood. By counting the number of times of these beats, a pulse rate can be obtained. The number of times in which the heart pulsates in a constant period of time is referred to as a heart rate and usually, it is expressed by the number of beats per one minute (bpm: beats per minute).

According to the pulse detection example shown in FIG. 13B, portions shown by peak pulses (steeple pulses) express beats. The pulse is displayed by a cardiac electrogram. WTT shown in the drawing denotes a pulse-wave transfer time (pulse-Wave Transfer Time) and means a period of time until the pulse change is reflected on the blood change. For example, it means a period of time from the point of time t1 when a pulsation peak is detected to the point of time t2 of the uprise starting point of the blood pressure. Generally, it is known that the pulse-wave transfer time (hereinafter, referred to as WTT) becomes short when a person is impressed, is excited or gets nervous.

Consequently, in the embodiment 2, the living-body information showing emotion of the living-body is extracted by using the WTT. First, similarly as the embodiment 1, the difference (change rate) of the amount of perspiration is calculated. This difference is compared with a certain threshold and when the difference exceeding this threshold is detected, the image scene is made as an object of the extracted scene. Then, assuming that the WTT at a certain time is assumed as data Y and a constant of a unit corresponding to the time change of the amount of perspiration is assumed as a threshold B, the following formula (2) will be discriminated.

$$Y<B \quad (2)$$

Thus, it becomes possible for the CPU 132 to discriminate the emotion when a person is impressed, is excited, gets nervous or the like at the present time.

Figure 14:
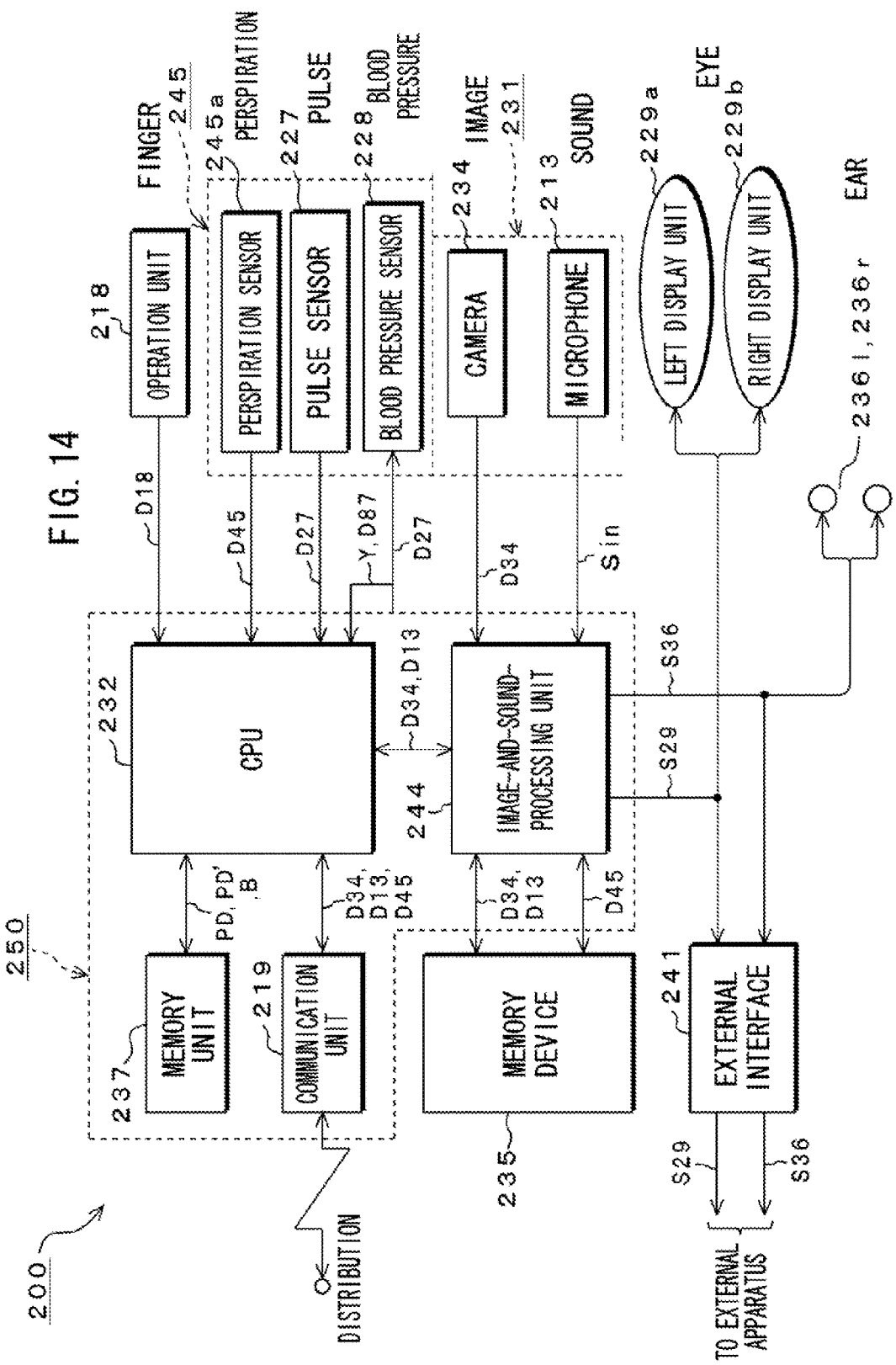
FIG. 14 is a block diagram showing a configuration of a control system of the video camera 200.

FIG. 14 shows a configuration of a control system of the video camera 200. In the video camera 200 shown in FIG. 14, respective function blocks is mounted on the insides of the left spectacle frame-rim 224a and the right spectacle frame-rim 224b and on the inside of the main body frame 220. It should be noted that in FIG. 14, portions corresponding to the respective portions shown in FIG. 9 to FIG. 12 are denoted as the same reference numerals.

The video camera 200 contains the operation unit 218, the left display unit 229a, the right display unit 229b, an image-and-sound-recording unit 231, the memory device 235, the external interface 241, the living-body sensor unit 245 and the information processing and communication unit 250. The information processing and communication unit 250 includes the communication unit 219, the CPU 232, the memory unit 237 and the image-and-sound-processing unit 244.

The CPU 232 controls the whole of the video camera 200 based on a system program, which is similar to the embodiment 1. The memory unit 237 includes a ROM, a RAM, an EEPROM and the like, which are not shown. In the ROM or the EEPROM of the memory unit 237, data PD forming the system program for controlling the whole of the video camera are stored. The RAM which is not shown is used as a work memory. The CPU 232 reads the data PD forming the system program out of the ROM or the EEPROM concurrently with the power supply ON to expand it in the RAM and starts up the system to control the whole of the video camera.

In the ROM or the EEPROM of the memory unit 237, a program for executing the special recording mode other than the system program is described. The program for this special recording mode is a computer readable program which is used for moving-picture recording the information obtained by shooting the image of the subject and by collecting the ambient sound of the subject based on the emotion of the living-body of the operator 130, in an embodiment based on the perspiration, the pulse and the blood pressure. With respect the contents thereof, there are described a step of obtaining image information by shooting the image of the subject and also obtaining sound information by collecting the ambient sound of the subject; a step of detecting and producing the living-body information such as the perspiration, the pulse, and the blood pressure, showing emotion of the living body of an operator 130 who operates the image-and-sound-recording unit 231; and a step of performing processing to establish the correspondence between the produced living-body information and the image information of the subject and/or the sound information of the ambient sound of the subject, which are shot and collected.

When the data PD forming such a program is read out of the ROM or the EEPROM and is executed, the CPU 232 can execute an editing process or the like in which the correspondence between the data Y showing the pulse-wave transfer time, which is produced by detecting the living-body information showing emotion of the living-body of the operator 130 and the image information of the subject and/or the sound information of the ambient sound of the subject, which are shot and collected, is established when processing the information obtained by shooting the image of the subject and by collecting the ambient sound of the subject.

In an embodiment, the CPU 232 is connected with the perspiration sensor 245a, the pulse sensor 227 and the blood pressure sensor 228, which constitute the living-body sensor unit 245. The living-body sensor unit 245 constitutes the information output unit. The CPU 232 receives the perspiration detection data D45 outputted from the perspiration sensor 245a, the pulse detection data D27 outputted from the pulse sensor 227, and the blood pressure detection data D87 outputted from the blood pressure sensor 228. Then, the CPU 232 executes a process so as to establish the correspondence between the data Y showing the pulse-wave transfer time obtained by calculating these items of the perspiration detection data D45, the pulse detection data D27, and the blood pressure detection data D87 and the image data D34 of the subject and/or the sound data D13 when recording the ambient sound of the subject, which are outputted from the image-and-sound-recording unit 231.

In an embodiment, the perspiration detection data D45 outputted from the perspiration sensor 245a is used for calculating, similarly as the embodiment 1, the difference (change rate) of the amount of perspiration. This difference is compared with a certain threshold and when the difference exceeding this threshold is detected, it is used for determining an object of the extracted scene in the image scenes.

The blood pressure sensor 228 detects the blood pressure of the operator 130 who operates the image-and-sound-recording unit 231 to output the blood pressure detection data D87. For example, as the blood pressure sensor 228, an optical type blood pressure sensor mounted with the finger-tip pulse wave detection block shown in FIG. 12 is used. The blood pressure sensor 228 detects the blood pressure of the operator 130 who operates the image-and-sound-recording unit 231 on the time series and receives the pulse detection data D27 from the pulse sensor 227 to calculate the data Y showing the pulse-wave transfer time and to output it to the CPU 232.

In an embodiment, the CPU 232 compares the data Y showing the pulse-wave transfer time outputted from the blood pressure sensor 228 with a threshold B for judging the pulse-wave transfer time which becomes the judgment criterion of the data Y. The threshold B for judging the pulse-wave transfer time forms one example of the judgment criterion information. Owing to this comparison result, when the blood pressure sensor 228 detects, for example, the data Y showing the pulse-wave transfer time which becomes less than the threshold B for judging the pulse-wave transfer time, the CPU 232 controls the image-and-sound-processing unit 244 to executes a point setting so as to add editing start point information to the image data D34 of the subject and the sound data D13 when recording the ambient sound of the subject.

Thereafter, when the blood pressure sensor 228 detects the data Y showing the pulse-wave transfer time which exceeds the threshold B for judging the pulse-wave transfer time, the CPU 232 controls the image-and-sound-processing unit 244 to executes a point setting so as to add editing end point information to the image data D34 of the subject and the sound data D13 when recording the ambient sound of the subject.

The image-and-sound-processing unit 244, similarly as the embodiment 1, compresses the image data D34 in compliant with the MPEG-1 standard and records it on the memory device 235. According to the compression-process in compliant with the MPEG-1 standard, data of only moving portions in the image is detected and compressed so as to be saved. The compression-process is not limited to MPEG-1 and it is also allowed to employ each of the standards from MPEG-2 to MPEG-4 with high definition television correspondence or the MPEG-7 standard which is presently in process of standardization.

In an embodiment, the memory unit 237 stores the threshold B for judging the pulse-wave transfer time. For example, the threshold B is stored as a trigger parameter beforehand in a ROM or the like provided in the memory unit 237. The RAM of the memory unit 237 receives the data Y showing the pulse-wave transfer time under the memory control of the CPU 232, compares the preset threshold B for judging the pulse-wave transfer time with the pulse-wave transfer time (WTT) obtained from the data Y, and executes a judgment process of Y<B and a judgment process of Y≧B or the like. It is needless to say that the threshold B is not limited to an unambiguous constant and it is also allowed to employ a variable which changes in a second order function.

By doing in this manner, it becomes possible to extract specific image and sound corresponding to the perspiration, the pulse and the blood pressure of the operator 130. The editing start point information and the editing end point information are, similarly as the embodiment 1, set (described) as time codes with respect to the recording time information. By setting these time codes, it becomes possible to automatically extract the image data D34 and the sound data D13 at a period of time when emotion of the living-body is heightened to increase the pulse rate or the blood pressure during the time when the operator 130 is shooting the image of the subject.

The CPU 232 is connected with the communication unit 219 which communicates an external apparatus. For example, a radio communication device is used for the communication unit 219. The CPU 232 controls the communication unit 219 to radio-distribute the image data D34 of the subject and the sound data D13 when recording the ambient sound of the subject, which are extracted and spliced based on the editing process, to a base station or the like. When executing such a radio distributing process, it is possible to display the image data D34 and the sound data D13 at a period of time when emotion of the living-body is heightened to increase the pulse rate or the blood pressure during the time when the operator 130 is shooting the image of the subject on the monitor of a base station and the like or to distribute them to another information processing system by utilizing the communication unit of the base station. Further, it becomes possible, similarly as the embodiment 1, to download a file (algorithm) in which the operator's specific image data D34 and sound data D13 are recorded to other users through the Internet or the like.

The operation unit 218 is connected to the CPU 232 and outputs operation data D18 generated by pushing down the push-button switches 212 such as the power supply switch, the mode switch, the zoom switch, the shooting start/stop switch and the like, which are not shown, to the CPU 132. The image-and-sound-recording unit 231 contains the microphone 213 and the camera 234. The microphone 213 is connected to the image-and-sound-processing unit 244 and outputs the sound signal Sin obtained by collecting the ambient sound of the subject. The image-and-sound-processing unit 244 converts the sound signal Sin outputted from the microphone 213 from analog to digital to output the digital sound data D13 to the memory device 235. For the microphone 213, a microphone explained in the embodiment 1 is used. The camera 234 is connected to the image-and-sound-processing unit 244 and outputs the image data D34 obtained by shooting the image of the subject. The camera 234 contains an imaging lens, an image pickup device and a lens drive mechanism.

The above-mentioned CPU 232 is connected with the memory device 235 and, on an occasion of the special recording mode, it stores record information which establishes the correspondence between the data Y showing the pulse-wave transfer time, which are produced by detecting the living-body information showing emotion of living-body such as the perspiration, the pulse and the blood pressure or the like of the operator 130 and the image data D34 of the subject and/or the sound data D13 when recording the ambient sound of the subject, which are shot and collected. For the memory device 235, a hard disk device or a non volatile memory such as a memory card is used.

The above-mentioned image-and-sound-processing unit 244 is connected with the left display unit 229a and the right display unit 229b which display the image when being shooting it and the image when being reproduced based on the image display signal S29. The image-and-sound-processing unit 244 is connected with the earphones 236l, 236r which output the ambient sound of the subject when being shooting the image, sound when the shot image is reproduced and the like based on the sound signal S36. The earphones 236l, 236r are provided at the predetermined positions of the left spectacle frame-rim 224a and the right spectacle frame-rim 224b. The image-and-sound-processing unit 244 is connected with the external interface 241 which outputs the image and sound signals or the like to the external apparatus.

FIGS. 15A through 15F and FIGS. 16A through 16F show shooting format examples (No. 1, No. 2 thereof) in the video camera 200 of head-mounting type. In an embodiment, it is constituted such that specific image and sound can be extracted corresponding to the changes of the perspiration, the pulse and the blood pressure at the head portion of the operator 130 and at the same time, the editing start point information and the editing end point information are set (described) as time codes with respect to the recording time information.

Figure 15:
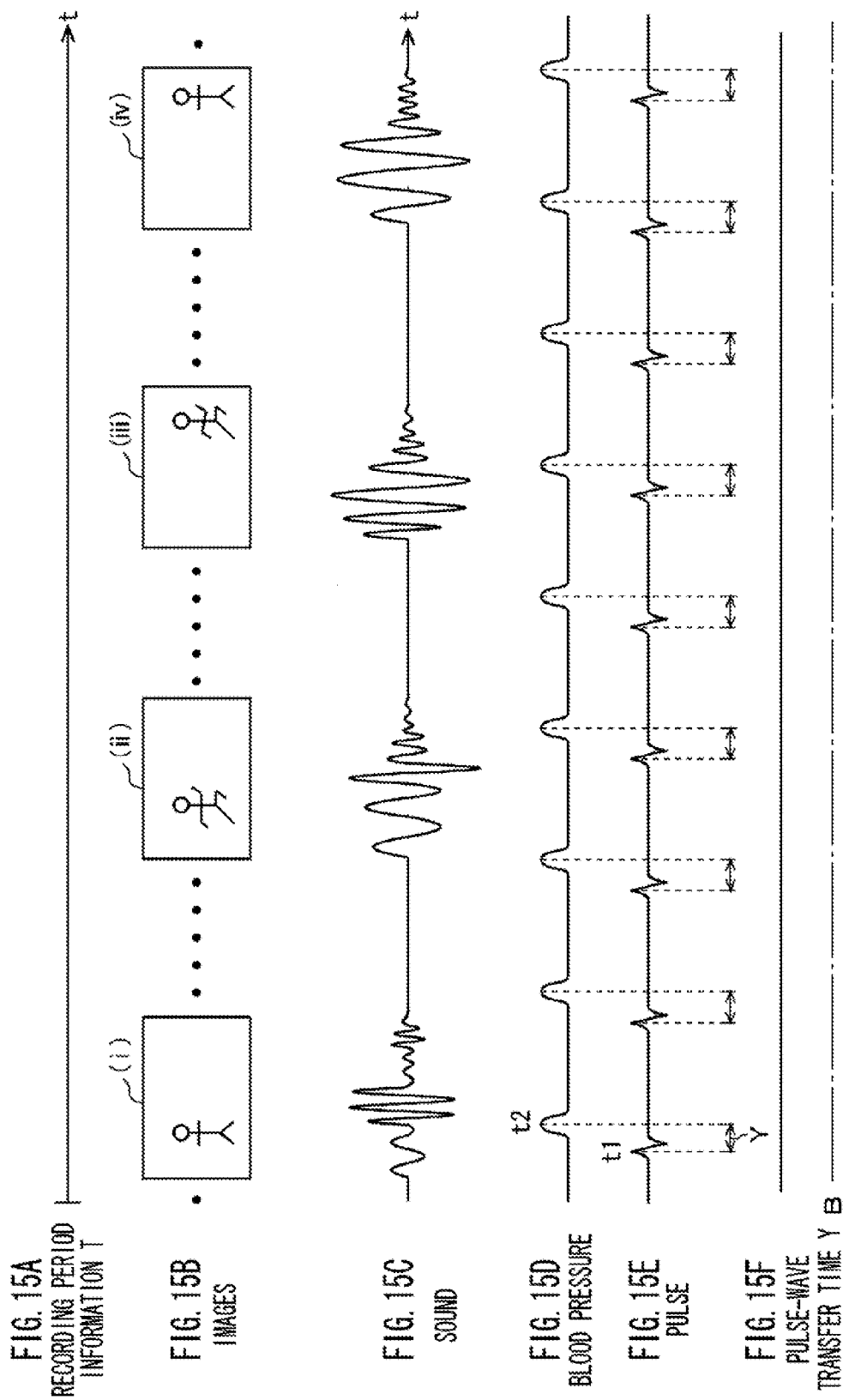
FIGS. 15A through 15F are timing charts showing a shooting format example (No. 1 thereof) in the video camera 200.
Figure 16:
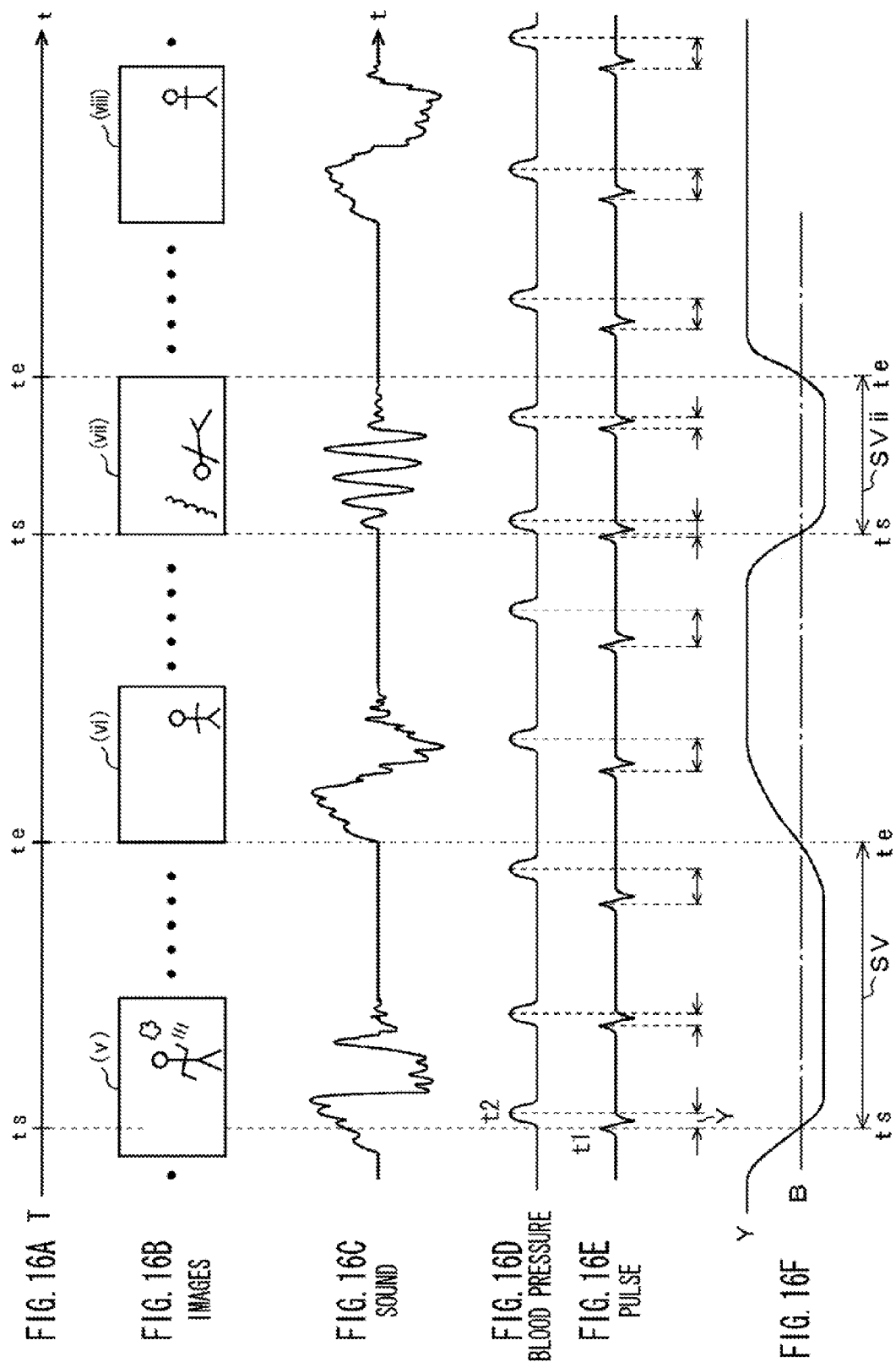
FIGS. 16A through 16F are timing charts showing the shooting format example (No. 2 thereof) in the video camera 200.

FIG. 15A and FIG. 16A show the recording time information T. The recording time information T means a period of time when the start switch is pushed down and the image data D34 is taken in and recorded on the memory device 235. The moving picture scenes shown in FIG. 15B and FIG. 16B are, similarly as the embodiment 1, eight scenes (i) to (viii) representing the subject movements. Sampling frequency of the moving picture scene is 1/30 sec. More specifically, the camera 234 obtains images of 30 frames for every one second (according to NTSC system). In an embodiment, there is dealt with a case in which the operator 130 is shooting images of a subject who is attending the "foot race" in an athletic meet.

The scene (i) shown in FIG. 15B is, similarly as the embodiment 1, an image when the subject is waiting for his race. The scenes (ii) and (iii) are images when his turn has come finally and the subject moves to the start line. The scene (iv) is an image when the subject stands at the start line.

Further, the scene (v) shown in FIG. 16B is an image at the instant when a starter fires a signal gun. The scene (vi) is an image when the subject starts running. The scene (vii) is an image of a state in which the subject fall down caused by his excess energy. The scene (viii) is an image when the subject reaches the goal while crying.

The waveform shown in FIG. 15C denotes a sound signal when recording the ambient sound of the subject. The microphone 213 records the ambient sound of the subject. In an embodiment, ambient sound of the subject who is attending the "foot race" of the athletic meet is recorded. For example, with respect to the sound information corresponding to the scenes (i) to (iv), a march and an ambient noise sounds which are specific to an athletic meet are recorded. Further, with respect to the sound information corresponding to the scene (v) shown in FIG. 16C, there are recorded the "blam" sound and the like at the instant when the starter fires the signal gun and at the same time, cheering sounds by cheering persons corresponding to the scene (vi) are recorded. For the sound information corresponding to the scene (vii), for example, such a cheer as "Now, get up and keep on!" with respect to the subject is recorded. For the sound information corresponding to the scene (viii), for example, a commotion of relief with respect to the activity that the subject finished the race is recorded.

The waveform shown in FIG. 15D is a blood pressure waveform obtained from the blood pressure detection data D87 and denotes time-lapse change of the blood pressure of the operator who shoots the image of the subject with holding the video camera 200. The waveform shown in FIG. 15E is a pulsation waveform obtained from the pulse detection data D27 and denotes time-lapse change of the pulse of the operator who shoots the image of the subject with holding the video camera 200. In FIG. 15E, the data Y denotes the pulse-wave transfer time (WTT) and denotes, for example, a period of time from a point of time t1 when a pulsation peak is detected to a point of time t2 of the uprise starting point of the blood pressure.

In an embodiment, there is shown a case in which the blood pressure corresponding to the scenes (i) to (iv) is stable almost without time-lapse change and in addition, also the pulse corresponding to the scenes (i) to (iv) is stable without time-lapse change. More specifically, the data Y showing the pulse-wave transfer time is, as shown in FIG. 15F, equal to or more than the threshold B for judging the pulse-wave transfer time in any case.

However, in the scene (v) shown in FIG. 16D, immediately after the subject stands at the start line, the pulse of the operator begins to increase, at the same time, the blood pressure begins to increase and at the instant when the starter fires the signal gun, for example, the peaks thereof have come. The data Y showing the pulse-wave transfer time in this case is in a state shorter than the data Y showing the pulse-wave transfer time in case of the scenes (i) to (iv). In the scene (vi), from a point of time when the subject starts running, the pulse and the blood pressure also return to the values of normal time gradually. The data Y showing the pulse-wave transfer time in this case is in a state approximately equal to the data Y showing the pulse-wave transfer time in case of the scenes (i) to (iv).

However, in the scene (vii), when it becomes a state in which the subject falls down caused by his excess energy, the pulse and the blood pressure of the operator begin to increase again and at the instant when the subject stands up, for example, the peaks thereof have come. The data Y showing the pulse-wave transfer time in this case is in a state shorter than the data Y showing the pulse-wave transfer time in case of the scenes (i) to (iv). Then, the pulse and the blood pressure also return to the values of normal time gradually. In an embodiment, in the scene (viii), at the point of time when the subject finishes the race while crying, the pulse and the blood pressure of the operator returns to the same state as that of the beginning.

It should be noted, with respect to the time-lapse change of the amount of perspiration of the operator who is shooting the image of the subject with holding the video camera 200, that FIG. 4D and FIG. 5D should be referred thereto. It is known that the amount of perspiration, the pulse and the blood pressure increase with respect to the emotion change of such an operator and the amount of perspiration, the pulse and the blood pressure thereof will return to a state at a normal time depending on the elapse time.

In an embodiment, different from the embodiment 1, the threshold B for judging the pulse-wave transfer time is set unambiguously concurrently with the starting up of the special recording mode. In the scene (v) shown in FIG. 16D, the data Y showing the pulse-wave transfer time along with the operator's pulse and blood pressure changes becomes less than the threshold B for judging the pulse-wave transfer time. The point of time ts when this data Y becomes less than the threshold B forms a first time code and at the same time, becomes the editing start point information when editing moving picture scenes.

Further, time elapses and in the scene (vi) shown in FIG. 16D, the operator's pulse and blood pressure return to the values of a normal time and the data Y becomes equal to or more than the threshold B. The point of time te when this data Y exceeds the threshold B forms the first time code and at the same time, becomes the editing end point information when editing the moving picture scenes. The moving picture scene between the point of time ts and the point of time te of these first time codes becomes, similarly as the embodiment 1, a first extracted (picking) scene Sv (image and sound information for edition) in the special recording mode.

In an embodiment, time elapses further and in the scene (vii) shown in FIG. 16D, the operator's pulse and blood pressure increase and the data Y becomes less than the threshold B. A point of time ts when the data Y along with these pulse and blood pressure changes becomes less than the threshold B forms a second time code and at the same time, becomes the editing start point information when editing moving picture scenes. Further, time elapses and in the scene (vii) shown in FIG. 16D, the operator's pulse and blood pressure return to a state of a normal time and the data Y becomes equal to or more than the threshold B. The point of time te when this data Y along with these pulse and blood pressure changes exceeds the threshold B forms the second time code and at the same time, becomes the editing end point information when editing the moving picture scenes. The moving picture scene between the point of time ts and the point of time te of these second time codes becomes, similarly as the embodiment 1, a second extracted (picking) scene SVii (image and sound information for edition) in the special recording mode. It should be noted that a contribution rate of a parameter F which contributes with respect to emotion change is shown in table 1.

TABLE 1

| Parameter | Heart Rate | Blood Pressure | WTT | Body temperature | amount of perspiration |
|---|---|---|---|---|---|
| ☐ | 0.94 | 1.06 | 1.30 | 0.44 | 1.93 |

According to the table 1, when considering about the parameter F contributing with respect to the emotion change, the contribution rate is 0.94 in case of the heart rate, the contribution rate is 1.06 in case of the blood pressure, the contribution rate is 1.30 in case of the WTT, the contribution rate is 0.44 in case of the body temperature, and the contribution rate is 1.93 in case of the amount of perspiration. In an embodiment, there is obtained a relationship such as amount-of-perspiration>WTT>blood-pressure>heart-rate.

Figure 17:
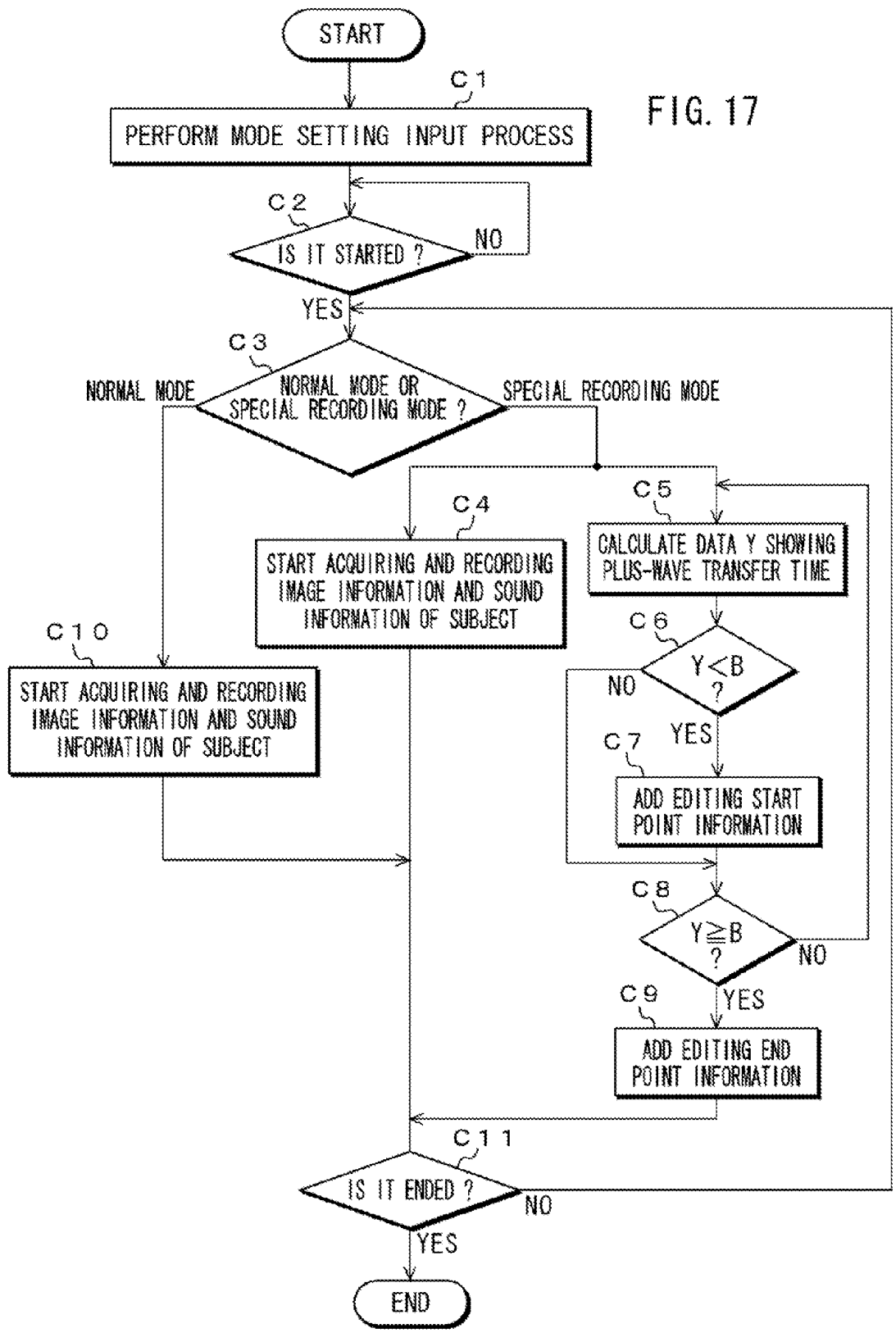
FIG. 17 is a flowchart showing an information recording example in the video camera 200.

The following will describe a second embodiment of the information-processing method according to the present application. FIG. 17 shows an information-recording example in the video camera 200.

In an embodiment, a case is assumed in which the information obtained by shooting the image of the subject with the video camera 200 of head-mounting type and by collecting the ambient sound of the subject is processed. For the living-body sensor unit 245, the perspiration sensor 245a, the pulse sensor 227 and the blood pressure sensor 228 as shown in FIG. 14 are used. The CPU 232 executes a process so as to establish the correspondence between the data Y showing the pulse-wave transfer time based on the perspiration detection data D45, the pulse detection data D27 and the blood pressure detection data D87 outputted from the living-body sensor unit 245 and the image data D34 of the subject and/or the sound data D13 when recording the ambient sound of the subject, which are outputted from the image-and-sound-recording unit 231.

On the premise of these, the CPU 232 executes a mode setting input process in step C1 of the flowchart shown in FIG. 17. For example, the operation data D18 relating to the setting of the normal mode or the special recording mode is inputted. At that time, the user operates a push-button switch 212 constituting a mode switch to select either one of the normal mode and the special recording mode. For example, when he or she operates the special recording mode by operating the push-button switch 212, the operation unit 218 outputs the operation data D18 showing the special recording mode to the CPU 232.

Next, in step C2, the CPU 232 waits for the start. At that time, the user operates the push-button switch 212 constituting a shooting start switch to instruct a start of the moving picture recording process to the CPU 232. The operation unit 218 outputs the operation data D18 instructing the start of the moving picture recording process to the CPU 232.

When the operation unit 218 instructs the start of the moving picture recording process to the CPU 232, the process is branched by setting the normal mode or the special recording mode in step C3. If the special recording mode is set in the step C1, the CPU 232 controls the image-and-sound-recording unit 231, in step C4, so as to acquire the information on the image of the subject and the ambient sound of the subject and the process shifts to the recording start processing. At that time, the image-and-sound-recording unit 231 obtains the image data D34 by shooting the image of the subject and also, obtains the sound data D13 by collecting the ambient sound of the subject. The image-and-sound-processing unit 244 records the image data D34 in which only the moving portion in the image is detected and compressed, for example, in compliant with the MPEG-1 standard on the memory device 235.

In parallel with this, in step C5, the CPU 232 controls the blood pressure sensor 228 so as to detect the living-body information showing emotion of the living-body such as the perspiration, the pulse, and the blood pressure of the operator 130 who operates the video camera 200 to produce the data Y showing the pulse-wave transfer time. The blood pressure sensor 228, under this control, detects the blood pressure of the operator 130 operating the image-and-sound-recording unit 231 to output the blood pressure detection data D87 to the CPU 232. At that time, the blood pressure sensor 228 detects the blood pressure of the operator 130 who operates the image-and-sound-recording unit 231 on the time series, and further, receives the pulse detection data D27 from the pulse sensor 227, and calculates the data Y showing the pulse-wave transfer time to output it to the CPU 232.

Next, the process shifts to step C6 where the CPU 232 executes a discrimination process of Y<B by comparing the data Y showing the pulse-wave transfer time outputted from the blood pressure sensor 228 with the threshold B for discriminating the pulse-wave transfer time which becomes the judgment criterion of the data Y. The memory unit 237 receives the data Y under the memory control of the CPU 232, and the preset threshold B and the pulse-wave transfer time (WTT) obtained from the data Y are compared.

When a discrimination result such as Y<B is obtained, the process shifts to step C7 where the CPU 232 adds editing start point information to the image data D34 of the subject and the sound data D13 when recording the ambient sound of the subject, which are recorded by simultaneous proceedings in the memory device 235 in the step C4. At that time, according to the example of the scene (v) shown in FIG. 16, the blood pressure sensor 228 detects the data Y showing the pulse-wave transfer time which exceeds the threshold B, so that the CPU 232 adds editing start point information to the image data D34 of the subject and the sound data D13 when recording the ambient sound of the subject. In the image-and-sound-processing unit 244, by the editing start point information adding control (point setting control) from the CPU 232, the point of time ts is marked (described) as a time code in the recording time information T.

Then, the process shifts to step C8 where the CPU 232 executes a discrimination process of Y≧B. When discriminating Y≧B, the process shifts to step C9 where the CPU 232 controls the image-and-sound-processing unit 244 to execute the point setting so as to add the editing end point information to the image data D34 of the subject and the sound data D13 when recording the ambient sound of the subject, which are recorded by simultaneous proceedings in the memory device 235 in the step C4. At that time, according to the example of the scene (v) shown in FIG. 16, the blood pressure sensor 228 detects the data Y showing the pulse-wave transfer time equal to or more than the threshold B, so that the CPU 232 controls the image-and-sound-processing unit 244 to execute the point setting so as to add the editing end point information to the image data D34 of the subject and the sound data D13 when recording the ambient sound of the subject.

In the image-and-sound-processing unit 244, by the editing end point information adding control (point setting control) of the CPU 232, the point of time te is marked (described) as a time code in the recording time information T. The moving picture scene between the point of time ts and the point of time te for these time codes becomes a first extracted (picking) scene Sv (image and sound information for edition) in the special recording mode (see FIG. 16). Then, the process shifts to step C11.

It should be noted that when the normal mode is set in the step C3, the process shifts to step C10 where the normal mode is executed. In the normal mode, the editing start point information, the editing end point information or the like is not added and the image data D34 of the subject and the sound data D13 when recording the ambient sound of the subject are recorded on the memory device 235. Thereafter, the process shifts to the step C11.

In the step C11, the CPU 232 executes ending judgment. For example, it is judged whether or not the push-button switch 212 constituting the shooting stop switch is operated. Alternatively, it is judged whether or not power-off information is detected. When the push-button switch 212 constituting the shooting stop switch is operated or when the power-off information is detected, the moving picture recording process ends. When the push-button switch 212 constituting the shooting stop switch is not operated and when the power-off information is not detected, the process returns to the step C3 where the above-mentioned processes are repeated. Thus, it becomes possible to store on the memory device 235 the data with establishing the correspondence between the data Y showing the pulse-wave transfer time, which are obtained from the blood pressure sensor 28, and the image data D34 of the subject and/or the sound data D13 when recording the ambient sound of the subject, which are shot and collected, and to execute the moving picture recording process.

According to the example shown in FIGS. 15A through 15F and FIGS. 16A through 16F, time codes (points of time) ts, te which can edit the first and second extracted scenes are added. By doing in this manner, it becomes possible to extract a specific image and sound corresponding to the perspiration, the pulse and the blood pressure of the operator 130. The editing start point information and the editing end point information are, for example, set (described) as time codes with respect to the recording time information T.

In this manner, according to the video camera and information-processing method as the second embodiment, in case of processing information obtained by shooting the image of the subject and by collecting the ambient sound of the subject, the image-and-sound-recording unit 231 outputs the image data D34 by shooting the image of the subject and also, outputs the sound data D13 by collecting the ambient sound of the subject. The blood pressure sensor 228 outputs the data Y showing the pulse-wave transfer time by detecting the living-body information showing emotion of the living-body of the operator 130 who operates the image-and-sound-recording unit 231. On the premise of this, the CPU 232 can execute a process so as to establish the correspondence between the data Y outputted from the blood pressure sensor 228 and the image data D34 of the subject and/or the sound data D13 when recording the ambient sound of the subject, which are outputted from the image-and-sound-recording unit 231.

Consequently, it becomes possible to automatically extract the image data D34 and the sound data D13 at a period of time when emotion of the living-body is heightened to increase the pulse rate and the blood pressure during the time when the operator is shooting the image of the subject, thereby enabling the operator's specific image and sound data file which is obtained by editing the image data D34 and the sound data D13 extracted automatically here to be easily and also simply produced. Thus, it becomes possible to improve editing work dramatically as compared with a case in which an editing start point, an editing end point or the like is appointed and inputted by a manual operation on the way of shooting the image of the subject.

In an embodiment, although it has been explained with respect to a case in which the image data D34 and the sound data D13 at the period of time when emotion of the living-body is heightened are automatically extracted by using the pulse sensor 227 and the blood pressure sensor 228, it is not limited to this; the similar effect is obtained even if the image data D34 and the sound data D13 at the period of time when emotion of the living-body is heightened are automatically extracted by using the brain wave sensor instead of the pulse sensor 227, the blood pressure sensor 228 or the like.

Embodiment 3

Figure 18:
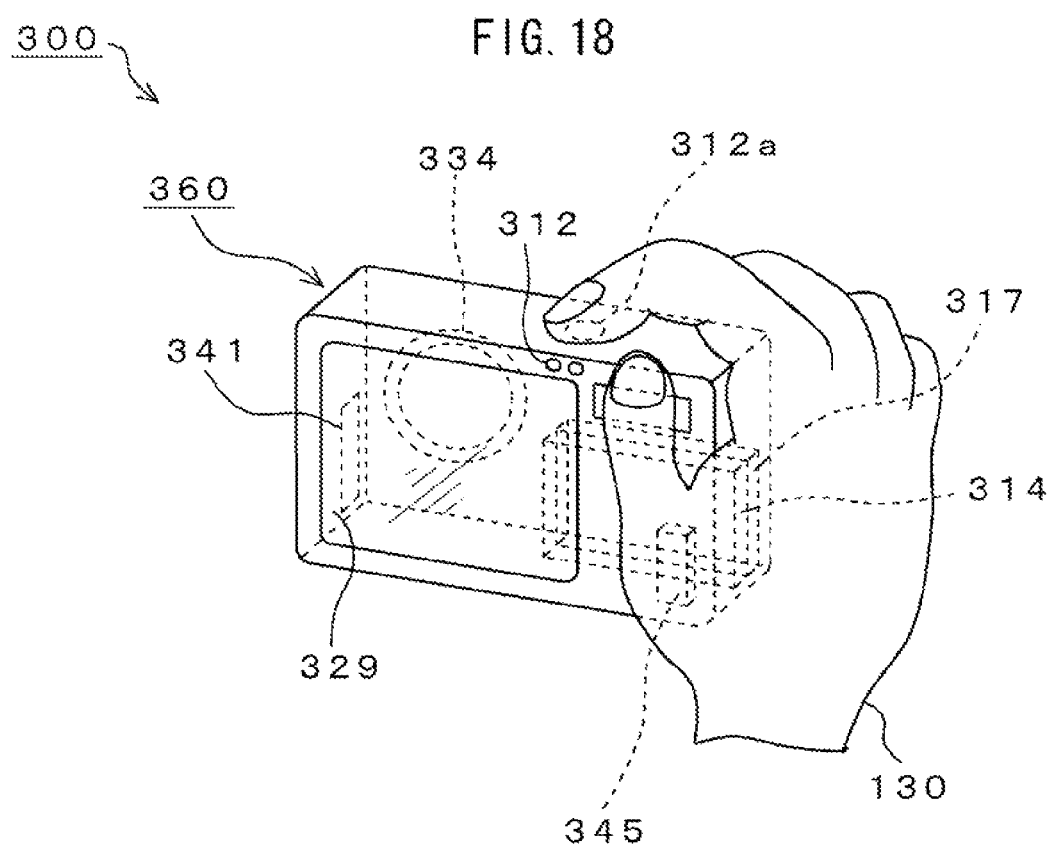
FIG. 18 is a perspective view of a digital camera 300 as a third embodiment for showing a configuration thereof.

FIG. 18 shows a configuration of a digital camera 300 as a third embodiment. The digital camera 300 shown in FIG. 18 constitutes the information-processing apparatus and processes still picture information and moving picture information of impressive scene which are obtained by shooting an image of the subject and sound information obtained by collecting an ambient sound of the subject.

The digital camera 300 includes a main body case 360 constituting an exterior package and an imaging unit 334 is installed on the front face side of the main body case 360. The imaging unit 334 contains an imaging lens, a lens drive mechanism, image pickup device, which are not shown, and the like. The image pickup device is provided at the rear end of the imaging lens and operates so as to shoot the image of the subject which is introduced by an imaging optical system such as the imaging lens and a lens drive mechanism.

Various kinds of push-button switches 312 such as a power supply switch, a mode switch, a zoom switch, and a shutter switch 312a are provided on the rear surface, the upper surface and the side surfaces of the main body case 360. The power supply switch is a switch for turning on or off the power supply of the digital camera 300. The mode switch is operated when selecting either one of the normal mode and the special moving picture recording mode on an occasion of shooting. Here, the special moving picture recording mode relates to a mode in which recording is performed with establishing the correspondence between detected and produced living-body information showing emotion of living-body of an operator and image (moving picture) information of the subject and/or sound information of ambient sound of the subject, which are shot and collected. The normal mode relates to a mode other than the special moving picture recording mode. In the normal mode, the image information of the subject and the sound information of the ambient sound of the subject which are shot and collected are directly recorded independently of the emotion of living-body of the operator.

In an embodiment, as the mode switch that selects the special moving picture recording mode, a living-body sensor unit 345 constituting the information output unit is provided and detects living-body information showing emotion of living-body of an operator who operates the digital camera 300 to output the living-body information. For the living-body sensor unit 345, for example, a perspiration (hidrosis) sensor 145a as shown in FIG. 2 is used. In an embodiment, the perspiration sensor 145a is provided on the right lower portion of the rear surface of the main body case 360. This portion is a grip portion at which the digital camera 300 is grasped by the operator's right hand. Of course, it is not limited to the grip portion; it is also allowed to provide the living-body sensor unit 345 at the position where the shutter switch 312a is used compatibly. Thus, it becomes possible to detect the amount of perspiration of the operator touching the shutter switch 312a and to output the living-body information showing the perspiration level to the information-processing unit 315. Also, for the living-body sensor unit 345, it may use the pulse sensor 327, the blood pressure sensor 328 or the like other than the perspiration sensor 145a.

The zoom switch, which is not shown, is operated when a zoom-up display of the image of the subject or a zoom-down display thereof is executed. The shutter switch 312a is ON-operated when instructing taking-in of the still picture information of the image of the subject displayed on a display unit 329 to the information-processing unit 315. A microphone for recording sounds, which constitutes a sound collection unit 313, is mounted below the front edge of the imaging lens on the front face of the main body case 360. In case of stereo-reproducing the sound, right and left two microphones may be mounted.

Further, the display unit 329 is mounted on the rear surface of the main body case 360 and moving-picture displays (monitors) the image of the subject shot by the imaging unit 334. For example, the display unit 329 displays images (moving pictures) when being shooting them and still picture or moving pictures while being reproduced when the shutter switch 312a is ON-operated. For the display unit 329, for example, a color liquid crystal display device of around 2 to 3 inches is used.

A circuit board 317 is provided on the inside of the main body case 360. A memory device 335 such as a recording medium and a media slot is mounted or attachable with respect to the circuit board 317, and records the image information of the subject including the still picture and moving picture which are obtained by the normal mode or the special moving picture recording mode and the sound information of the ambient sound of the subject when obtaining the moving picture. On the circuit board 317, there are mounted the information-processing unit 315 other than the memory device 335.

On the inside of main body case 360, a battery 314 is mounted other than the circuit board 317 and supplies DC power to the circuit board 317, the display unit 329, the imaging unit 334, the memory device 335 and the living-body sensor unit 345. An external interface 341 is provided on the external side of the main body case 360 and can be connected to connectors for image and sound, a communication cable or the like from an external apparatus. The external interface 341 is used when executing image and sound output to the external apparatus and a terminal for the communication cable is used when communicating with the external apparatus.

Figure 19:
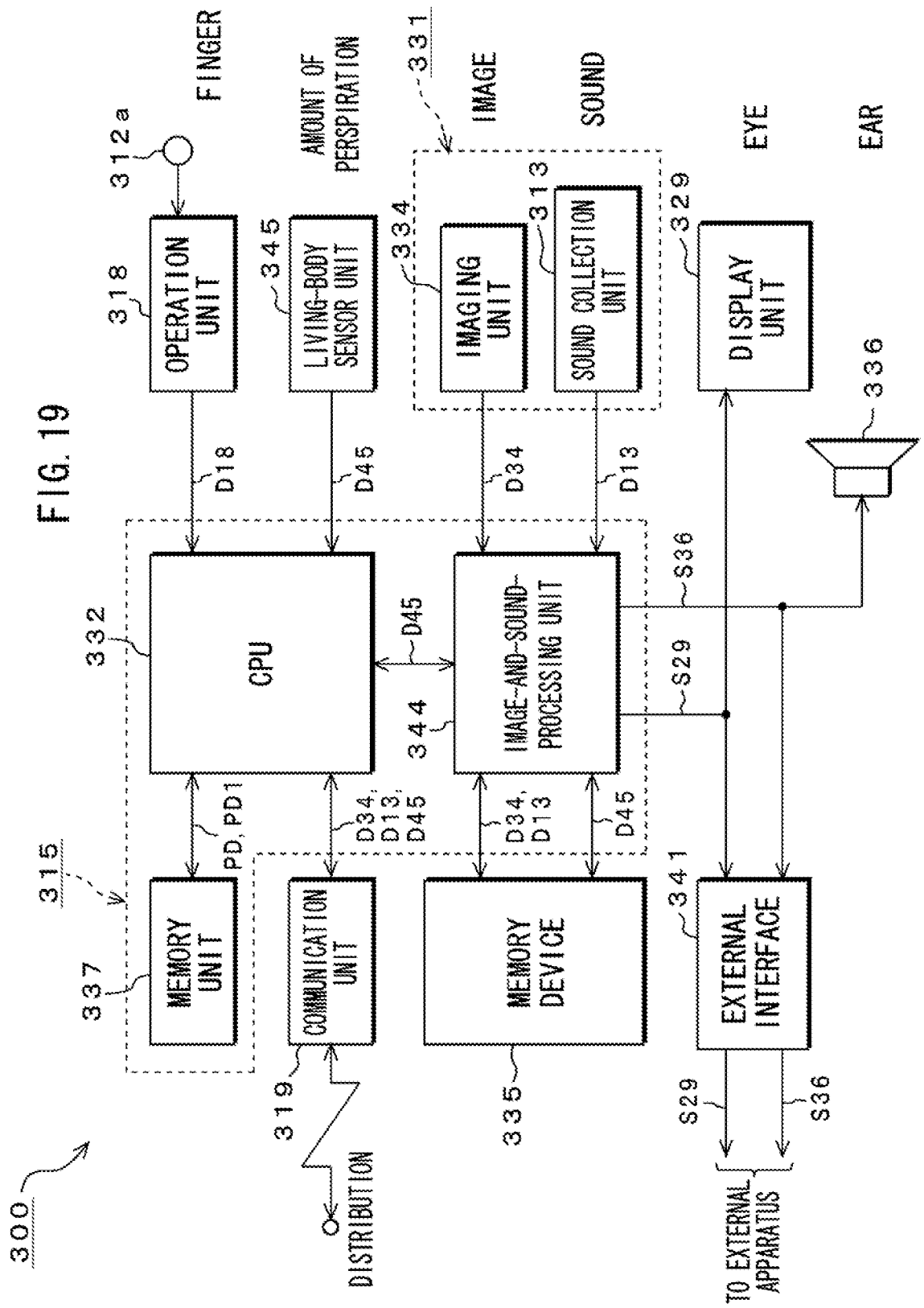
FIG. 19 is a block diagram showing a configuration of a control system of the digital camera 300.

FIG. 19 shows a configuration of a control system of the digital camera 300. The digital camera 300 shown in FIG. 19 is constituted by being mounted with respective function blocks on the circuit board 317 in the main body case 360. It should be noted that in FIG. 19, portions corresponding to respective portions shown in FIG. 18 are denoted as the same reference numerals.

The digital camera 300 contains the shutter switch 312a, the information-processing unit 315, an operation unit 318, a communication unit 319, the display unit 329, an image-and-sound-recording unit 331, the memory device 335, the external interface 341 and the living-body sensor unit 345. The same reference numerals and the same name as the embodiment 1 have the same function, so that the explanation thereof will be omitted.

The information-processing unit 315 contains a CPU 332, a memory unit 337 and an image-and-sound-processing unit 344. The CPU 332 controls the whole of the digital camera 300 based on a system program. The memory unit 337 has a ROM, a RAM and an EEPROM or the like which are not shown. Data PD forming the system program for controlling the whole of the digital camera 300 is stored in the ROM or the EEPROM of the memory unit 337. The RAM, which is not shown, is used as a work memory. The CPU 332 reads the data PD forming the system program out of the ROM or the EEPROM concurrently with the power supply ON to expand it in the RAM, and starts up the system to control the whole of the digital camera 300.

The operation unit 318 is connected to the CPU 332 and outputs operation data D18 generated by pushing down the push-button switch 312 such as the power supply switch, the mode switch, the zoom switch or the shutter switch 312a shown in FIG. 18 to the CPU 332.

The image-and-sound-recording unit 331 contains the sound collection unit 313 and the imaging unit 334, which is similar to the embodiment 1. The sound collection unit 313 is connected with the image-and-sound-processing unit 344 and outputs the sound data D13 obtained by collecting the ambient sound of the subject. The imaging unit 334 is connected with the image-and-sound-processing unit 344 and outputs the image data D34 relating to the still picture and the moving picture which are obtained by shooting the image of the subject.

The living-body sensor unit 345 detects the living-body information showing emotion of the living-body of the operator 130 who operates the image-and-sound-recording unit 331, the operation unit 318 or the like, in particular, the shutter switch 312a to output the emotion data D45. For example, for the living-body sensor unit 345, the perspiration sensor 145a shown in FIG. 2 is used and detects the amount of perspiration of the operator 130 who operates the image-and-sound-recording unit 331 on the time series to output the emotion data D45 to the CPU 332.

Other than the system program, a program for the normal mode and a program for the special moving picture recording mode are described in the ROM or the EEPROM of the above-mentioned memory unit 337. The program for the normal mode, similarly as the system in the past, is a fact that the procedure for recording the still pictures is recorded. The program for a special moving picture recording mode is a computer readable program which is used for moving-picture recording the information obtained by shooting the image of the subject and by collecting the ambient sound of the subject based on the emotion of living-body of the operator 130 in parallel with an acquisition process of still picture of the subject.

The contents thereof are described with a step of obtaining image information by shooting the image of the subject and also, of obtaining sound information by collecting an ambient sound of the subject, when acquiring still picture of the subject; a step of detecting and producing living-body information showing emotion of living-body of an operator who operates the image-and-sound-recording unit 331; and a step of performing automatic extraction processing with establishing the correspondence between the living-body information produced in here and the image information of the subject and/or the sound information of the ambient sound of the subject.

In an embodiment, when data PD1 forming such a program is read out of the ROM or the EEPROM and executed, the CPU 332 can execute an editing process or the like in which the correspondence between the produced emotion data D45 showing the emotion of the living-body of the operator 130 and the image information of the subject and/or the sound information of the ambient sound of the subject, which are shot and collected, is established if processing the information obtained by shooting the image of the subject and by collecting the ambient sound of the subject.

For example, the CPU 332 executes the automatic extraction process so as to establish the correspondence between the emotion data D45 outputted from the living-body sensor unit 345 and the image data D34 of the subject and/or the sound data D13 when recording the ambient sound of the subject, which are outputted from the image-and-sound-recording unit 331, individually independently from an ON-operation of the shutter switch 312a. In an embodiment, the CPU 332 compares the emotion data D45 outputted from the living-body sensor unit 345 with a threshold Hth for discriminating the amount of perspiration, which becomes a discrimination criterion of the emotion data D45, which is similar to the embodiment 1.

By this comparison result, for example, when the living-body sensor unit 345 detects the emotion data D45 of a perspiration level Hx which exceeds the threshold Hth for discriminating the amount of perspiration, by making this as a trigger (editing start point), the CPU 332 starts recording the moving picture so as to extract and cut out the image data D34 of the subject which is displayed on a moving picture monitor and the sound data D13 when recording the ambient sound of the subject, even if the shutter switch 312*a* is not ON-operated. In an embodiment, the moving picture information from the editing start point is recorded independently from the still picture.

Thereafter, when the living-body sensor unit 345 detects the emotion data D45 of the perspiration level Hx which is the threshold Hth for discriminating the amount of perspiration or less, by making this as a trigger (editing end point), the CPU 332 controls the image-and-sound-processing unit 344 so as to end the automatic extraction of the image data D34 of the subject and the sound data D13 when recording the ambient sound of the subject. In an embodiment, the recording ends at the editing end point of the moving picture independently from the still picture.

The image-and-sound-processing unit 344, by receiving a still picture recording control of the CPU 332, for example, compresses still picture data by JPEG compression system and transfers it to the memory device 335. The compression ratio, for example, is to be around 1/10 to 1/100 of the still picture data before compressing. With respect to the moving picture relating to impressive scene, by receiving a moving picture extraction record control of the CPU 332, similarly as the embodiment 1, the image data D34 is compressed with being compliant with MPEG-1 standard and is recorded on the memory device 335.

In an embodiment, the memory unit 337 stores the threshold Hth for discriminating the amount of perspiration. For example, the threshold Hth for discriminating the amount of perspiration is stored in the ROM or the like provided in the memory unit 337 beforehand as a trigger parameter. The RAM of the memory unit 337 receives the emotion data D45 under the memory control of the CPU 332, compares the preset threshold Hth for discriminating the amount of perspiration with the perspiration level Hx obtained from the emotion data D45, and executes a discrimination process of Hth>Hx and a discrimination process of Hth≦Hx or the like. It is needless to say that the threshold of discriminating the amount of perspiration is not limited to an unambiguous constant and it is also allowed to employ a variable which changes in a second order function (see FIG. 5).

By doing in this manner, it becomes possible to extract the specific image and sound corresponding to the amount of perspiration of the finger of the operator 130. The editing start point information and the editing end point information are, for example, set (described) as time codes with respect to the recording time information, which is similar to the embodiment 1, but the format in which the moving picture is cut out at times and stored in the memory device 335 is employed, so that it is also allowed to omit. By the setting of the special moving picture recording mode, it becomes possible to automatically extract the image data D34 and the sound data D13 at a period of time when emotion of the living-body is heightened to sweat in a hand during the time when the operator 130 is shooting the still pictures of the subject.

Further, by possessing a reproduction control function to the CPU 332, it is also allowed to reproduce the image data D34 of the subject and the sound data D13 when recording the ambient sound of the subject of the moving picture scene of the subject which are automatically extracted. When such a reproducing process is executed, the image data D34 and the sound data D13 which form the moving picture scene at a period of time when emotion of the living-body is heightened to sweat in a hand during the time when the operator 130 is shooting the subject still picture can be reproduced, and it becomes possible to view a memorial file on which operator's specific image data D34 and sound data D13 are recorded in addition to the still picture of the subject. The display unit 329 can receive the operator's specific image data D34 and display the operator's specific image, and the speaker 36 to which the sound data D13 of the ambient sound of the subject when capturing the impressive scene is inputted can output the specific ambient sound of the subject or the like.

Further, by possessing a record-on control function to the CPU 332, it is also allowed to record the image data D34 of the subject and the sound data D13 when recording the ambient sound of the subject relating to the moving picture scene of the subject which is automatically extracted on the predetermined recording medium. When such a recording process is executed, it is possible to record the image data D34 and the sound data D13 which form the moving picture scene at a period of time when emotion of the living-body is heightened to sweat in a hand during the time when the operator 130 is shooting the still picture of the subject on the recording medium of the CD-ROM, the MD or the like, and it becomes possible to distribute the memorial file on which the image data D34 and the sound data D13 which form the operator's specific moving picture scene are recorded, in addition to the still picture.

The above-mentioned CPU 332 is connected with the memory device 335 constituting a recording medium (media), a media slot or the like. The memory device 335 stores the moving picture record information which establishes the correspondence between the emotion data D45 produced by detecting the living-body information showing emotion of the living-body of the operator 130 and the image data D34 of the subject and/or the sound data D13 when recording the ambient sound of the subject which are shot and collected, on an occasion of the special moving picture recording mode, other than the still picture information under the normal mode. For the memory device 335, there is used a non volatile memory of a hard disk device, a memory card or the like.

The above-mentioned image-and-sound-processing unit 344 is connected with the display unit 329 which displays a moving picture when being shooting it, a still picture when being reproduced or a moving picture forming impressive scene based on the image display signal S29. The image-and-sound-processing unit 344 is connected with the speaker 336 which outputs ambient sound of the subject when being shooting the moving picture or sound when being reproduced based on the sound signal S36 when being shooting the moving picture. The speaker 336 is provided at a predetermined position of the main body case 360. The image-and-sound-processing unit 344 is connected with the external interface 341 which outputs an image and sound signal to the external apparatus.

The CPU 332 is connected with the communication unit 319 which, similarly as the embodiment 1, communicates with the external apparatus. For example, the CPU 332 controls the communication unit 319 to distribute the image data D34 of the subject and the sound data D13 when recording the ambient sound of the subject which form the automatically extracted moving picture of the subject. When executing such a distributing process, it is possible to distribute the image data D34 and the sound data D13 at the period of time when emotion of the living-body is heightened to sweat in a hand during the time when the operator 130 is shooting the still picture of the subject, and it becomes possible to download a file (algorithm) on which operator's specific image data D34 and sound data D13 are recorded to the other user through the Internet or the like. It should be noted that with respect to shooting format example in the digital camera 300, FIGS. 4A to 4D and FIGS. 5A to 5D should be referred thereto.

Figure 20:
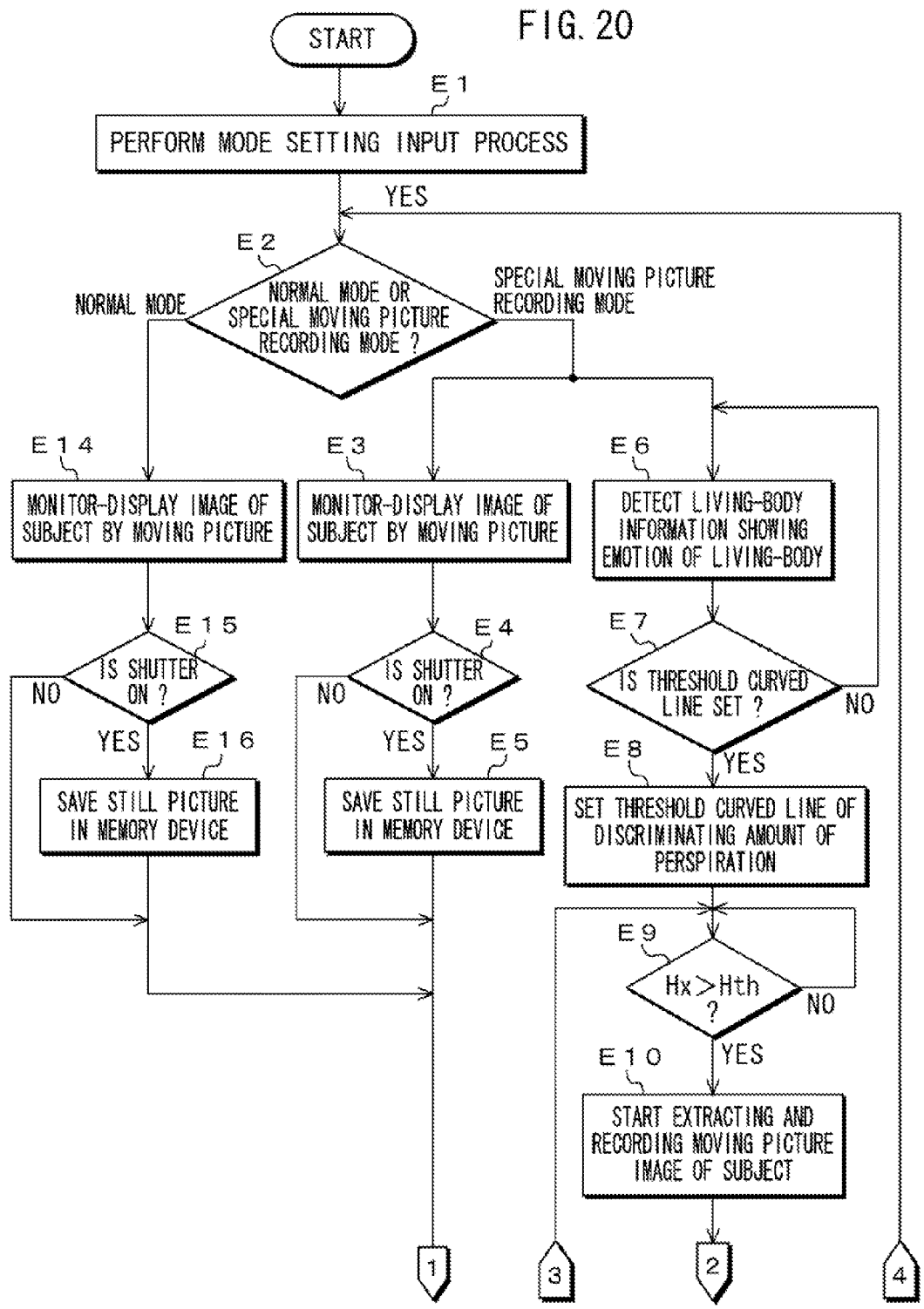
FIG. 20 is a flowchart showing a recording process example (No. 1 thereof) in the digital camera 300.
Figure 21:
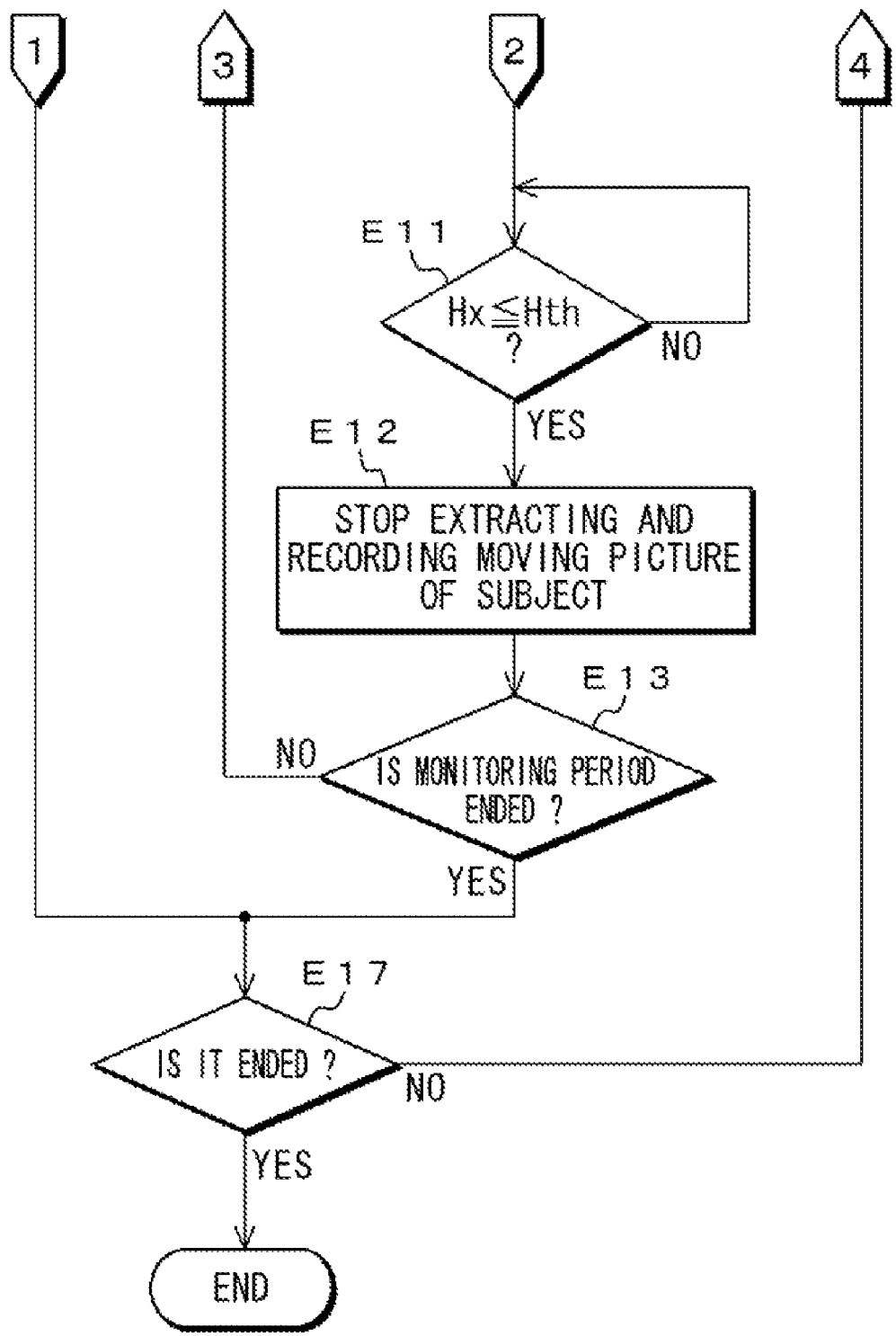
FIG. 21 is a flowchart showing the recording process example (No. 2 thereof) in the digital camera 300.

The following will describe a third embodiment of the information-processing method according to the present application. FIG. 20 and FIG. 21 show recording process examples (No. 1, 2 thereof) in the digital camera 300.

In an embodiment, a case is assumed in which the still picture information and the moving picture information of impressive scene which are obtained by shooting the image of the subject and the sound information obtained by collecting the ambient sound of the subject are processed. For the living-body sensor unit 345, the perspiration sensor 145a as shown in FIG. 2 is used. The CPU 332 executes an automatic extraction process so as to establish the correspondence between the emotion data D45 outputted from the living-body sensor unit 345 and the image data D34 of the subject and/or the sound data D13 when recording the ambient sound of the subject, which are outputted from the image-and-sound-recording unit 331, independently from the ON-operation of the shutter switch 312a.

On the premise of these, the CPU 332 executes a mode setting input process in step E1 of the flowchart shown in FIG. 20. For example, operation data D18 relating to the setting of the normal mode or the special moving picture recording mode is inputted. At that time, the user operates a push-button switch 312 constituting a mode switch to select either one of the normal mode and the special moving picture recording mode. For example, when he or she operates the push-button switch 312 to select the special moving picture recording mode, the operation unit 318 outputs the operation data D18 showing the special moving picture recording mode to the CPU 332.

Next, at step E2, the process is branched by setting the normal mode or the special moving picture recording mode. If the special moving picture recording mode is set in the step E1, the CPU 332 monitor-displays the moving picture relating to the image of the subject at step E3. Then, at step E4, it is monitored whether or not the shutter switch 312a is ON-operated. If the shutter switch 312a is not ON-operated, the monitor display of the moving picture relating to the image of the subject continues and at the same time, the process shifts to step E17. At the step E4, if the shutter switch 312a is ON-operated, the process shifts to step E5 where the still picture of the image of the subject is monitor-displayed and at the same time, the still picture is recorded on the memory device 335 and kept. At that time, the imaging unit 334 shoots the image of the subject and obtains the image data D34. The image-and-sound-processing unit 344 records, for example, the image data D34 in which the still picture information is compressed with being compliant with JPEG standard on the memory device 335. Thereafter, the process shifts to the step E17.

In parallel with this, at step E6, the CPU 332 controls the living-body sensor unit 345 to detect the living-body information showing emotion of the living-body of the operator 130 who operates the digital camera 300 to produce the emotion data D45. The living-body sensor unit 345, by receiving this control, detects the amount of perspiration of the operator touching the perspiration sensor 145a to output the emotion data D45 showing a perspiration level to the CPU 332.

Next, at step E7, the CPU 332 judges whether or not the threshold curved line of discriminating the amount of perspiration is set. With respect to the discrimination criterion in this case, similarly as the embodiment 1, it is executed by comparing the change rate (emotion change rate) of the amount of perspiration of the operator, which is detected by the living-body sensor unit 345, with a reference change rate which becomes a setting reference of the preset threshold curved line. The change rate of the amount of perspiration of the operator is a difference between the amounts of perspiration detected at two points of sampling time on and after the point of time when the living-body sensor unit 345 detects some sort of amount of perspiration of the operator. The reason for obtaining such a difference is just as explained in the embodiment 1.

At the above-mentioned step E7, when the change rate of the amount of perspiration of the operator exceeds the reference change rate, at step E8, the CPU 332 sets the threshold curved line of discriminating the amount of perspiration. At that time, the threshold curved line of discriminating the amount of perspiration as shown in formula (1) is read out of the memory unit 337 and is expanded in the RAM. Concurrently with this, the CPU 332 activates a timer, and starts the count of the period of monitoring time. Then, the process shifts to step E9 where the CPU 332 executes the discrimination process of Hx>Hth by comparing the emotion data D45 outputted from the living-body sensor unit 345 with the threshold Hth for discriminating the amount of perspiration which becomes the discrimination criterion of the emotion data D45. The memory unit 337, by receiving the memory control of the CPU 332 shown in FIG. 19, receives the emotion data D45 and the thresholds Hth1, Hth2, Hth3, Hth4 and so on of discriminating the amount of perspiration, which form the preset threshold curved line of discriminating the amount of perspiration, are compared with the perspiration level Hx obtained from the emotion data D45.

When the discrimination result such as Hx>Hth is obtained, the process shifts to step E10 where the CPU 332 starts the extracting recording process of the moving picture of the subject at a point of time ts showing the editing start point without having relation with the ON-operation of the shutter switch 312a at the step E4. At that time, the image-and-sound-processing unit 344 compresses the image data D34 of the subject and the sound data D13 when recording the ambient sound of the subject of the editing start point with being compliant with MPEG standard. The image data D34 of the subject and the sound data D13 when recording the ambient sound of the subject after the compression processing are stored so as to be moving-picture recorded in the memory device 335 (see FIG. 5).

Then, the process shifts to step E11 shown in FIG. 21 where the CPU 332 executes the discrimination process of Hx≦Hth. If the Hx≦Hth is discriminated, the process shifts to step E12, and the extracting recording process of the moving picture of the subject ends at a point of time te showing the editing end point without having relation with the ON-operation of the shutter switch 312a at the step E4. At that time, the image data D34 of the subject and the sound data D13 when recording the ambient sound of the subject on and after the editing end point is stayed in the display processing until the next discrimination result of Hx>Hth is obtained without recording them on the memory device 335.

In the image-and-sound-processing unit 344, by the moving picture extraction record control from the CPU 332, the moving picture scene between the point of time ts showing the editing start point and the point of time te showing the editing end point, which are extracted, becomes a first extracted (picking) scene Sv (image and sound information for edition) in the special moving picture recording mode (see FIG. 5).

Thereafter, the process shifts to step E13, similarly as the embodiment 1, where it is judged whether or not the monitoring period ends in the threshold curved line of discriminating the amount of perspiration. With reference to the judgment criterion in this case, it ends by the counting-up of the timer. When the monitoring period does not end, the process returns to the step E9 where the CPU 332 executes the discrimination process of Hx>Hth by comparing the emotion data D45 outputted from the living-body sensor unit 345 with the threshold Hth for discriminating the amount of perspiration which becomes the discrimination criterion of the emotion data D45.

By this moving picture extraction record control, it becomes possible to automatically extract the image data D34 and the sound data D13 at the period of time when emotion of the living-body is heightened to sweat in a hand during the time when the operator 130 is shooting the still picture of the subject without having relation with the ON-operation of the shutter switch 312a. When the above-mentioned period of monitoring time ends, the process shifts to the step E17.

It should be noted that when the normal mode is set at the step E2, the process shifts to the step E14 where the normal mode is executed. In the normal mode, the image of the subject is monitor-displayed at the step E14 without executing the detection processing or the like of the living-body information. Then, at step E15, it is monitored whether or not the shutter switch 312a is ON-operated. When the shutter switch 312a is not ON-operated, the monitor display of the image of the subject by the moving picture is continued and at the same time, the process shifts to the step E17. When the shutter switch 312a is ON-operated at the step E15, the process shifts to step E16 where the still picture of the subject is monitor-displayed and at the same time, the still picture is recorded on the memory device 335 and kept. At that time, similarly as the previous step E5, the imaging unit 334 shoots the image of the subject and obtains the image data D34. The image-and-sound-processing unit 344 records the image data D34 in which the still picture information is compressed with being compliant with JPEG standard on the memory device 335. Thereafter, the process shifts to the step E17.

At the step E17, the CPU 332 judges the end. For example, the CPU 332 judges whether or not the push-button switch 312 constituting the power supply switch is operated and the power-off information is detected. When the push-button switch 312 constituting the power supply switch is operated and the power-off information is detected, the still picture and moving picture recording processing ends. When the push-button switch 312 constituting the power supply switch is not operated and the power-off information is not detected, the process returns to the step E2 where the above-mentioned processes are repeated. Thus, independently from the ON-operation of the shutter switch 312a, it becomes possible to store on the memory device 335 the data which establishes the correspondence between the emotion data D45 obtained from the living-body sensor unit 345 and the image data D34 of the subject and/or the sound data D13 when recording the ambient sound of the subject which are shot and collected, and to performs moving-picture-recording process.

In this manner, according to the digital camera and the information-processing method as the third embodiment, when processing the still picture information and the moving picture information of impressive scene obtained by shooting the image of the subject and the sound information obtained by collecting the ambient sound of the subject, the imaging unit 334 outputs the image data D34 obtained by shooting the image of the subject corresponding to the ON-operation of the shutter switch 312a to the image-and-sound-processing unit 344, during the time when acquiring the still picture. The living-body sensor unit 345 detects the living-body information showing emotion of the living-body of the operator 130 who operates the image-and-sound-recording unit 331 without having relation with the ON-operation of the shutter switch 312a to output the emotion data D45. On the premise of this, the CPU 332 performs automatic-extraction-process on the moving picture which establishes the correspondence between the emotion data D45 outputted from the living-body sensor unit 345 and the image data D34 of the subject and/or the sound data D13 when recording the ambient sound of the subject which are outputted from the image-and-sound-recording unit 331.

Consequently, it becomes possible to automatically extract the image data D34 and the sound data D13 at the period of time when emotion of the living-body is heightened to sweat in a hand during the time when the operator 130 is shooting the still picture of the subject, thereby enabling the operator's specific image and sound data file relating to moving picture in which the automatically extracted image data D34 and sound data D13 are edited to be easily and also simply produced.

Furthermore, the still picture of the miss-shot impressive scene by the ON-operation of the shutter switch 312a can be automatically extracted as the moving picture of the impressive scene and at a later date, it becomes possible to edit the still picture thereof from the moving picture of the impressive scene. Consequently, other than the still picture obtained by the ON-operation of the shutter switch 312a, it becomes possible to edit (acquire) the more unique JPEG still picture of the impressive scene among the automatically extracted moving pictures of the impressive scene.

Embodiment 4

Figure 22:
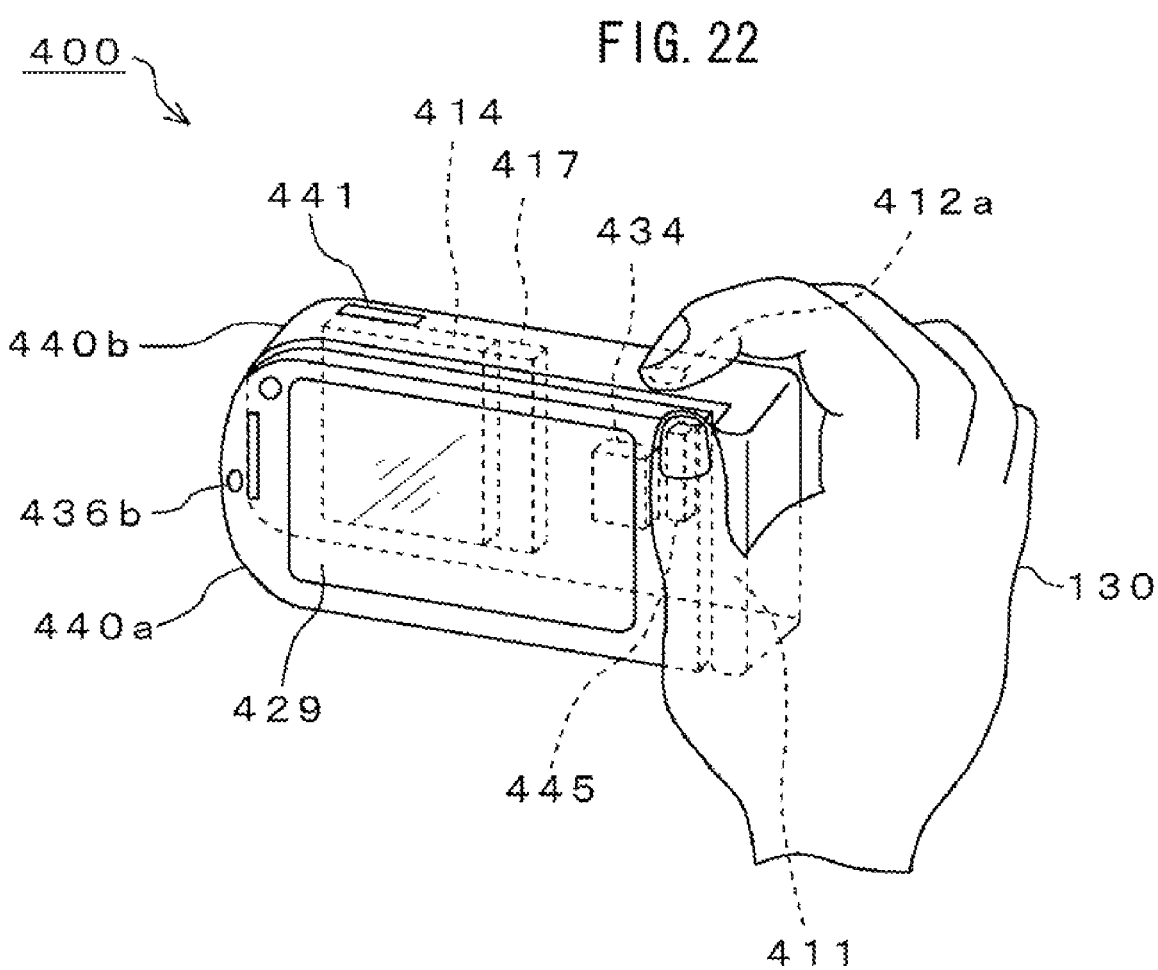
FIG. 22 is a perspective view of a mobile phone 400 with camera as a fourth embodiment for showing a configuration thereof.

FIG. 22 shows a configuration of a mobile phone 400 with camera as a fourth embodiment. The mobile phone 400 shown in FIG. 22 has a digital camera function mode and at the same time, has an upper housing 440a and a lower housing 440b. The upper housing 440a and the lower housing 440b are connected rotatably and folded with a hinge mechanism 411 intervening between them.

A display unit 429 is provided on the front surface of the upper housing 440a and displays an image of the subject by moving picture when executing a digital camera function mode. When executing a telephone function mode, the display unit 429 displays a telephone number of the partner or menu screens. A speaker 436b is provided on the upside of the front surface of the upper housing 440a and is used for a receiver for call. A living-body sensor unit 445 is provided at the attachment position of the hinge mechanism 411 facing the attachment position of the speaker 436b, and detects living-body information showing emotion of the living-body of the operator 130 who operates the mobile phone 400 to output the living-body information.

An operation unit, which is not shown, constituted by a plurality of push-button switches is provided at the lower housing 440b which is movably connected by the hinge mechanism 411 with respect to the upper housing 440a. The push-button switches are constituted by [0] to [9] numeral keys, symbol keys of [*], [#] and the like, hook buttons of [ON], [OFF] or the like, menu key or the like. A shutter switch 412a is provided on the side surface (upper portion in the drawing) of the lower housing 440b. A microphone 413 for call, which is not shown in FIG. 22, is mounted in a portion of the lower housing 440b under the operation panel screen and functions as a transmitter.

Also, an imaging unit 434 is provided on the rear surface side of the lower housing 440b and shoots a subject by an ON-operation of the shutter switch 412a to acquire, for example, still picture information or operation information. In the inside of the lower housing 440b, there are provided a battery 414, a circuit board 417 and the like. A module type antenna 416, which is not shown, is mounted on the inside of lower end of the lower housing 440b. A speaker 436a for big sound is provided at the upper end inside side surface thereof and releases reproduction sound or the like.

Figure 23:
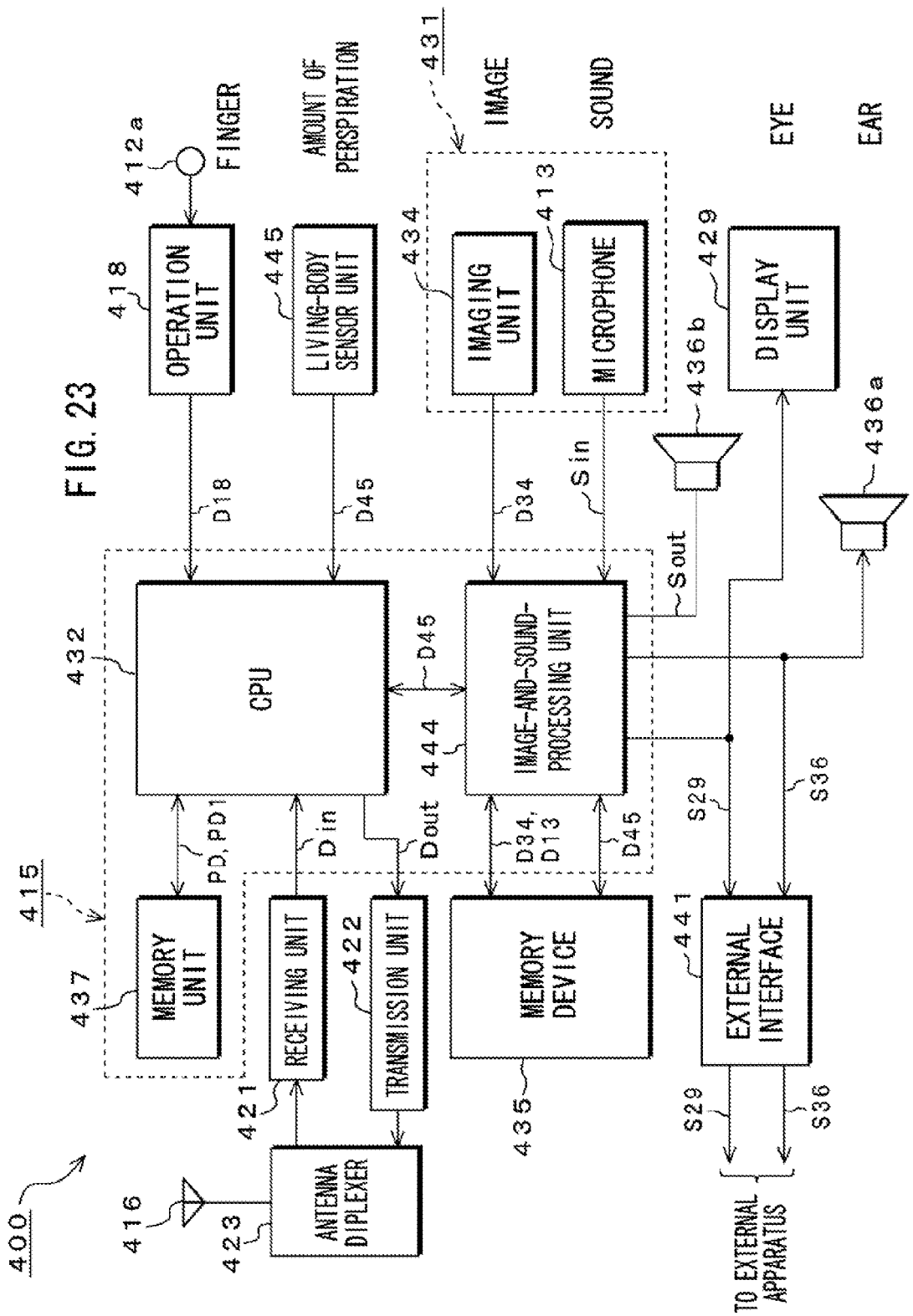
FIG. 23 is a block diagram showing a configuration of a control system of the mobile phone 400.

FIG. 23 shows a configuration of a control system of the mobile phone 400. The mobile phone 400 shown in FIG. 23 is constituted by being mounted with respective function blocks on the circuit board 417 in the lower housing 440b. It should be noted that in FIG. 23, portions corresponding to respective portions shown in FIG. 22 are denoted as the same reference numerals. The mobile phone 400 contains an information-processing unit 415, the antenna 416, the operation unit 418, a receiving unit 421, a transmission unit 422, an antenna diplexer 423, the display unit 429, an image-and-sound-recording unit 431, a memory device 435, speakers 436a, 436b, an external interface 441 and the living-body sensor unit 445.

The information-processing unit 415 contains a CPU 432, a memory unit 437 and an image-and-sound-processing unit 444. The CPU 432 controls the whole of the mobile phone 400 based on a system program. The memory unit 437 has a ROM, a RAM and an EEPROM or the like, which are not shown. Data PD forming the system program for controlling the whole of the mobile phone is stored in the ROM or the EEPROM of the memory unit 437. The RAM, which is not shown, is used for a work memory. The CPU 432 reads the data PD forming the system program out of the ROM or the EEPROM concurrently with the power supply ON to expand it in the RAM, and starts up the system to control the whole of the mobile phone 400.

Other than the system program, a program for a shooting record mode is described in the ROM or the EEPROM of the memory unit 437. The program for the shooting record mode includes a program for executing a still picture recording mode and a special moving picture recording mode. The program for the still picture recording mode, similarly as the system in the past, is a fact that the procedure for recording the still pictures is recorded. The program for the special moving picture recording mode is a computer readable program which is used for moving-picture recording the information obtained by shooting the image of the subject and by collecting ambient sound of the subject based on the emotion of the living-body of the operator 130 in parallel with an acquisition process of still picture of the subject.

The contents thereof are described with a step of obtaining image information by shooting the image of the subject and also, of obtaining sound information by collecting ambient sound of the subject, when acquiring still picture of the subject; a step of detecting and producing living-body information showing emotion of living-body of an operator who operates the image-and-sound-recording unit 431; and a step of performing automatic extraction processing with establishing the correspondence between the living-body information produced in here and the video information of the subject and/or the sound information of the ambient sound of the subject.

In an embodiment, on a occasion of the selection of the digital camera function mode, when data PD1 forming such a program is read out of the ROM or the EEPROM and executed, the CPU 432 can execute an editing process or the like in which the correspondence between the produced emotion data D45 showing the emotion of the living-body of the operator 130 and the image information of the subject and/or the sound information of the ambient sound of the subject, which are shot and collected, is established if processing the information obtained by shooting the image of the subject and by collecting the ambient sound of the subject.

The CPU 432 is connected with the operation unit 418 which outputs to the CPU 432 operation data D18 generated by pushing down the push-button switch such as a power supply switch, a mode switch, a zoom switch, and a shutter switch 412a when operating the mobile phone.

The CPU 432 is connected with the image-and-sound-recording unit 431 other than the operation unit 418. The image-and-sound-recording unit 431 contains a microphone 413 and an imaging unit 434. The microphone 413 is connected with the image-and-sound-processing unit 444 and outputs a sound signal Sin obtained by collecting ambient sound of the subject or operator's talking voice. The image-and-sound-processing unit 444 converts the sound signal Sin outputted from the microphone 413 from analog to digital, and outputs sound data D13 to a transmission unit 422, a memory device 435 or the like. For the microphone 413, there is used a microphone of the model explained in the embodiment 1. The imaging unit 434 is connected with the image-and-sound-processing unit 444 and outputs image data D34 obtained by shooting the image of the subject when selecting the digital camera function mode. The inside structure of the imaging unit 434 is explained in the embodiment 1, so that it is omitted.

The CPU 432 is connected with a living-body sensor unit 445, other than the image-and-sound-recording unit 431, which detects living-body information showing emotion of living-body of an operator 130 who operates the image-and-sound-recording unit 431 to output emotion data D45. For example, for the living-body sensor unit 445, there is used the perspiration sensor 145a shown in FIG. 2, which detects the amount of perspiration of the operator 130 who operates the image-and-sound-recording unit 431 on the time series to output the emotion data D45 to the CPU 432.

The CPU 432, similarly as a case of the digital camera function explained in the embodiment 3, executes the automatic extraction process so as to establish the correspondence between the emotion data D45 outputted from the living-body sensor unit 445 and the image data D34 of the subject and/or the sound data D13 when recording the ambient sound of the subject, which are outputted from the image-and-sound-recording unit 431, individually independently from an ON-operation of the shutter switch 412a. In an embodiment, the CPU 432 compares the emotion data D45 outputted from the living-body sensor unit 445 with a threshold Hth for discriminating the amount of perspiration, which becomes a discrimination criterion of the emotion data D45, which is similar to the embodiment 1.

By this comparison result, for example, when the living-body sensor unit 445 detects the emotion data D45 of a perspiration level Hx which exceeds the threshold Hth for discriminating the amount of perspiration, by making this as a trigger (editing start point), the CPU 432 starts recording the moving picture so as to extract and cut out the image data D34 of the subject which is displayed on a moving picture monitor and the sound data D13 when recording the ambient sound of the subject, even if the shutter switch 412a is not ON-operated. In an embodiment, the moving picture information from the editing start point is recorded independently from the still picture.

Thereafter, when the living-body sensor unit 445 detects the emotion data D45 of the perspiration level Hx which is the threshold Hth for discriminating the amount of perspiration or less, by making this as a trigger (editing end point), the CPU 432 controls the image-and-sound-processing unit 444 so as to end the automatic extraction of the image data D34 of the subject and the sound data D13 when recording the ambient sound of the subject. In an embodiment, the recording ends at the editing end point of the moving picture independently from the still picture.

The image-and-sound-processing unit 444, by receiving a still picture recording control of the CPU 432, for example, compresses still picture data by JPEG compression system and transfers it to the memory device 435. The compression ratio, for example, is to be around $1/10$ to $1/100$ of the still picture data before compressing. With respect to the moving picture relating to impressive scene, by receiving a moving picture extraction record control of the CPU 432, similarly as the embodiment 1, the image data D34 is compressed with being compliant with MPEG-1 standard and is recorded on the memory device 435.

In an embodiment, the memory unit 437 stores the threshold Hth for discriminating the amount of perspiration. For example, the threshold Hth for discriminating the amount of perspiration is stored in the ROM or the like provided in the memory unit 437 beforehand as a trigger parameter. The RAM of the memory unit 437 receives the emotion data D45 under the memory control of the CPU 432, compares the preset threshold Hth for discriminating the amount of perspiration with the perspiration level Hx obtained from the emotion data D45, and executes a discrimination process of Hth>Hx and a discrimination process of Hth≦Hx or the like. It is needless to say that the threshold of discriminating the amount of perspiration is not limited to an unambiguous constant and it is also allowed to employ a variable which changes in a second order function (see FIG. 5).

By doing in this manner, in also the mobile phone 400, it becomes possible to extract the specific image and sound corresponding to the amount of perspiration of the finger of the operator 130. The editing start point information and the editing end point information are, for example, set (described) as time codes with respect to the recording time information, which is similar to the embodiment 1, but the format in which the moving picture is cut out at times and stored in the memory device 435 is employed, so that it is also allowed to omit. By the setting of the shooting record mode, it becomes possible to automatically extract the image data D34 and the sound data D13 at a period of time when emotion of the living-body is heightened to sweat in a hand during the operator 130 is shooting the still pictures of the subject.

The above-mentioned CPU 432 is connected with the memory device 435 constituting a recording medium (media), a media slot or the like and on an occasion of the shooting record mode, the record information is stored, which establishes the correspondence between the emotion data D45 produced by detecting the living-body information showing emotion of the living-body of the operator 130 and the image data D34 of the subject and/or the sound data D13 when recording the ambient sound of the subject which are shot and collected. For the memory device 435, there is used a non volatile memory of a hard disk device, a memory card or the like.

Also, as a mobile phone specific component, the antenna 416 shown in FIG. 23 is connected to the antenna diplexer 423 and receives a radio wave from a base station or the like of the partner when receiving a call. The receiving unit 421 is connected to the antenna diplexer 423, receives receiving data that is introduced from the antenna 416, demodulation-processes image, sound and the like, and outputs image and sound data Din after the demodulation to the CPU 432 or the like. The receiving unit 421 is connected with the image-and-sound-processing unit 444 through the CPU 432 in which the digital sound data Din is D/A converted to a sound signal Sout to be outputted and the digital image data is D/A converted to an image display signal S29 to be outputted.

The above-mentioned image-and-sound-processing unit 444 is connected with the display unit 429 which displays an image when being shooting it, an image when being reproduced based on the image display signal S29. The image-and-sound-processing unit 444 is connected with the speaker 436*a* for big sound which outputs melody signaling incoming call or sound when being reproduced based on the sound signal S36. The speaker 436*a* is provided at a predetermined position of the lower housing 440*b*. The image-and-sound-processing unit 444 is connected with the speaker 436*a* constituting a receiver other than the speaker 436*a*. The speaker 436*b* amplifies a talk of the partner by receiving the sound signal Sout. The speaker 436*b* is provided at a predetermined position of the upper housing 440*a*.

This image-and-sound-processing unit 444 is connected with the microphone 413 constituting a transmitter which collects a voice of the operator 130 to output a sound signal Sin, other than the speakers 436*a*, 436*b*. The image-and-sound-processing unit 444, when call-transmitting, converts the analogue sound signal Sin for transmitting to the partner to digital sound data Dout and outputs it.

The CPU 432 is connected with the transmission unit 422, other than the receiving unit 421, which performs modulation on the image and sound data Dout or the like for transmitting it to the partner and supplies the transmitting data after the modulation to the antenna 416 through the antenna diplexer 423. The antenna 416 radiates the radio wave supplied from the antenna diplexer 423 toward a base station and the like.

In an embodiment, it is also possible to distribute the image data D34 of the subject and the sound data D13 when recording the ambient sound of the subject which are obtained based on the automatic extraction process in the mobile phone 400 through the transmission unit 422. When executing such a distribution process, it is possible to distribute the image data D34 of the subject and the sound data D13 when recording the ambient sound of the subject at a period of time when emotion of the living-body is heightened to sweat in a hand during the time when the operator 130 is shooting the image of the subject, thereby enabling a file (algorithm) on which operator's specific image data D34 and sound data D13 are recorded to be downloaded to the other user through the Internet or the like.

The image-and-sound-processing unit 444 is connected with the external interface 441, other than the microphone 413, which outputs image and sound signals to an external apparatus such as a personal computer and communicates the external apparatus. In an embodiment, it is also allowed for the CPU 432 to possess an editing control function, a reproduction control function, a moving picture distribution control function or the like as explained in the embodiment 1.

Figure 24:
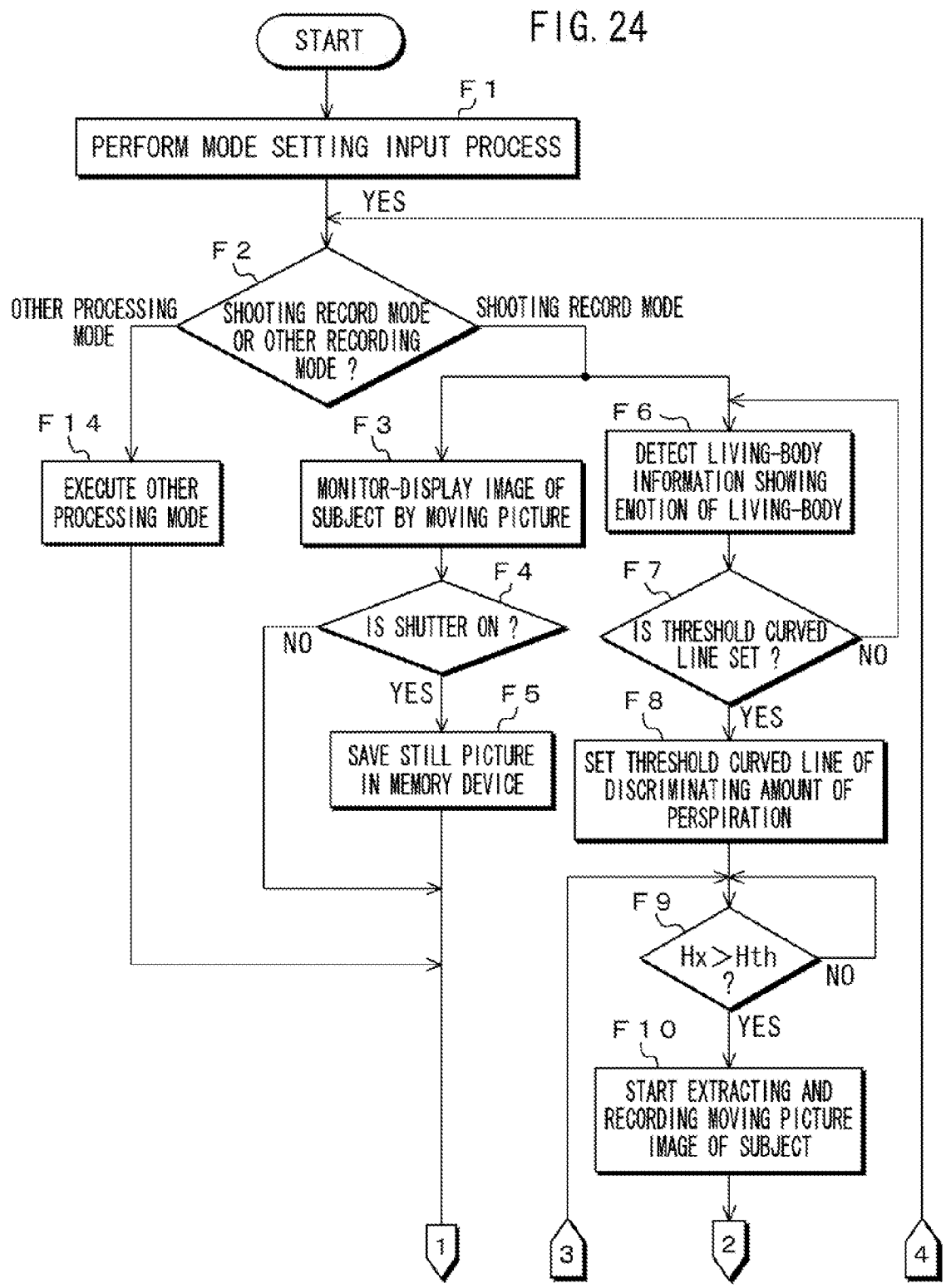
FIG. 24 is a flowchart showing an information processing example (No. 1 thereof) in the mobile phone 400.
Figure 25:
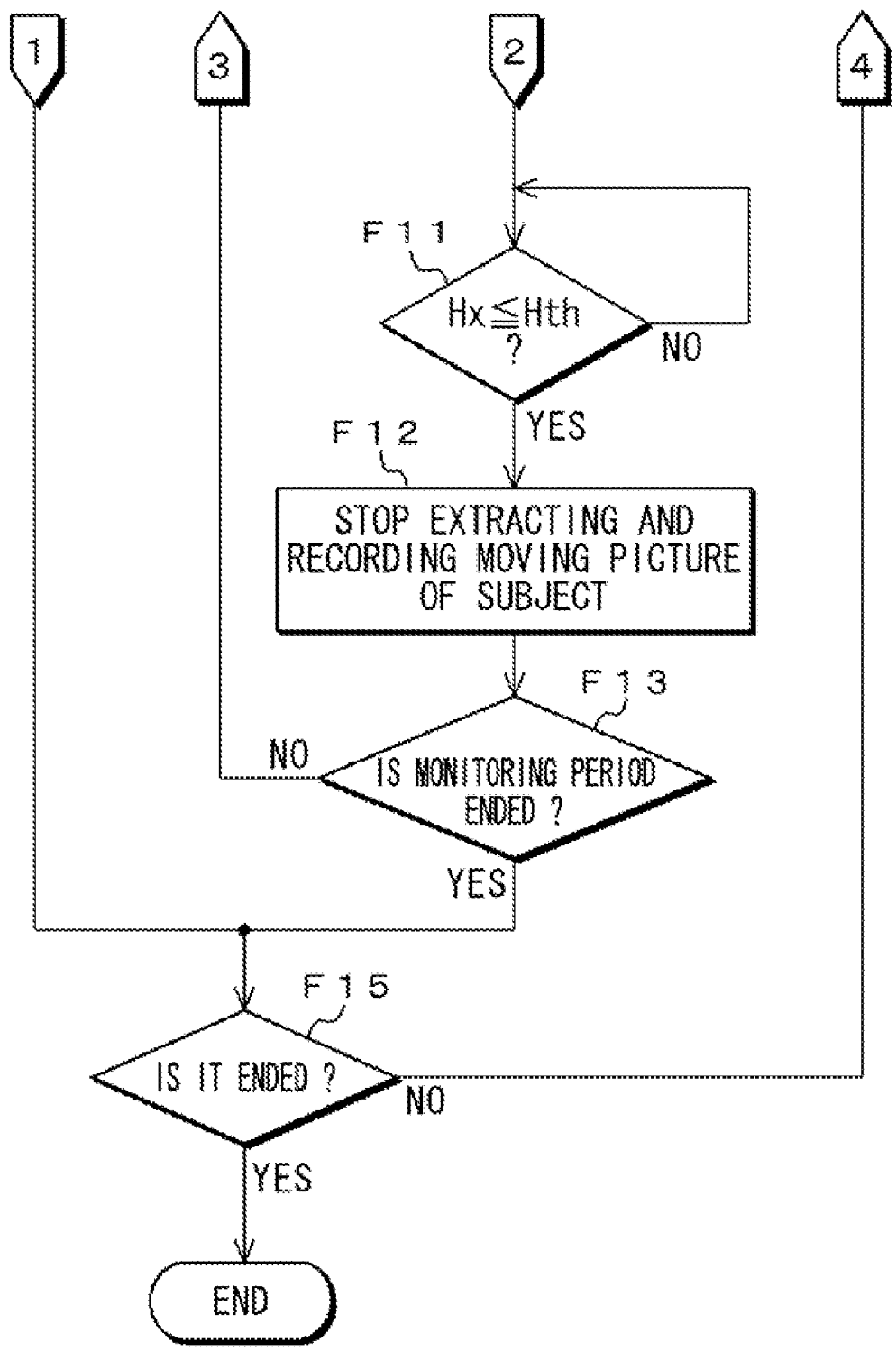
FIG. 25 is a flowchart showing the information processing example (No. 2 thereof) in the mobile phone 400.

The following will describe an information-processing example in the mobile phone 400. FIG. 24 and FIG. 25 show information-processing examples (No. 1, 2 thereof) in the mobile phone 400.

In an embodiment, a case is assumed in which either the shooting record mode or the other processing mode is selected and when the shooting record mode is selected, the recording process combined with the still picture shooting mode and the special moving picture recording mode is executed. In the other processing mode, telephone call transmission, call reception, call-reply function, a shooting mode of only the still picture like a mobile phone of the past system are included.

On the premise of these information-processing conditions, at step F1 in a flowchart shown in FIG. 24, the CPU 432 executes the mode setting input process. For example, operation data D18 relating to the setting of the shooting record mode or the other processing mode is inputted. At that time, the user operates a push-button switch 412 constituting a mode switch to select either one of the shooting record mode and the other processing mode. For example, when he or she operates the push-button switch 412 to select the shooting record mode, the operation unit 418 outputs the operation data D18 showing the shooting record mode to the CPU 432.

Next, at step F2, the process is branched by setting the shooting record mode or the other processing mode. If the shooting record mode is set in the step F1, the CPU 432 monitor-displays the moving picture relating to the image of the subject at step F3. Then, at step F4, it is monitored whether or not the shutter switch 412a is ON-operated. If the shutter switch 412a is not ON-operated, the monitor display of the moving picture relating to the image of the subject continues and at the same time, the process shifts to step F15. At the step F4, if the shutter switch 412a is ON-operated, the process shifts to step F5 where the still picture of the image of the subject is monitor-displayed and at the same time, the still picture is recorded on the memory device 435 and kept. At that time, the imaging unit 434 shoots the image of the subject and obtains the image data D34. The image-and-sound-processing unit 444 records, for example, the image data D34 in which the still picture information is compressed with being compliant with JPEG standard on the memory device 435. Thereafter, the process shifts to the step F15.

In parallel with this, at step F6, the CPU 432 controls the living-body sensor unit 445 to detect the living-body information showing emotion of the living-body of the operator 130 who operates mobile phone 400 to produce the emotion data D45. The living-body sensor unit 445, by receiving this control, detects the amount of perspiration of the operator touching the perspiration sensor 145a to output the emotion data D45 showing a perspiration level to the CPU 432.

Next, at step F7, the CPU 432 judges whether or not the threshold curved line of discriminating the amount of perspiration is set. With respect to the discrimination criterion in this case, similarly as the embodiment 1, it is executed by comparing the change rate (emotion change rate) of the amount of perspiration of the operator, which is detected by the living-body sensor unit 445, with a reference change rate which becomes a setting reference of the preset threshold curved line. The change rate of the amount of perspiration of the operator is a difference between the amounts of perspiration detected at two points of sampling time on and after the point of time when the living-body sensor unit 445 detects some sort of amount of perspiration of the operator. The reason for obtaining such a difference is just as explained in the embodiment 1.

At the above-mentioned step F7, when the change rate of the amount of perspiration of the operator exceeds the reference change rate, at step F8, the CPU 432 sets the threshold curved line of discriminating the amount of perspiration. At that time, the threshold curved line of discriminating the amount of perspiration as shown in formula (1) is read out of the memory unit 437 and is expanded in the RAM. Concurrently with this, the CPU 432 activates a timer, and starts the count of the period of monitoring time. Then, the process shifts to step F9 where the CPU 432 executes the discrimination process of $Hx > Hth$ by comparing the emotion data D45 outputted from the living-body sensor unit 445 with the threshold Hth for discriminating the amount of perspiration which becomes the discrimination criterion of the emotion data D45. The memory unit 437, by receiving the memory control of the CPU 432 shown in FIG. 23, receives the emotion data D45 and the thresholds Hth1, Hth2, Hth3, Hth4 and so on of discriminating the amount of perspiration, which form the preset threshold curved line of discriminating the amount of perspiration, are compared with the perspiration level Hx obtained from the emotion data D45.

When the discrimination result such as $Hx > Hth$ is obtained, the process shifts to step F10 where the CPU 432 starts the extracting recording process of the moving picture of the subject at a point of time ts showing the editing start point without having relation with the ON-operation of the shutter switch 412a at the step F4. At that time, the image-and-sound-processing unit 444 compresses the image data D34 of the subject and the sound data D13 when recording the ambient sound of the subject of the editing start point with being compliant with MPEG standard. The image data D34 of the subject and the sound data D13 when recording the ambient sound of the subject after the compression processing are stored so as to be moving-picture recorded in the memory device 435 (see FIG. 5).

Then, the process shifts to step F11 shown in FIG. 25 where the CPU 432 executes the discrimination process of $Hx \leq Hth$. If the $Hx \leq Hth$ is discriminated, the process shifts to step F12, and the extracting recording process of the moving picture of the subject ends at a point of time te showing the editing end point without having relation with the ON-operation of the shutter switch 412a at the step F4. At that time, the image data D34 of the subject and the sound data D13 when recording the ambient sound of the subject on and after the editing end point is stayed in the display processing until the next discrimination result of $Hx > Hth$ is obtained, without recording them on the memory device 435.

In the image-and-sound-processing unit 444, by the moving picture extraction record control from the CPU 432, the moving picture scene between the point of time ts showing the editing start point and the point of time te showing the editing end point which are extracted becomes a first extracted (picking) scene Sv (image and sound information for edition) in the shooting record mode (see FIG. 5).

Thereafter, the process shifts to step F13, similarly as the embodiment 1, where it is judged whether or not the monitoring period ends in the threshold curved line of discriminating the amount of perspiration. With reference to the judgment criterion in this case, it ends by the counting-up of the timer. When the monitoring period does not end, the process returns to the step F9 where the CPU 432 executes the discrimination process of $Hx > Hth$ by comparing the emotion data D45 outputted from the living-body sensor unit 445 with the threshold Hth for discriminating the amount of perspiration which becomes the discrimination criterion of the emotion data D45.

By this moving picture extraction record control, it becomes possible to automatically extract the image data D34 and the sound data D13 at the period of time when emotion of the living-body is heightened to sweat in a hand during the time when the operator 130 is shooting the still picture of the subject without having relation with the ON-operation of the shutter switch 412a. When the above-mentioned period of monitoring time ends, the process shifts to the step F15.

It should be noted that when the other processing mode is set at the step F2, the process shifts to the step F14 where the other processing mode is executed. In the other processing mode, the telephone function mode or the shooting record mode without accompanying with the special moving picture shooting mode is executed without executing the detection processing or the like of the living-body information showing emotion of the living-body. The shooting record mode without accompanying with the special moving picture shooting mode means the shooting mode of the still picture by the normal mode as explained in the embodiment 3.

For example, when the telephone function mode is selected and telephone call is made to the partner, at first, the telephone number of the partner is read out to the RAM and the telephone of the partner is call-transmitted. When a telephone line of the partner is connected, the microphone 413 constituting a transmitter collects a sound of the operator and outputs it to the image-and-sound-processing unit 444.

The image-and-sound-processing unit 444 converts the sound signal Sin obtained by collecting a talking voice of the operator from analog to digital (A/D). Sound data D13 after the A/D conversion is outputted to the transmission unit 422. The transmission unit 422 performs modulation process on the sound data Dout for the transmitting to the partner, and supplies transmitting data after the modulation to the antenna 416 through the antenna diplexer 423. The antenna 416 radiates a radio wave supplied from the antenna diplexer 423 toward the base station or the like.

Also, a radio wave from the partner is received from the base station through antenna 416. The receiving data introduced from the antenna 416 is demodulation-processed in the receiving unit 421, and the sound data Din after the demodulation is inputted to the image-and-sound-processing unit 444 through the CPU 432. The digital sound data Din is digital/analog (D/A) converted in the image-and-sound-processing unit 444. The sound signal Sout after the D/A conversion is outputted to the speaker 436b. The speaker 436b receives the sound signal Sout and magnifies the talking voice of the partner. Thus, it becomes possible to talk with the partner. Thereafter, the telephone line is terminated (on hooked) and the telephone function mode ends. Thereafter, the process shifts to the step F15.

At the step F15, the CPU 432 judges the end. For example, the CPU 432 judges whether or not the push-button switch 412 constituting the power supply switch is operated and the power-off information is detected. When the push-button switch 412 constituting the power supply switch is operated and the power-off information is detected, the telephone function mode, the shooting record mode and the like end. When the push-button switch 412 constituting the power supply switch is not operated and the power-off information is not detected, the process returns to the step F2 where the above-mentioned process is repeated or it is made to be a waiting state. Thus, independently from the ON-operation of the shutter switch 412a, like the embodiment 3, it becomes possible to store in the memory device 335 the data which establishes the correspondence between the emotion data D45 obtained from the living-body sensor unit 445 and the image data D34 of the subject and/or the sound data D13 when recording the ambient sound of the subject which are shot and collected, and to perform the moving-picture-recording process.

In this manner, according to the mobile phone with camera and the information-processing method as the fourth embodiment, when processing the still picture information and the moving picture information of impressive scene obtained by shooting the image of the subject and the sound information obtained by collecting the ambient sound of the subject utilizing its digital camera function, the imaging unit 434 outputs the image data D34 obtained by shooting the image of the subject corresponding to the ON-operation of the shutter switch 412a to the image-and-sound-processing unit 444, during the time when acquiring the still picture. The living-body sensor unit 445 detects the living-body information showing emotion of the living-body of the operator 130 who operates the image-and-sound-recording unit 431 without having relation with the ON-operation of the shutter switch 412a to output the emotion data D45. On the premise of this, the CPU 432 performs automatic-extraction-process on the moving picture which establishes the correspondence between the emotion data D45 outputted from the living-body sensor unit 445 and the image data D34 of the subject and/or the sound data D13 when recording the ambient sound of the subject which are outputted from the image-and-sound-recording unit 431.

Consequently, it becomes possible to automatically extract the image data D34 and the sound data D13 at the period of time when emotion of the living-body is heightened to sweat in a hand during the time when the operator 130 is shooting the still picture of the subject, which is similar to the embodiment 3, thereby enabling the operator's specific image and sound data file relating to moving picture in which the automatically extracted image data D34 and sound data D13 are edited to be easily and also simply produced.

Furthermore, the still picture of the miss-shot impressive scene by the ON-operation of the shutter switch 412a can be automatically extracted as the moving picture of the impressive scene, which is similar to the embodiment 3, and at a later date, it becomes possible to edit the still picture thereof from the moving picture of the impressive scene. Consequently, other than the still picture obtained by the ON-operation of the shutter switch 312a, it becomes possible to edit (acquire) the more unique JPEG still picture of the impressive scene among the automatically extracted moving pictures of the impressive scene.

Embodiment 5

Figure 26:
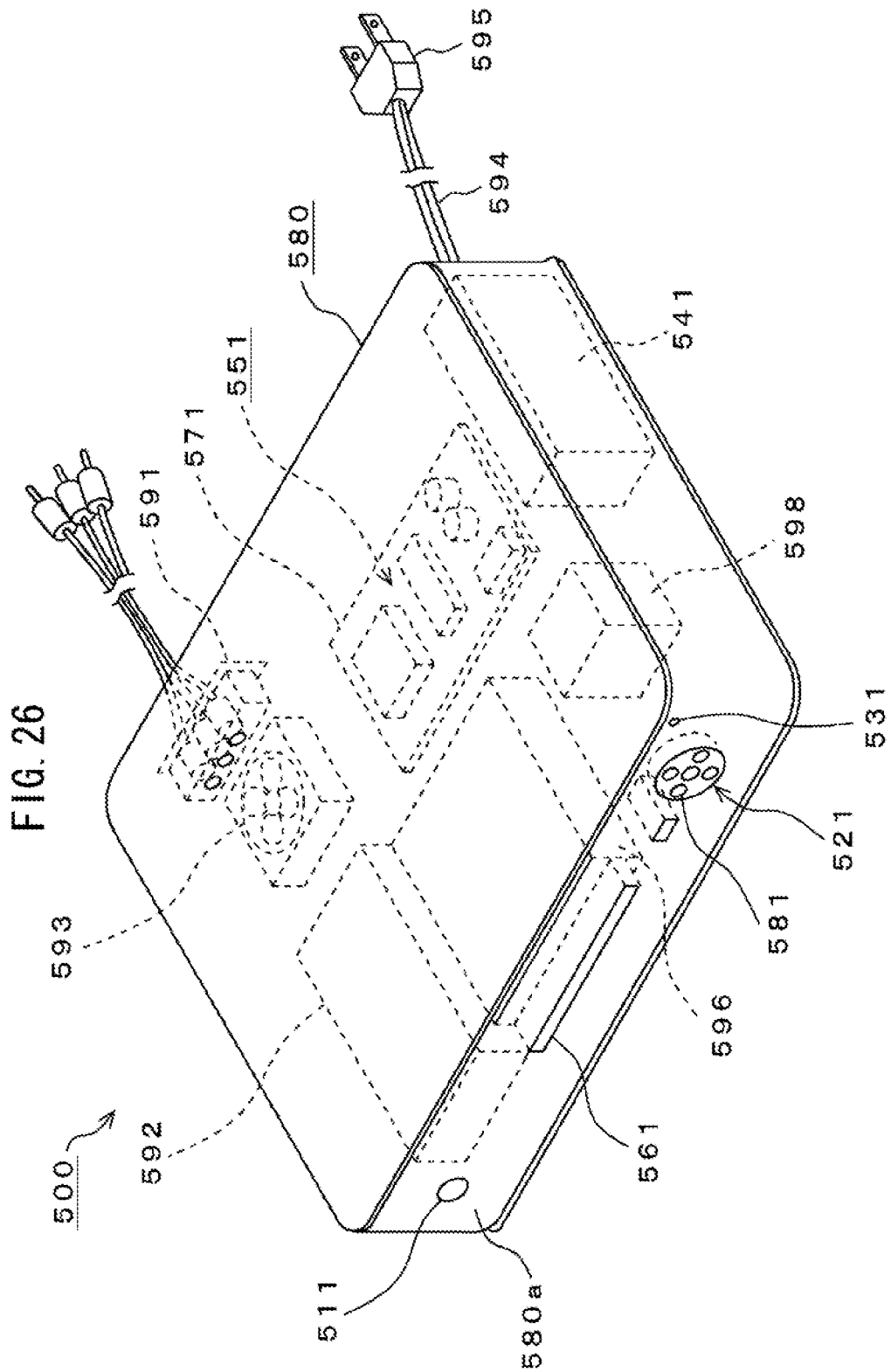
FIG. 26 is a perspective view of a recording-editing-reproducing apparatus 500 as a fifth embodiment for showing a configuration thereof.

FIG. 26 shows a configuration of a recording-editing-reproducing apparatus 500 as a fifth embodiment. In an embodiment, it is constituted so as to automatically edit the image data D34 of the subject and the sound data D13 when recording the ambient sound of the subject which are outputted from the video camera 200 of head-mounting type or the like.

The recording-editing-reproducing apparatus 500 shown in FIG. 26 constitutes the information-processing apparatus, and based on respective items of information on an editing start point and an editing end point, executes an editing process in which the image data D34 of the subject and the sound data D13 when recording the ambient sound of the subject at a period of time when the time cords relating to the editing start point and the editing end point are added, are automatically extracted and spliced from the image data D34 of the subject and the sound data D13. The recording-editing-reproducing apparatus 500, for example, constitutes a base station of the video camera 200 of head-mounting type.

The recording-editing-reproducing apparatus 500 has a rectangle shaped main body case 580. The front face of the main body case 580 is made as an operation panel 580a. A power supply switch 511, an operation unit 521 (a plurality of switches for operation), a light-receiving portion for a remote control (hereinafter, referred to as "remote sensor 531") and a slot 561 for an external recording medium are provided on the operation panel 580a. The power supply switch 511 is ON-operated when supplying the power to the recording-editing-reproducing apparatus 500.

The remote sensor 531 receives infrared light for operation from a remote controller, which is not shown, and outputs operation data to an information-processing unit 551. The operation unit 521 (switch kind) includes an edit start/stop switch, a reproduction start/stop switch, an editing length setting switch or the like. In the editing length setting switch, for example, there are prepared a switch for the edit short-time mode setting, a switch for the edit middle-time mode setting, and a switch for the edit long-time mode setting.

A recording medium of a CD-ROM, a MD, a memory stick or the like can be attached to the slot 561 for the external recording medium, and the image data D34 of the subject and the sound data D13 when recording the ambient sound of the subject which are automatically edited can be writable in the recording medium. The image data D34 of the subject and the sound data D13 when recording the ambient sound of the subject can be read from the recording medium to be automatically edited.

On the rear surface of the main body case 580, image-and-sound input-and-output terminals 591 are provided and can be connected to an external apparatus of the video camera 200 of head-mounting type, an image-and-sound-monitoring device or the like. In an embodiment, by using the image-and-sound input-and-output terminals 591, the image data D34 of the subject and the sound data D13 when recording the ambient sound of the subject which are automatically edited are transmitted to the external apparatus and the image data D34 of the subject and the sound data D13 when recording the ambient sound of the subject are received from the external apparatus to be automatically edited.

In the inside of the main body case 580, there is provided a circuit board 571. On the circuit board 571, a power supply circuit 541, a semiconductor integrated circuit device (LSI device) constituting an information-processing unit 551 and a radio communication unit 598, a built-in memory device 592, a device heat sink portion 593 and the like are mounted. The radio communication unit 598 is used, for example, when radio-communicating with the video camera 200 of head-mounting type. This radio communication process includes a transfer process of the image data D34 of the subject and the sound data D13 when recording the ambient sound of the subject when being shooting it by the video camera 200 or when the shooting ends.

For the built-in memory device 592, there is used a hard disk device (HDD) which is used in a case where the image data D34 of the subject and the sound data D13 when recording the ambient sound of the subject which are automatically edited are stored. It is needless to say that it is also allowed to store the image data D34 of the subject and the sound data D13 when recording the ambient sound of the subject before automatic editing. The hard disk device includes a magnetic disk and an optical disk.

The information-processing unit 551 extracts respective items of information on the editing start point and the editing end point and executes the automatic editing process with respect to the image data D34 of the subject and the sound data D13 when recording the ambient sound of the subject from the outside where there is the edit-offer. For example, the information-processing unit 551, corresponding to an editing length setting mode, automatically extracts the image data D34 of the subject and the sound data D13 at a period of time when the time cords relating to the editing start point and the editing end point are added from the image data D34 of the subject and the sound data D13 when recording the ambient sound of the subject and splices them based on respective items of information of the editing start point and the editing end point.

The power supply circuit 541 is connected to the information-processing unit 551, the radio communication unit 598, the built-in memory device 592, the device heat sink portion 593 or the like which are mentioned above and supplies a DC power to these parts. The device heat sink portion 593, for example, is a fan for CPU cooler. The power supply circuit 541 is connected with a predetermined length power supply cord 594, the end terminal portion of which is mounted with a power supply plug 595. The recording-editing-reproducing apparatus 500 is used by connecting the power supply plug 595 to a commercial power supply (AC100 or the like).

Figure 27:
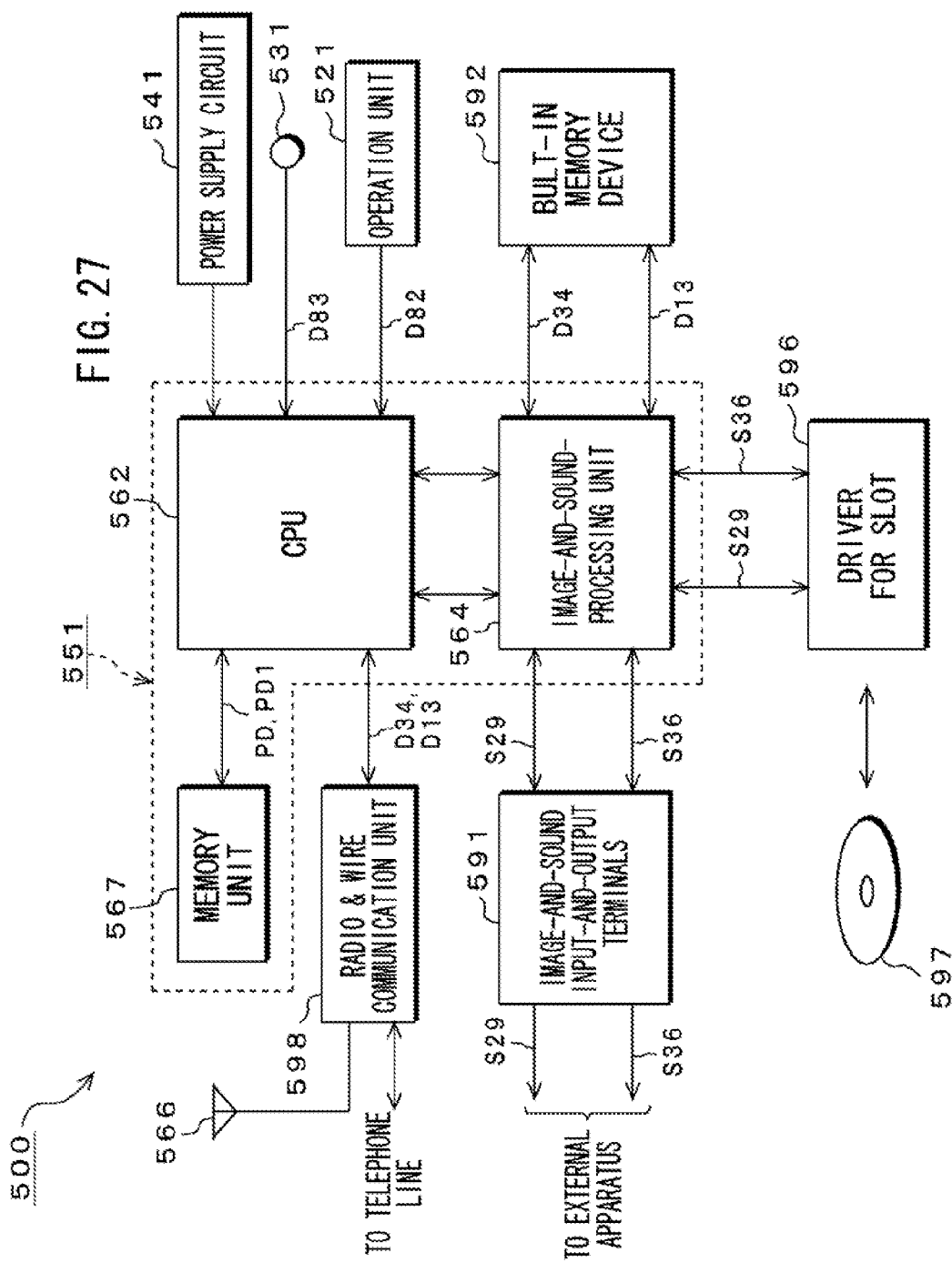
FIG. 27 is a block diagram of a control system of the recording-editing-reproducing apparatus 500 for showing a configuration thereof.

The following will describe a configuration of a control system of the recording-editing-reproducing apparatus 500. FIG. 27 shows the configuration of the control system of the recording-editing-reproducing apparatus 500. The recording-editing-reproducing apparatus 500 shown in FIG. 27 is constituted by mounting each function block on the circuit board 571 in the main body case 580 shown in FIG. 26. It should be noted that in FIG. 27, the portion corresponding to each portion shown in FIG. 26 is shown as the same numeral.

The recording-editing-reproducing apparatus 500 contains an antenna 566, the remote sensor 531, the power supply circuit 541, the information-processing unit 551, the operation unit 521, the image-and-sound input-and-output terminals 591, a radio and wire communication unit 598, the built-in memory device 592 and a driver 596 for media slot. The information-processing unit 551 has a CPU 562, a memory unit 567 and an image-and-sound-processing unit 564.

The operation unit 521 is connected to the CPU 562, and outputs operation data D82 generated by pushing down a push button of the power supply switch 511, which is shown in FIG. 26, the edit start/stop switch, the reproduction start/stop switch, the editing length setting switch or the like to the CPU 562. The CPU 562 is connected with the remote sensor 531, other than the operation unit 521, which receives infrared light for operation from a remote controller, which is not shown, and outputs the operation data D83 to the CPU 562.

When the power supply switch 511 is ON-operated, the CPU 562 controls the whole of the recording-editing-reproducing apparatus based on the system program. The memory unit 567 has an ROM, an RAM and an EEPROM or the like which are not shown. Data PD forming the system program for controlling the whole of the recording-editing-reproducing apparatus is stored in the ROM or the EEPROM of the memory unit 567. The RAM, which is not shown, is used as a work memory. The CPU 562 reads the data PD forming the system program out of the ROM or the EEPROM concurrently with the power supply ON to expand it in the RAM, and starts up the system to control the whole of the recording-editing-reproducing apparatus.

In the ROM or the EEPROM of the memory unit 567, a program for executing the automatic editing mode other than the system program is described. The program for this automatic editing mode is a computer readable program which is used for extracting the image data D34 of the subject and the sound data D13 at a period of time when the time cords relating to the editing start point and the editing end point are added from the image data D34 of the subject and the sound data D13 when recording the ambient sound of the subject and splicing them.

With respect the content thereof, there are described a step of inputting the image data D34 of the subject and the sound data D13 when recording the ambient sound of the subject, to which the editing start point information and the editing end point information are added, a step of judging whether or not the inputted image data D34 of the subject and the inputted sound data D13 when recording the ambient sound of the subject are automatically edited, and a step of extracting the image data D34 of the subject and the sound data D13 at a period of time when the time cords relating to the editing start point and the editing end point are added from the image data D34 of the subject and the sound data D13 when recording the ambient sound of the subject, which are judged to be automatically edited, and splicing them.

When data PD1 forming such a program is read out of the ROM or the EEPROM and executed, the CPU 562 can execute the editing process or the like in which the correspondence between the produced emotion data D45 showing the emotion of the living-body of the operator 130 and the image information of the subject and/or the sound information of the ambient sound of the subject, which are shot and collected, is established. When executing such an editing process, it is possible to extract the image data D34 and the sound data D13 at a period of time when emotion of the living-body is heightened to sweat in a hand during the time when the operator 130 is shooting the image of the subject from the image data D34 obtained by shooting the image of the subject by the operator 130 and the sound data D13 obtained by collecting the ambient sound of the subject, thereby enabling operator's specific image and sound data file to be produced.

The CPU 562 constitutes a judgment unit, and judges whether or not the image information of the subject and the sound information when recording the ambient sound of the subject which are inputted from the external apparatus to the image-and-sound-processing unit 564 through the image-and-sound input-and-output terminal 591 or the like are automatically edited based on an instruction from the operation unit 521 (outside). When there is an automatic editing instruction from the outside, a control command of the automatic editing execution is outputted to the image-and-sound-processing unit 564. When there is no the automatic editing instruction from the outside, a command of the effect that the automatic editing is not executed is outputted to the image-and-sound-processing unit 564.

The CPU 562 is connected with the image-and-sound-processing unit 564 which receives the control command of the CPU 562, detects the editing start point information and the editing end point information which are set as time codes with respect to recording time information, and extracts the image data D34 and the sound data D13 at a period of time when the editing start point information and the editing end point information are added and splices them. The image-and-sound-processing unit 564, for example, compresses the image data D34 with being compliant with MPEG-1 standard, and records it on a memory area for storing edited data which is newly provided in the built-in memory device 592. The reason why the editing data is shifted to the newly provided memory area is because it is the output preparation for executing smoothly output of the image data D34 and the sound data D13 after the editing with respect to the data distribution, a media recording process or a reproducing process.

The image-and-sound-processing unit 564 executes the compression processing being compliant with the MPEG-1 standard to data after the editing. According to this compression processing, data is compressed such that only the moving portion in the image is detected and kept. The compression processing is not limited to the MPEG-1; it is also allowed to employ respective standards from MPEG2 to MPEG-4 of high definition television correspondence or MPEG-7 standard in process of standardization presently. Thus, it becomes possible to automatically extract the image data D34 and the sound data D13 at a period of time when emotion of the living-body is heightened to sweat in a hand during the time when the operator 130 is shooting the image of the subject and it becomes possible to edit a specific image and sound corresponding to the amount of perspiration of the finger of the operator 130.

The above-mentioned CPU 562 is connected with the built-in memory device 592 through the image-and-sound-processing unit 564. The built-in memory device 592 is newly provided with the memory area which stores the image data D34 and the sound data D13 of the non-editing (hereinafter, referred to as "non-editing data area") and the memory area which stores the image data D34 and the sound data D13 after the editing. In the newly provided memory area, there are stored the image data D34 and the sound data D13 relating to extracted scene f(SIII), extracted scene f(SIII+SII), extracted scene f(SIII+SII+SI) read out of the memory unit 567 or the like.

If an instruction of the effect that data is not automatically edited is set, the image data D34 of the subject and the sound data D13 when recording the ambient sound of the subject are sequentially stored in the non-editing data memory area directly, without having relation with the existence/non-existence of the addition of the editing start point information, the editing end point information or the like. For the built-in memory device 592, there is used a hard disk device of a photo disk, a magnetic disk or the like.

The above-mentioned image-and-sound-processing unit 564 is connected with the driver 596 for media slot by which the image after the editing is written in the recording medium 597 based on an image display signal S29 and on a occasion of the editing, the image display signal S29 relating to the non-editing image is read out of the recording medium 597. It is needless to say that the sound after the editing is written in the recording medium 597 together with the image based on an sound signal S36 and on a occasion of the editing, the sound signal S36 relating to the non-editing image is read out of the recording medium 597.

By doing in this manner, it is possible to make the CPU 562 have a recording control function for moving-picture-recording-processing to the predetermined recording medium 597 based on the living-body information. The recording medium 597 is used by attaching to the driver 596. For the recording medium 597, there is used a media slot of a recording medium of a CD-ROM, a MD or the like, a memory stick or the like. When such a moving picture recording processing is executed, it becomes possible to distribute a memorial file on which the operator's specific image data D34 and sound data D13 after the editing are recorded. It is possible to reproduce and enjoy the image data D34 and the sound data D13 at a period of time when emotion of the living-body is heightened to sweat in a hand during the time when the operator 130 is shooting the image of the subject from the recording medium 597 of the CD-ROM, the MD or the like.

The image-and-sound-processing unit 564 is connected with the image-and-sound input-and-output terminals 591 constituting an input unit, the video display signal S29 after the editing is transmitted to the external apparatus and on a occasion of the editing, the video display signal S29 relating to the non-editing video is received from the external apparatus. In an embodiment, the image-and-sound input-and-output terminals 591 input the image information of the subject and the sound information when recording the ambient of the subject on which the editing start point information and the editing end point information are added from the external apparatus to the image-and-sound-processing unit 564 or the built-in memory device 592. It is needless to say that the sound signal S36 after the editing is transmitted together with the image display signal S29 to the external apparatus and on a occasion of the editing, the sound signal S36 relating to the non-editing image is received from the external apparatus.

The above-mentioned CPU 562 is connected with the radio and wire communication unit 598 constituting the input unit. The radio and wire communication unit 598 communicates with the external apparatus. In an embodiment, the radio and wire communication unit 598 inputs image information of the subject and sound information when recording the ambient sound of the subject on which the editing start point information and the editing end point information are added from the external apparatus to the image-and-sound-processing unit 564 or the built-in memory device 592. The radio and wire communication unit 598 is connected with the antenna 566. For example, the CPU 562 controls the radio and wire communication unit 598 to transmit the extracted and spliced image data D34 of the subject and the extracted and spliced sound data D13 when recording the ambient sound of the subject based on the editing process to the video camera 200 of head-mounting type by using the radio communication function of the radio and wire communication unit 598 and the antenna 66.

Further, the radio and wire communication unit 598 may be also connected to the telephone line and is connected to the Internet through the telephone line. The radio and wire communication unit 598 receives the control of the CPU 562 and executes the distributing process. For example, the radio and wire communication unit 598 distributes the image data D34 and the sound data D13 at a period of time when emotion of the living-body is heightened to sweat in a hand during the time when the operator 130 is shooting the image of the subject. Thus, it becomes possible to download a file (algorithm) on which the operator's specific image data D34 and sound data D13 are recorded to the other user through the Internet or the like.

It should be noted that it is also allowed to reproduce the image data D34 of the subject and the sound data D13 when recording the ambient sound of the subject which are extracted and spliced based on the editing process according to the editing length setting mode, by possessing a reproduction control function to the CPU 562. When such a reproducing process is executed, it is possible to reproduce the image data D34 and the sound data D13 at a period of time when emotion of the living-body is heightened to sweat in a hand during the time when the operator 130 is shooting the image of the subject based on the short-time edition mode, the middle-time edition mode or the long-time edition mode, and it becomes possible to view a memorial file on which the operator's specific image data D34 and sound data D13 are recorded with the suitable length.

Also, the power supply circuit 541 supplies the DC power converted from the commercial power supply to the remote sensor 531, the information-processing unit 551, the operation unit 521, radio and wire communication unit 598, the built-in memory device 592, the driver 596 or the like.

Figure 28:
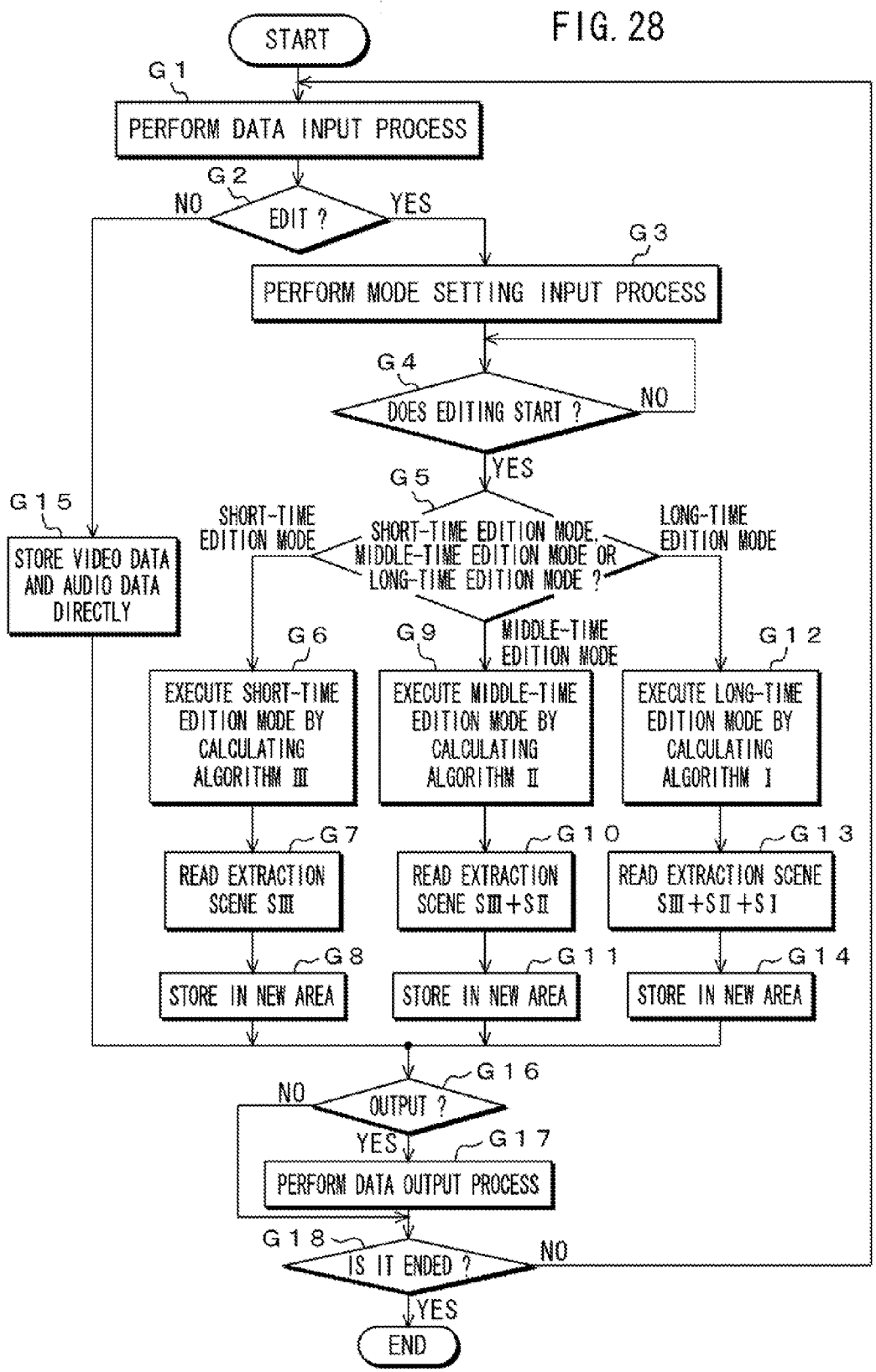
FIG. 28 is a flowchart showing an information processing example in the recording-editing-reproducing apparatus 500.

The following will describe an information-processing example in the recording-editing-reproducing apparatus 500. FIG. 28 shows an information-processing example in the recording-editing-reproducing apparatus 500. In an embodiment, an automatic edition mode is prepared with respect to the information editing process. When the automatic edition mode is selected, the image data D34 of the subject and the sound data D13 when recording the ambient sound of the subject at a period of time when the editing start point information and editing end point information are added are extracted and spliced from the image data D34 of the subject and the sound data D13 when recording the ambient sound of the subject. With respect to the automatic edition mode, a case in which three kinds of modes such as a short-time edition mode, a middle-time edition mode and a long-time edition mode are prepared is cited. It is needless to say that the power supply plug 595 of the recording-editing-reproducing apparatus 500 is connected to the commercial power supply and the power supply is turned on.

By making these as the editing process condition, the CPU 132 executes a data input process in step G1 of the flowchart shown in FIG. 28 based on input operation instruction. At that time, the user operates the operation unit 521 to instruct the CPU 562 on the effect that data is inputted. By this operation, operation data D82 of the effect that the data is inputted is output from the operation unit 521 to CPU 562. Further, the user operates the operation unit 521 to instruct the CPU 562 on whether or not the data is automatically edited. By this operation, operation data D82 of the effect that the data is automatically edited or not is output from the operation unit 521 to CPU 562.

At that time, the video camera 100 as explained in the embodiment 1, the video camera 200 of head-mounting type as explained in the embodiment 2, the digital camera 300 as explained in the embodiment 3 or the mobile phone 400 with camera as explained in the embodiment 4 receives the data. The video camera 100, the digital camera 300 and the mobile phone 400, for example, in the wire form, receives the image data D34 of the subject and the sound data D13 when recording the ambient sound of the subject on which the editing start point information and the editing end point information are added. The video camera 200, for example, in the radio form, receives the image data D34 of the subject and the sound data D13 when recording the ambient sound of the subject on which the editing start point information and the editing end point information are added. The image data D34 and the sound data D13 at this time is stored in the RAM or the like of the memory unit 567 temporally.

It should be noted that the operator may operate the operation unit 521 in this point of time to instruct the CPU 562 on the output form after the automatic editing of the data. For example, the operator operates the operation unit 521 to output the operation data D82 of instructing the CPU 562 to which point the data after the automatic editing is output. To the video camera 100, the digital camera 300, the mobile phone 400 and an image display monitor, which is not shown, the image data D34 of the subject and the sound data D13 when recording the ambient sound of the subject after the automatic editing are output in the wire form. The image display monitor includes a personal computer (hereinafter, referred to as PC). To the video camera 200, the image data D34 of the subject and the sound data D13 when recording the ambient sound of the subject after the automatic editing is output with the radio form.

Next, at step G2, the CPU 562 discriminates whether or not the data is automatically edited and the process is branched based on this discrimination result. In an embodiment, when an instruction that the data is automatically edited is set, the process shifts to step G3 where the CPU 562 executes a mode setting input process. For example, the editing length setting switch of the operation unit 521 is operated and the operation data D82 with respect to the editing length setting mode is inputted to the CPU 562. At that time, one switch is selected from a short-time edition mode switch, a middle-time edition mode switch or a long-time edition mode switch in the operation unit 521.

For example, when the short-time edition mode switch is selected, the operation unit 521 outputs the operation data D82 showing the short-time edition mode to the CPU 562. The short-time edition mode is referred to as a mode in which the image data D34 and the sound data D13 of the shortest one period of time from a point of time when the editing start point information is added to a point of time when the editing end point information is added are extracted from a plurality of periods of time from a point of time when the editing start point information is added to a point of time when the editing end point information is added.

Also, when the middle-time edition mode switch is selected, the operation unit 521 outputs the operation data D82 showing the middle-time edition mode to the CPU 562. The middle-time edition mode is referred to as a mode in which the image data D34 and the sound data D13 of other periods of time than the period of time extracted by the short-time edition mode are spliced.

Further, when the long-time edition mode switch is selected, the operation unit 521 outputs the operation data D82 showing the long-time edition mode to the CPU 562. The long-time edition mode is referred to as a mode in which the short-time edition mode and the middle-time edition mode are combined, for example, all of the image data D34 and the sound data D13 of the periods of time from a point of time when the editing start point information is added to a point of time when the editing end point information is added are spliced.

Next, at step G4, the CPU 562 waits an editing start. At that time, the user operates the push-button switch of the operation unit 521 constituting an editing start switch to instruct a start of the editing process to the CPU 562. The operation unit 521 outputs the operation data D82 instructing the start of the editing process to the CPU 562.

When the operation unit 521 instructs the editing process start to the CPU 562, the process shifts to step G5 where the CPU 562 branches the control based on the short-time edition mode, the middle-time edition mode or the long-time edition mode which is set previously. When the short-time edition mode is set at the step G3, the process shifts from the step G5 to step G6 where the CPU 562 calculates algorithm III and executes the short-time edition mode. At that time, the time codes ts, te are detected from the recording time information T, and the arithmetic calculation for extracting the image data D34 and the sound data D13 of the period of time when the time codes ts, te are added from the image data D34 and the sound data D13 is assumed to be "f" and the extracted scene edited by calculating the algorithm III is assumed to be "f (SIII).

Next, at step G7, the CPU 562 reads the image data D34 and the sound data D13 relating to extracted scene f (SIII) out of the RAM of the memory unit 567. Thereafter, the process shifts to step G8 where the image data D34 and the sound data D13 relating to the extracted scene f(SIII) read out of the RAM are stored in the memory area newly provided in the built-in memory device 592. Thereafter, the process shifts to step G16.

Also, when the middle-time edition mode is set at the step G3, the process shifts from the step G5 to step G9 where the CPU 562 calculates algorithm II and executes the middle-time edition mode. At that time, extracted scene which is edited by calculating the algorithm II is assumed to be "f(SIII+SII)".

Next, at step G10, the CPU 562 reads the image data D34 and the sound data D13 relating to extracted scene f(SIII+SII) out of the RAM of the memory unit 567. Thereafter, the process shifts to step G11 where the image data D34 and the sound data D13 relating to the extracted scene f(SIII+SI) read out of the RAM are stored in the memory area newly provided in the built-in memory device 592. Thereafter, the process shifts to the step G16.

Further, when the long-time edition mode is set at the step G3, the process shifts from the step G5 to step G12 where the CPU 562 calculates algorithm I and executes the long-time edition mode. At that time, extracted scene which is edited by calculating the algorithm I is assumed to be "f(SIII+SII+SI)".

Next, at step G13, the CPU 562 reads the image data D34 and the sound data D13 relating to extracted scene f(SIII+SII+SI) out of the RAM of the memory unit 567. Thereafter, the process shifts to step G14 where the image data D34 and the sound data D13 relating to the extracted scene f(SIII+SII+SI) read out of the RAM are stored in the memory area newly provided in the built-in memory device 592. Thereafter, the process shifts to the step G16.

It should be noted that at the step G2, when the instruction of the effect that data is not automatically edited is set, the process shifts to step G15. At the step G15, the CPU 562 executes the non-editing data storing processing. In this data storing processing, the image data D34 of the subject and the sound data D13 when recording the ambient sound of the subject are stored sequentially in the predetermined memory area in the built-in memory device 592 directly without having relation with the existence/non-existence of the addition of editing end point information, editing end point information or the like. This is because a case in which editing offer is rushed and shifts to the editing process at a later date is considered. Thereafter, the process shifts to the step G16.

At the step G16, the CPU 562 judges whether or not the image data D34 and the sound data D13 after the editing is output. At that time, the user operates the operation unit 521 to instruct the CPU 562 on the effect that data is outputted. By this operation, the operation unit 821 outputs the operation data D82 of the effect that the data is outputted to the CPU 562. Further, the user operates the operation unit 521 to instruct the CPU 562 on the effect that either one of the short-time edition mode, the middle-time edition mode or the long-time edition mode is selected. BY this operation, the operation unit 521 outputs the operation data D82 of the effect either one of the short-time edition mode, the middle-time edition mode or the long-time edition mode is selected to the CPU 562.

Next, at step G17, the CPU 562 executes the data output process based on the output form and either one of short-time edition mode, middle-time edition mode or the long-time edition mode, which are set previously. For example, if the video camera 200 receives the image data D34 of the subject and the sound data D13 when recording the ambient sound of the subject and the data after the editing is output to the video camera 200 when the short-time edition mode is set, the image data D34 and the sound data D13 relating to the extracted scene f (SIII) which is read out of the built-in memory device 592 are transmitted to the video camera 200 through the radio and wire communication unit 598.

In the information processing and communication unit 250 of the video camera 200, the image data D34 and the sound data D13 relating to the extracted scene f (SIII) is reproduced. It is possible to display impressive scenes based on the image data D34 and the sound data D13 at a period of time when emotion of the living-body is heightened to sweat in a hand during the time when the operator 130 is shooting the image of the subject on the left display unit 229*a* and the right display unit 229*b*. It becomes possible to view a memorial file on which operator's specific image data D34 and sound data D13 are recorded. The data output point is not limited to the digital camera 200; it is allowed to employ a monitor for image reproducing display exclusive use.

Also, if the digital camera 300 receives the image data D34 of the subject and the sound data D13 when recording the ambient sound of the subject and the data after the editing is output to the digital camera 300 when the middle-time edition mode is set, the image data D34 and the sound data D13 relating to the extracted scene f(SIII+SII) which is read out of the built-in memory device 592 are reproduced in the information-processing unit 315 of the digital camera 300. Such a reproduction allows to be displayed the impressive scenes based on the image data D34 and the sound data D13 at a period of time when emotion of the living-body is heightened to sweat in a hand during the time when the operator 130 is shooting the image of the subject and at a next period of time when emotion of the living-body is heightened to sweat in a hand during the time when the operator 130 is shooting the image of the subject. It becomes possible to view a memorial file on which operator's specific image data D34 and sound data D13 are recorded. The data output point is not limited to the digital camera 300; it is allowed to employ an image display monitor such as a television set.

Further, if the video camera 100 receives the image data D34 of the subject and the sound data D13 when recording the ambient sound of the subject and the data after the editing is output to the image display monitor when the long-time edition mode is set, the image data D34 and the sound data D13 relating to the extracted scene f(SIII+SII+SI) which is read out of the built-in memory device 592 are transferred to image display monitor which reproduces them.

Such a reproduction allows to be monitor-displayed the impressive scenes based on all of the extracted image data D34 and sound data D13 at a period of time when emotion of the living-body is heightened to sweat in a hand during the time when the operator 130 is shooting the image of the subject, at a next period of time when emotion of the living-body is heightened to sweat in a hand during the time when the operator 130 is shooting the image of the subject, and a further period of time when emotion of the living-body is heightened to sweat in a hand during the time when the operator 130 is shooting the image of the subject, and so on.

Further, it becomes possible to view a memorial file on which operator's specific image data D34 and sound data D13 are recorded. The data output point is not limited to the image display monitor; it is allowed to employ the video camera 100.

Thereafter, at step G18, CPU 562 judges the end. For example, it is judged whether or not the editing stop switch of the operation unit 521 is operated. Alternatively, it is judged whether or not the power supply switch 511 is operated and power-off information is detected. When the editing stop switch of the operation unit 582 is operated or when the power-off information is detected, the editing process ends. When the editing stop switch of the operation unit 521 is not operated and when the power-off information is not detected, the process returns to the step G1 where the above-mentioned processes are repeated.

In this manner, according to the recording-editing-reproducing apparatus 500 as the embodiment 5, the image data D34 of the subject and the sound data D13 when recording the ambient sound of the subject which are obtained from the video camera 200 of head-mounting type or the like are automatically edited and reproduced. The recording-editing-reproducing apparatus 500 executes the editing process in which the image data D34 of the subject and the sound data D13 when recording the ambient sound of the subject at a period of time when the time codes relating to the editing start point and the editing end point are added are automatically extracted and spliced from the image data D34 of the subject and the sound data D13 when recording the ambient of the subject based on the respective items of the editing start point information and the editing end point information.

Consequently, when the image data D34 and the sound data D13 relating to the extracted scene f(SIII), f(SIII+SII), f(SIII+SII+SI) or the like are reproduced, it is possible to monitor-display the impressive scenes based on the image data D34 and the sound data D13 at a period of time when emotion of the living-body is heightened to sweat in a hand during the time when the operator 130 is shooting the image of the subject, thereby enabling a memorial file on which the operator's specific image data D34 and sound data D13 are recorded to be viewed and listened with excellent reproducibility.

Embodiment 6

Figure 29:
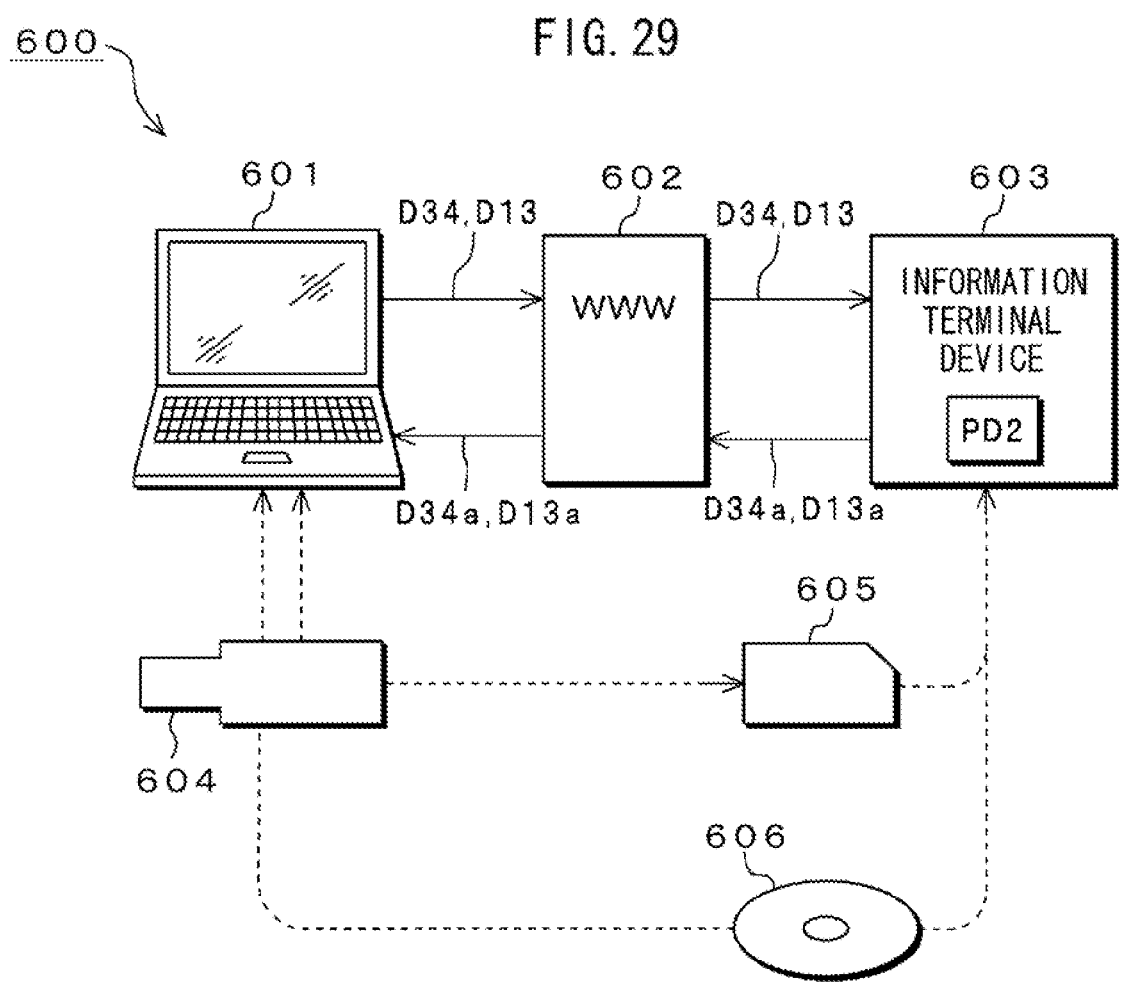
FIG. 29 is a block diagram of an editing service system 600 as a sixth embodiment for showing a configuration thereof.

FIG. 29 shows a configuration of an editing service system 600 as a sixth embodiment. The editing service system 600 shown in FIG. 29 constitutes an embodiment of the information-processing system according to the present application, processes the information obtained by shooting an image of a subject and by collecting ambient sound of the subject, and provides the editing process of the information. It is also allowed for the editing process to be either free of charge or charge. The editing process becomes a subject to charging in a case in which a charge system is constituted, and it becomes such that a business model is constituted.

In the editing service system 600, an information-communication-processing device 601 of a user is connected to an information terminal device 603 of the editing process provider through the Internet 602 (www). The information-communication-processing device 601 includes a desktop type PC and a note type PC.

The information-communication-processing device 601 is connected with an image-acquiring apparatus 604, and processes the information obtained by shooting the image of the subject and by collecting the ambient sound of the subject. The image-acquiring apparatus 604 includes the video camera 100 as explained in the embodiment 1, the video camera 200 of head-mounting type as explained in the embodiment 2, the digital camera 300 as explained in the embodiment 3 and the mobile phone 400 with a camera as explained in the embodiment 4.

In an embodiment, the information-communication-processing device 601 has a function for reproducing the image data D34 of the subject and the sound data D13 when recording the ambient sound of the subject which are obtained from the image-acquiring apparatus 604, but it has not the function of the recording-editing-reproducing apparatus 500 as explained in the embodiment 5.

When the editing service is received by the editing service system 600, the information-communication-processing device 601 is connected to the information terminal device 603 of the editing process provider through the Internet 602 and the information-communication-processing device 601 transmits the image data D34 of the subject and sound data D13 when recording the ambient sound of the subject, on which respective items of editing start point information and editing end point information are added. The information terminal device 603 has a function of automatically editing the image data D34 of the subject and the sound data D13 when recording the ambient sound of the subject which are received from the information-communication-processing device 601.

For the information terminal device 603, there is used the recording-editing-reproducing apparatus 500 explained in the embodiment 5. It is needless to say that in the information terminal device 603, a program is mounted which describes a step of inputting the image data D34 of the subject and the sound data D13 when recording the ambient sound of the subject on which the editing start point information and the editing end point information as explained in FIG. 27 are added, a step of judging whether or not the inputted image data D34 of the subject and the inputted sound data D13 when recording the ambient sound of the subject are automatically edited, and a step of extracting the image data D34 and the sound data D13 at a period of time when the editing start point information and the editing end point information are added from the image data D34 of the subject and the sound data D13 when recording the ambient sound of the subject which are judged to be automatically edited and splicing them.

Thus, it becomes possible to return to the user the image data D34a and the sound data D13a relating to the extracted scenes f(SIII), f(SIII+SII), f(SIII+SII+SI) and the like which are automatically edited by the editing process provider, for example, as subject to charging.

Figure 30:
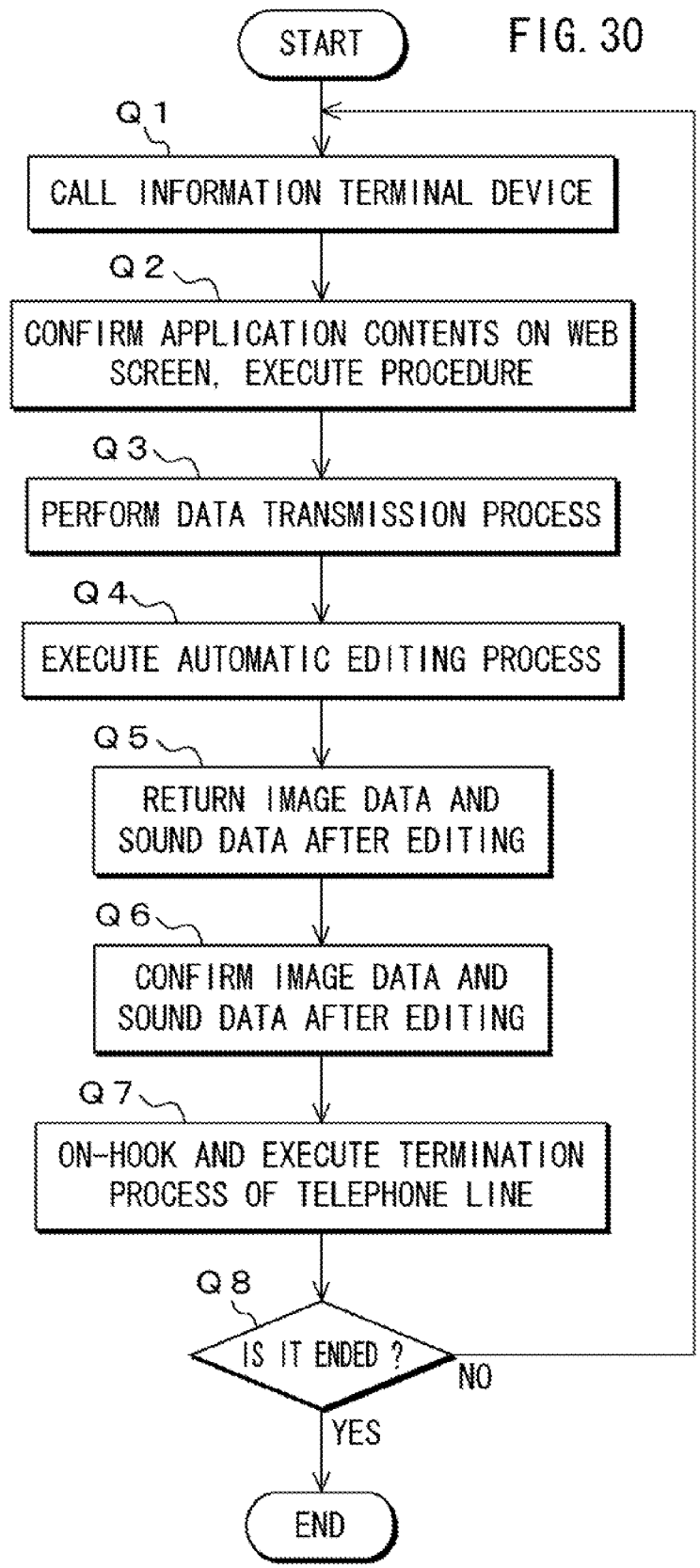
FIG. 30 is a flowchart showing an information processing example in the editing service system 600.

The following will describe an information-processing example in the editing service system 600. FIG. 30 shows the information-processing example in the editing service system 600. In an embodiment, the information-editing provider is provided with the information terminal device 603, and there is cited a case in which the image data D34a and the sound data D13a relating to the extracted scenes f(SIII), f(SIII+SII), f(SIII+SII+SI) or the like after editing are provided to the information-communication-processing device 601 of the user by a download form.

By setting this as the editing process condition, the user calls the information terminal device 603 of the information-editing provider at step Q1 shown in FIG. 30 in order to receive the editing service. At that time, the information-communication-processing device 601 call-transmits to the information terminal device 603 and a telephone line is connected through the Internet 602.

Next, at step Q2, the contents of the application are confirmed on the Web screen of the Internet 602 and the procedure to the information-editing provider is executed. For example, the contents of the registration for receiving the editing service are displayed in the information-communication-processing device 601 and the contents of the registration are confirmed on the Web screen and thereafter, the procedure OK button is operated. Thereafter, at step Q3, the information-communication-processing device 601 executes a data transmission process to the information terminal device 603. Data contains the image data D34 of the subject and the sound data D13 when recording the ambient sound of the subject on which the editing start point information and the editing end point information are added.

On the information-editing provider side, at step Q4, the information terminal device 603 executes a data automatic editing process (see FIG. 28). Impressive scenes are extracted by this automatic editing process, the remaining image and sound data may be thrown away directly or, it is also allowed to save in only a predetermined period of time on the information-editing provider side. With respect to the image and sound data saved on the information-editing provider side, it is good if it is the non-disclosure treatment.

Then, at step Q5, the information terminal device 603 executes a return process of the image data D34a and the sound data D13a after the editing to the information-communication-processing device 601. The image data D34a and the sound data D13a after the editing is stored in a memory device or the like of the information-communication-processing device 601. Thereafter, at step Q6, the user executes a confirmation process of the image data D34a and the sound data D13a after the editing on the Web screen.

After the end of confirmation, at step Q7, the information-communication-processing device 601 is ON-hooked and a process for terminating the telephone line is executed. Then, at step Q8, the information-communication-processing device 601 judges the end. For example, it is judged whether or not the power supply switch is operated and the power-off information is detected. When the power supply switch is operated and the power-off information is detected, the editing service mode ends. When the power supply switch is not operated or the power-off information is not detected, the process returns to the step Q1 where the above-mentioned processes are repeated.

In this manner, since the embodiments of the information-processing apparatus, the information-processing method and the program relating to the present application are applied to the editing service system 600 as the sixth embodiment, when the information obtained by shooting the image of the subject and by collecting the ambient sound of the subject is processed, the information terminal device 603 executes the editing process or the like which establishes the correspondence between the emotion data D45 or the like generated by detecting living-body information showing emotion of the living-body of the operator 130 and the image data D34 of the subject and/or the sound data D13 when recording the ambient sound of the subject which are shot and collected, by calling the information terminal device 603 of the information-editing provider.

Consequently, even if there is no the automatic editing program in the information-processing apparatus of the user, it becomes possible to acquire the image data D34a and the sound data D13a relating to extracted scenes f(SIII), f(SIII+SII), f(SIII+SII+SI) or the like which is automatically edited by the editing process provider as subject to charging. With respect to the image data D34a and the sound data D13a relating to the extracted scenes f(SIII), f(SIII+SII), f(SIII+SII+SI) or the like after the editing, it is allowed to be selected as either a download format or a carrying form such as a recording medium 597. It should be noted that the edit offer to the information-editing provider may be carried out not only through the Internet but also by handing over a recording medium of a memory stick 605, a CD-ROM 606 or the like on which the image data D34 of the subject and the sound data D13 when recording the ambient sound of the subject are recorded at a shop.

Embodiment 7

Figure 31:
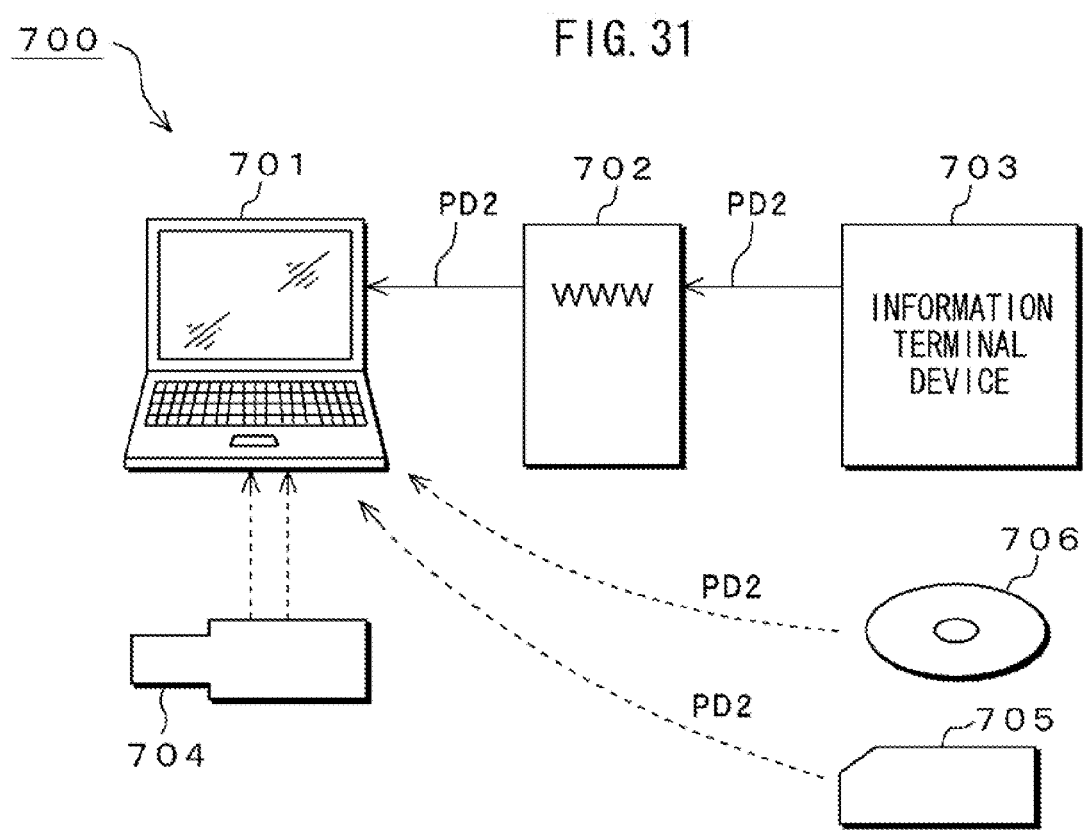
FIG. 31 is a block diagram of an editing-software-presenting system 700 as a seventh embodiment for showing a configuration thereof.

FIG. 31 shows a configuration of an editing software offer system 700 as a seventh embodiment.

The editing software offer system 700 shown in FIG. 31 constitutes another embodiment of the information-processing system according to the present application, processes the information obtained by shooting an image of a subject and by collecting ambient sound of the subject, and provides software for the editing process in which an editing program PD2 which may be necessary for the editing process of the information is described (hereinafter, referred to as editing software). It is also allowed for the editing software to be either free of charge or charge. The editing software becomes a subject to charging in a case in which a charge system is constituted, and it becomes such that a business model is constituted.

In the editing software offer system 700, an information-communication-processing device 701 of the user and an information terminal apparatus 703 of the editing process provider are coupled through the Internet 702 (www). The information-communication-processing device 701 contains a desktop type PC and a note type PC which includes a recording-editing-reproducing function as explained in the embodiment 5. It is needless to say that it is also allowed to combine a personal computer with communication function and a normal recording/editing/reproducing apparatus and use it.

The information-communication-processing device 701 is connected with an image-acquiring apparatus 704, and processes the information obtained by shooting the image of the subject and by collecting the ambient sound of the subject. The image-acquiring apparatus 704 includes the video camera 100 as explained in the embodiment 1, the video camera 200 of head-mounting type as explained in the embodiment 2, the digital camera 300 as explained in the embodiment 3 and the mobile phone 400 with a camera as explained in the embodiment 4.

In an embodiment, the information-communication-processing device 701 has a function for reproducing the image data D34 of the subject and the sound data D13 when recording the ambient sound of the subject which are obtained from the image-acquiring apparatus 704 and has the recording-editing-reproducing function as explained in the embodiment 5 but mounts no editing software. It is because the editing software is handled in the option and because version-update of the editing software can be flexibly handled that the editing software is not mounted on the information-communication-processing device 701 from the beginning.

When the offer of the editing software is received by the editing software offer system 700, the information-communication-processing device 701 is connected to the information terminal apparatus 703 of the editing process provider through the Internet 702 and the information-communication-processing device 701 transmits, for example, registration information of an apparatus registered number, a user ID and the like. The information terminal apparatus 703 verifies the registration information transmitted from the information-communication-processing device 701 and entered in, in case of having obtained verification OK, distribution of the editing software for automatically editing the image data D34 of the subject and the sound data D13 when recording the ambient sound of the subject.

For the information terminal apparatus 703, there is used a desktop type PC or a note type PC. A server system is introduced to the information terminal apparatus 703 in which a program is mounted which describes a step of inputting the image data D34 of the subject and the sound data D13 when recording the ambient sound of the subject on which the editing start point information and the editing end point information as explained in FIG. 27 are added, a step of judging whether or not the inputted image data D34 of the subject and the inputted sound data D13 when recording the ambient sound of the subject are automatically edited, and a step of extracting image data D34 and sound data D13 at a period of time when the editing start point information and the editing end point information are added from the image data D34 of the subject and the sound data D13 when recording the ambient sound of the subject which are judged to be automatically edited and splicing them.

Thus, the editing process provider can distribute the editing software in response to the registration request, and the user edits automatically the image data D34 of the subject and the sound data D13 when recording the ambient sound of the subject by the information-communication-processing device 701 at hand, and can produce an image and sound album file of impressive scenes assembled with the image data D34 and the sound data D13 relating to extracted scenes f(SIII), f(SIII+SII), f(SIII+SII+SI) and the like after the editing.

The following will describe an information-processing example in the editing software offer system 700. FIG. 32 shows the information-processing example in the editing software offer system 700. In an embodiment, the information editing provider is provided with the information terminal apparatus 703 and there is cited a case in which if an offer of the editing software is received by the editing software offer system 700, the editing software is distributed when the registration information of an apparatus registered number, a user ID or the like of the information-communication-processing device 701 is transmitted and verification OK is obtained.

By setting this as the editing software acquisition condition, the user calls the information terminal apparatus 703 of the information-editing provider in order to receive the editing software at step R1 of a flowchart shown in FIG. 32. At that time, the information-communication-processing device 701 call-transmits to the information terminal apparatus 703 and a telephone line is connected through the Internet 702.

Next, at step R2, the contents of the registration are confirmed on the Web screen of the Internet 702 and a registration procedure to the information-editing provider is executed. For example, the contents of the registration for receiving the editing software are displayed in the information-communication-processing device 701. At that time, registration information of an apparatus registered number, a user ID or the like of the apparatus is inputted to the information-communication-processing device 701. Then, the contents of the registration are confirmed on the Web screen and thereafter, the procedure OK button is operated. The registration information is transmitted from the information-communication-processing device 701 to the information terminal apparatus 703.

Thereafter, at step R3, the information terminal apparatus 703 verifies the registration information transmitted from the information-communication-processing device 701 and entered in. In the verification process in this case, for example, an apparatus registered number reserved when having sold the information-communication-processing device 701 and an apparatus registered number when registering are comparison-collated. Verification OK is made when the both numbers accorded.

When the verification OK is obtained, at step R4, a distributing process of the editing software for automatically editing the image data D34 of the subject and the sound data D13 when recording the ambient sound of the subject is executed. This editing software is downloaded in the information-communication-processing device 701. Thereafter, it becomes possible to execute the data automatic editing process on the user side (see FIG. 28). Then, at step R5, the information-communication-processing device 701 is ON-hooked and a process for terminating the telephone line is executed.

In this manner, since the embodiments of the information-processing apparatus, the information-processing method and the program relating to the present application are applied to the editing software offer system 700 as the seventh embodiment, when the information obtained by shooting the image of the subject and by collecting the ambient sound of the subject is processed, the information terminal apparatus 703 is provided in the information editing provider, the information terminal apparatus 703 of the information editing provider is called, registration information of an apparatus registered number, a user ID or the like of the information-communication-processing device 701 is transmitted and when verification OK is obtained, the editing software is distributed.

Consequently, even if there is no the automatic editing program in the information-communication-processing device 701 when purchasing apparatus, at a later date, it is possible to receive an offer from an editing process provider and further, in a case in which the change occurs in the contents of the editing software, it is possible to execute the update procedure simply. It becomes possible for the information-communication-processing device 701 to execute the editing process or the like which establishes the correspondence between the emotion data D45 or the like generated by detecting the living-body information showing emotion of the operator 130 and the image data D34 of the subject and/or the sound data D13 when recording the ambient sound of the subject which are shot and collected. It should be noted that a distribution request of the editing software can be done through the Internet, by mail or coming to the shop. The editing software from the information-editing provider to the user is not limited to the download through the Internet; it can be done by handing over a recording medium of a memory stick 705, a CD-ROM 706 or the like in which the editing software is described at the shop.

In this manner, according to the first to seventh embodiments, without executing the complicated operation of the user mainly, it becomes possible to automatically extract and to automatically edit the scene(s) that the user desires from the enormous quantity of recording data.

The present application is suitable for applying to a video camera for taking a moving picture, a digital camera for taking a still picture, a mobile phone with camera, a mobile terminal apparatus with camera, an information reproducing apparatus for reproducing image and sound information obtained from these apparatuses, a system including a recording-editing-reproducing disk apparatus for saving data or the like.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An information-processing apparatus that processes information obtained by shooting an image of a subject and by collecting ambient sound of the subject, the apparatus comprising:
   an image-and-sound-recording unit that shoots the image of the subject to output image information on the image and collects the ambient sound of the subject to output sound information on the ambient sound;
   an information output unit that detects living-body information showing emotion of living-body of an operator who operates the image-and-sound-recording unit to output the living-body information, the information output unit including:
   (a) a pulse sensor that detects a pulse rate of the operator who operates the image-and-sound-recording unit on a time series to generate pulse information; and
   (b) a blood pressure sensor that detects a blood pressure of the operator who operates the image-and-sound-recording unit on the time series to generate blood pressure information; and
   an information-processing unit that:
   (a) establishes correspondence between the living-body information outputted from the information output unit and at least one of the image information of the subject and the sound information of the ambient sound of the subject, the image information and the sound information being outputted from the image-and-sound-recording unit; and
   (b) derives pulse-wave transfer time by calculating the pulse information obtained from the pulse sensor and the blood pressure information obtained from the blood pressure sensor.

2. The information-processing apparatus of claim 1, wherein the information output unit includes a perspiration sensor that detects an amount of perspiration of the operator who operates the image-and-sound-recording unit on a time series to output the living-body information to the information-processing unit.

3. The information-processing apparatus of claim 2, wherein the information-processing unit compares the living-body information outputted from the information output unit with discrimination criterion information which becomes a discrimination criterion of the living-body information,
   wherein when the living-body information exceeding the discrimination criterion is detected, editing start point information is added to at least one of the image information of the subject and the sound information of the ambient sound of the subject, and
   wherein when the living-body information equal to or less than the discrimination criterion is detected, editing end point information is added to at least one of the image information of the subject and the sound information of the ambient sound of the subject.

4. The information-processing apparatus of claim 3, wherein the information-processing unit executes an editing process by extracting the image information and the sound information in a period of time from a point of time when the editing start point information is added to a point of time when the editing end point information is added from the image information of the subject and the sound information of the ambient sound of the subject based on the editing start point information and the editing end point information and splicing the extracted image information and the extracted sound information.

5. The information-processing apparatus of claim 4, wherein the information-processing unit reproduces the image information of the subject and the sound information of the ambient sound of the subject, the image information and the sound information being extracted and spliced based on the editing process.

6. The information-processing apparatus of claim 4, wherein the information-processing unit distributes the image information of the subject and the sound information of the ambient sound of the subject, the image information and the sound information being extracted and spliced based on the editing process.

7. The information-processing apparatus of claim 4, wherein the information-processing unit records the image information of the subject and the sound information of the ambient sound of the subject on a predetermined recording medium, the image information and the sound information being extracted and spliced based on the editing process.

8. A method of operating an information-processing apparatus which includes a memory device storing instructions, the method comprising:
(a) causing a processor to execute the instructions to obtain image information by shooting an image of a subject;
(b) causing the processor to execute the instructions to obtain sound information by collecting an ambient sound of the subject;
(c) causing the processor to execute the instructions to detect and produce:
  (i) living-body information showing emotion of living-body of an operator who operates an image-and-sound-recording unit;
  (ii) a pulse rate of the operator who operates the image-and-sound-recording unit on a time series to generate pulse information; and
  (iii) a blood pressure of the operator who operates the image-and-sound-recording unit on the time series to generate blood pressure information;
(d) causing the processor to execute the instructions to establish correspondence between the produced living-body information and at least one of the image information of the subject and the sound information of the ambient sound of the subject, the image information and the sound information being shot and collected; and
(e) causing the processor to execute the instructions to derive pulse-wave transfer time by calculating the pulse information obtained from the pulse sensor and the blood pressure information obtained from the blood pressure sensor.

9. The method according to claim of claim 8, which includes:
(a) causing the processor to execute the instructions to compare the living-body information with discrimination criterion information which becomes a discrimination criterion of the living-body information;
(b) causing the processor to execute the instructions to add editing start point information to at least one of the image information of the subject and the sound information of the ambient sound of the subject when detecting the living-body information which exceeds the discrimination criterion; and
(c) causing the processor to execute the instructions to add editing end point information to at least one of the image information of the subject and the sound information of the ambient sound of the subject when detecting the living-body information that is equal to or less than the discrimination criterion.

10. The method of claim 9, which includes:
(a) causing the processor to execute the instructions to input the image information of the subject and the sound information when recording the ambient sound of the subject, any one of the image information and the sound information including the editing start point information or the editing end point information;
(b) causing the processor to execute the instructions to determine whether automatic editing of the image information of the subject and the sound information when recording the ambient sound of the subject is performed, the image information and the sound information being inputted; and
(c) causing the processor to execute the instructions to extract the image information of the subject and the sound information when recording the ambient sound of the subject in a period of time from a point of time when the editing start point information is added to a point of time when the editing end point information is added from the image information of the subject and the sound information when recording the ambient sound of the subject, the image information and the sound information being judged to be automatically edited, and splicing the extracted image information and the extracted sound information.

11. The method of claim 10, wherein the image information of the subject and the sound information when recording the ambient sound of the subject are edited automatically based on a setting mode of editing length.

12. The method of claim 11, wherein the image information of the subject and the sound information when recording the ambient sound of the subject after the automatic editing are output based on the setting mode of the editing length.

13. A non-transitory computer readable recording medium storing instructions structured to cause an information-processing apparatus to:
(a) obtain image information by shooting an image of a subject;
(b) obtain sound information by collecting an ambient sound of the subject;
(c) detect and produce:
  (i) living-body information showing emotion of living-body of an operator who operates an image-and-sound-recording unit;
  (ii) a pulse rate of the operator who operates the image-and-sound-recording unit on a time series to generate pulse information; and
  (iii) a blood pressure of the operator who operates the image-and-sound-recording unit on the time series to generate blood pressure information.
(d) establish correspondence between the produced living-body information and at least one of the image information of the subject and the sound information of the ambient sound of the subject, the image information and the sound information being shot and collected; and
(e) derive pulse-wave transfer time by calculating the pulse information obtained from the pulse sensor and the blood pressure information obtained from the blood pressure sensor.

14. An information processing system that processes information obtained by shooting an image of a subject and by collecting ambient sound of the subject, the information processing system comprising:
an information-processing apparatus that processes information obtained by shooting the image of the subject and by collecting the ambient sound of the subject; and
an information-reproducing apparatus that reproduces image information of the subject and sound information of the ambient sound of the subject, the image information and the sound information being obtained from the information-processing apparatus, wherein the information-processing apparatus includes:

(a) an image-and-sound-recording unit that shoots the image of the subject to output the image information on the image and collects the ambient sound of the subject to output the sound information on the ambient sound;
(b) an information output unit that detects living-body information showing emotion of living-body of an operator who operates the image-and-sound-recording unit to output the living-body information, the information output unit including:
  (i) a pulse sensor that detects a pulse rate of the operator who operates the image-and-sound-recording unit on a time series to generate pulse information; and
  (ii) a blood pressure sensor that detects a blood pressure of the operator who operates the image-and-sound-recording unit on the time series to generate blood pressure information; and
(c) an information-processing unit that:
  (i) establishes correspondence between the living-body information outputted from the information output unit and at least one of the image information of the subject and the sound information of the ambient sound of the subject, the image information and the sound information being outputted from the image-and-sound-recording unit; and
  (ii) derives pulse-wave transfer time by calculating the pulse information obtained from the pulse sensor and the blood pressure information obtained from the blood pressure sensor.

* * * * *